US008986700B2

(12) United States Patent
Jackson et al.

(10) Patent No.: US 8,986,700 B2
(45) Date of Patent: *Mar. 24, 2015

(54) IMMUNOGENIC LIPOPEPTIDES COMPRISING T-HELPER AND CYTOTOXIC T-LYMPHOCYTE (CTL) EPITOPES

(75) Inventors: David Jackson, North Balwyn (AU); Weiguang Zeng, Kensington (AU)

(73) Assignee: The Council of the Queensland Institute of Medical Research, Herston, Queensland (AU)

( * ) Notice: Subject to any disclaimer, the term of this patent is extended or adjusted under 35 U.S.C. 154(b) by 726 days.

This patent is subject to a terminal disclaimer.

(21) Appl. No.: 12/901,457

(22) Filed: Oct. 8, 2010

(65) Prior Publication Data
US 2011/0280899 A1 Nov. 17, 2011

Related U.S. Application Data

(63) Continuation of application No. 10/524,936, filed as application No. PCT/AU03/01019 on Aug. 12, 2003, now Pat. No. 7,833,532.

(60) Provisional application No. 60/403,328, filed on Aug. 12, 2002.

(51) Int. Cl.
| A61K 39/00 | (2006.01) |
| A61K 39/145 | (2006.01) |
| A61K 39/29 | (2006.01) |
| A61K 39/385 | (2006.01) |
| A61K 39/39 | (2006.01) |
| C07K 14/005 | (2006.01) |
| C07K 14/195 | (2006.01) |
| C07K 19/00 | (2006.01) |

(52) U.S. Cl.
CPC ............ *A61K 39/39* (2013.01); *A61K 39/145* (2013.01); *A61K 39/29* (2013.01); *A61K 39/385* (2013.01); *A61K 2039/5158* (2013.01); *A61K 2039/55516* (2013.01); *A61K 2039/55544* (2013.01); *A61K 2039/57* (2013.01); *A61K 2039/6018* (2013.01); *A61K 2039/6031* (2013.01); *A61K 2039/6037* (2013.01); *A61K 2039/6075* (2013.01); *C07K 14/005* (2013.01); *C07K 14/195* (2013.01); *C07K 19/00* (2013.01); *C12N 2760/16122* (2013.01); *C12N 2760/16134* (2013.01); *C12N 2760/18422* (2013.01); *C12N 2770/24222* (2013.01); *C12N 2770/24234* (2013.01)
USPC ........ 424/184.1; 530/359; 530/327; 530/326; 530/325; 424/185.1; 424/193.1

(58) Field of Classification Search
USPC .......... 424/184.1, 185.1, 193.1; 530/359, 327, 530/326, 325
IPC .................... A61K 39/00,39/12, 39/145, 39/29, A61K 38/16
See application file for complete search history.

(56) References Cited

U.S. PATENT DOCUMENTS

| 5,580,563 A | 12/1996 | Tam |
| 5,700,910 A | 12/1997 | Metzger et al. |
| 6,024,964 A | 2/2000 | Jung et al. |

FOREIGN PATENT DOCUMENTS

| WO | WO 93/15205 A2 | 8/1993 |
| WO | WO 93/22343 A1 | 11/1993 |

OTHER PUBLICATIONS

Barany, G. et al., "Solid-Phase Peptide Synthesis: A Silver Anniversary Report," Int. J. Pept. Prot. Res 1987, pp. 705-739, vol. 30.
Benmohamed, L., et al., "Lipopeptide immunization without adjuvant induces potent and long-lasting B, T helper, and cytotoxic T lymphocyte responses against a malaria liver stage antigen in mice and chimpanzees," Eur. J. Immunol, 1997, pp. 1242-1253, vol. 27.
Benmohamed, L., et al., "High immunogenicity in chimpanzees of peptides and lipopeptides derived from four new *Plasmodium falciparum* pre-erythrocytic molecules," Vaccine 18, 2000, pp. 2843-2855.
Boeckler, C., et al., "Design of highly immunogenic liposomal constructs combining structurally independent B cell and T helper cell peptide epitopes," Eur. J. Immunol, 1999, pp. 2297-2308, vol. 29.
Deliyannis Georgia, et al., "Induction of long-term memory CD8+ T cells for recall of viral clearing responses against influenza virus," Journal of Virology, May 2002, pp. 4212-4221, vol. 76, No. 9.
Deprez, B., et al., "Pimelautide or Trimexautide as Built-in Adjuvants Associated with an HIV-1-Derived Peptide: Synthesis and in Vivo Induction of Antibody and Virus-Specific Cytotoxic T-Lymphoyte-Mediated Response," J. Med. Chem., 1995, pp. 459-465, vol. 38.
Deprez, B., et al., "Comparative efficiency of simple lipopeptide constructs for in vivo induction of virus-specific CTL," Vaccine, 1996, pp. 375-382, vol. 14, No. 5.
Deres, K., et al., "In vivo priming of virus-specific cytotoxic T lymphocytes with synthetic lipopeptide vaccine," Nature, Nov. 30, 1989, pp. 561-564, vol. 342.
Ghosh, S., et al., "Antigenic and immunogenic properties of totally synthetic peptide-based anti-fertility vaccines," International Immunology, 1999, pp. 1103-1110, vol. 11.
Jackson, D.C., et al., "The Central Role Played by Peptides in the Immune Response and the Design of Peptide-Based Vaccines against Infectious Diseases and Cancer," Current Drug Targets, 2002, pp. 175-196, vol. 2, No. 2.

(Continued)

*Primary Examiner* — David Lukton
(74) *Attorney, Agent, or Firm* — Fenwick & West LLP

(57) ABSTRACT

The present invention provides synthetic immunogenic lipopeptide molecules comprising co-linear T-helper and CTL epitopes, and methods for their production and use in the generation of primary and secondary immune responses, and for the vaccination of animal subjects against particular CTL epitopes. More particularly, the present invention provides highly soluble lipopeptides wherein the lipid moiety is attached to the terminal side-chain group of an internal lysine or lysine analog, preferably to the terminal side-chain group of an internal diamino acid residue. Preferably the internal lysine or lysine analog is positioned between the T-helper epitope and the CTL epitope.

18 Claims, 16 Drawing Sheets

(56) References Cited

OTHER PUBLICATIONS

Figure 1:
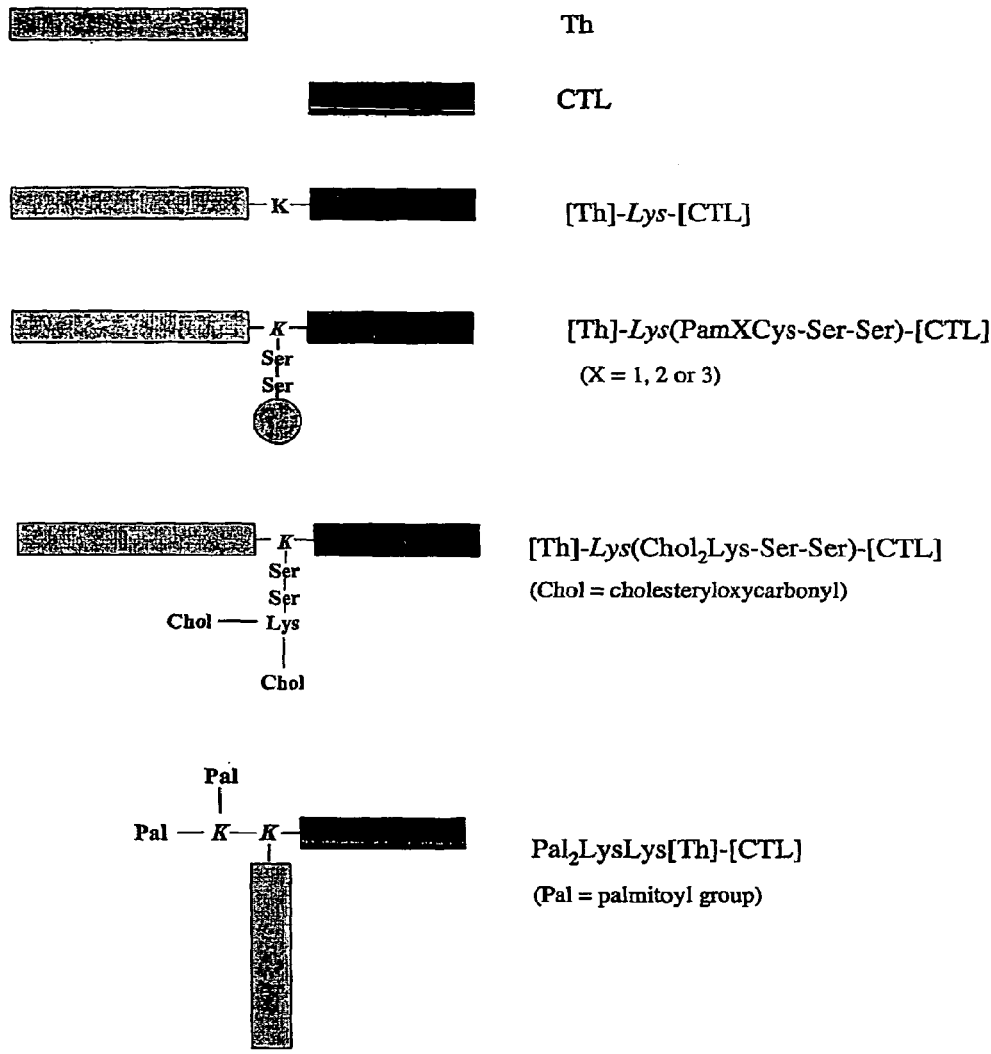

Jung, G., et al., "Increased Production of Specific Antibodies by Presentation of the Antigen Determinants with Covalently Coupled Lipopeptide Mitogens," Angew Chem, Int. Ed. Engl., 1985, pp. 872-273, No. 10.

Kaumaya, P., et al., "Peptide Vaccines Incorporating a 'Promiscuous' T-cell Epitope Bypass Certain Haplotype Restricted Immune Responses and Provide Broad Spectrum Immunogenicity," Journal of Molecular Recognition, 1993, pp. 81-94, vol. 6.

Martinon, F., et al., "Immunization of Mice With Lipopeptides Bypasses the Prerequisite for Adjuvant, Immune Response to Lipopeptides," The Journal of Immunology, 1992, pp. 3416-3422, vol. 149, No. 10.

Metzger, J., et al., "Synthetic S-(2, 3-Dihydroxypropyl)-cysteinyl Peptides Derived from the N-terminus of the Cytochrome Submit of the Photoreaction Centre of *Rhodopseudomonas viridis* Enhance Murine Splenocyte Proliferation, Novel Synthetic Lipopeptides Activate Splenocytes," Journal of Peptide Science, 1995, pp. 184-190, vol. 3.

Mühlradt, P., et al., "Isolation, Structure Elucidation, and Synthesis of a Macrophage Stimulatory Lipopeptide from *Mycoplasma fermentans* Acting at Picomolar Concentration," J. Exp. Med., Jun. 2, 1997, pp. 1951-1958, vol. 185, No. 11.

Mühlradt, P., et al., "Structure and Specific Activity of Macrophage-Stimulating Lipopeptides from *Mycoplasma hyorhinis*," Infection and Immunity, Oct. 1998, pp. 4804-4810, vol. 66, No. 10.

Nardin, E. H., et al., "A Totally Synthetic Polyoxime Malaria Vaccine Containing *Plasmodium falciparum* B Cell and Universal T Cell Epitopes Elicits Immune Responses in Volunteers of Diverse HLA Types," The Journal of Immunology, 2001, pp. 481-489, vol. 166.

Nardin, E. H., et al., "*Plasmodium falciparum* polyoximes: highly immunogenic synthetic vaccines constructed by chemoselective ligation of repeat B-cell epitopes and a universal T-Cell epitope of CS protein," Vaccine, 1998, pp. 590-600, vol. 16, No. 6.

Obert, M., et al., "Protection of mice against SV40 tumours by Pam$_3$Cys conjugated with SV40 T antigen-derived peptide, K(698)-T(708)," Vaccine, 1998, pp. 161-169, vol. 16, No. 2/3.

Sauzet, J.-P., et al., "Long-lasting anti-viral cytotixic T lymphocytes induced in vivo with chimeric-multirestricted lipopeptides," Vaccine, 1995, pp. 1339-1345, vol. 13, No. 14.

Toyokuni, T., et al., "Synthetic Vaccines: Synthesis of a Dimeric Tn Antigen-Lipopeptide Conjugate that Elicits Immune Responses against Tn-Expressing Glycoproteins," J. Am. Chem. Soc., 1994, pp. 395-396, vol. 116.

Wiesmüller, K.-H., et al., "Synthesis of the Mitogenic S-[2, 3-Bis(palmitoyloxy) propyl]-N-palmitoylpentapeptide from *Escherichia coli* Lipoprotein," Hoppe-Seyler's Z. Physiol. Chem., 1983, pp. 593-606, Bd. 364.

Wiesmüller, K.-H., et al., "Novel low-molecular-weight synthetic vaccine against foot-and-mouth disease containing a potent B-cell and macrophage activator," Vaccine, Feb. 1989, pp. 29-33, vol. 7.

Zeng, W., et al., "Highly Immunogenic and Totally Synthetic Lipopeptides as Self-Adjuvanting Immunocontraceptive Vaccines," Journal of Immunology, Nov. 1, 2002, pp. 4905-4912, vol. 169, No. 9.

Supplementary Partial European Search Report, EP 03783851, Aug. 22, 2007, 3 pages.

Supplementary European Search Report, European Patent Application No. 03783852.1, Sep. 7, 2007, 9 pages.

Baz, A. et al., "Branched and Linear Lipopeptide Vaccines Have Different Effects on Primary CD4+ and CD8+ T-Cell Activation by Induce Similar Tumor-Protective Memory CD8+ T=Cell Responses," Vaccine, 2008, pp. 2570-2579, vol. 26.

Benmohamed, L. et al., "Lipopeptide Vaccines—Yesterday, Today, and Tomorrow," The Lancet, Jul. 2002, pp. 425-431, vol. 2.

Deliyannis, G. et al., "Induction of Long-Term Memory CD8+ T Cells for Recall of Viral Clearing Responses Against Influenza Virus," Journal of Virology, May 2002, pp. 4212-4221, vol. 76, No. 9.

European Extended Search Report, European Application No. 10011465.1, Mar. 9, 2011, 8 pages.

Jackson, D.C. et al., "The Central Role Played by Peptides in the Immune Response and the Design of Peptide-Based Vaccines Against Infectious Diseases and Cancer," Current Drug Targets, 2002, pp. 175-196, vol. 3.

Jackson, D.C. et al., "Preparation and Properties of Totally Synthetic Immunogens," Vaccine, 2000, pp. 355-361, vol. 18.

Zeng, W. et al., "Assembly of Synthetic Peptide Vaccines by Chemoselective Ligation of Epitopes: Influence of Different Chemical Linkages and Epitope Orientations on Biological Activity," Vaccine, 2001, pp. 3843-3852, vol. 19.

Zeng, W. et al., "Highly Immunogenic and Totally Synthetic Lipopeptides as Self-Adjuvanting Immunocontraceptive Vaccines," The Journal of Immunology, 2002, pp. 4905-4912.

Zeng, W. et al., "Totally Synthetic Lipid-Containing Polyoxime Peptide Constructs are Potent Immunogens," Vaccine, 2000, pp. 1031-1039, vol. 18.

| PEPTIDE | AMINO ACID SEQUENCE |
|---|---|
| [Th] | ALNNRFQIKGVELKS |
| [CTL] | TYQRTRALV |
| [Th]-[CTL] | ALNNRFQIKGVELKSTYQRTRALV |
| [Th]-Lys-[CTL] | ALNNRFQIKGVELKSKTYQRTRALV |
| [P25]-Lys-[LLO91-99] | KLIPNASLIENCTKAELKGYKDGNEYI |
| [P25]-Lys-[SIINFEKL] | KLIPNASLIENCTKAELKSIINFEKL |
| [P25-Lys-[HCV] | KLIPNASLIENCTKAELKDLMGYIPLV |
| [Th]-Lys(Pam$_3$Cys-Ser-Ser)-[CTL] | ALNNRFQIKGVELKSKTYQRTRALV |
| [Th]-Lys(Pam$_2$Cys-Ser-Ser)-[CTL] | ALNNRFQIKGVELKSKTYQRTRALV |
| [P25]-Lys(Pam$_2$Cys-Ser-Ser)-[LLO91-99] | KLIPNASLIENCTKAELKGYKDGNEYI |
| [P25]-Lys(Pam$_2$Cys-Ser-Ser)-[SIINFEKL] | KLIPNASLIENCTKAELKSIINFEKL |
| [P25]-Lys(Pam$_2$Cys-Ser-Ser)-[HCV] | KLIPNASLIENCTKAELKDLMGYIPLV |

FIGURE 2

IMMUNOGENIC LIPOPEPTIDES COMPRISING T-HELPER AND CYTOTOXIC T-LYMPHOCYTE (CTL) EPITOPES

CROSS-REFERENCE TO RELATED APPLICATIONS

This application is a continuation of application Ser. No. 10/524,936, filed Oct. 20, 2005,now U.S. Pat. No. 7,833,532, which is the National Stage of International Application No. PCT/AU2003/001019, filed Aug. 12, 2003, which claims the benefit of and priority to U.S. Provisional. Application No. 60/403,328, filed Aug. 12, 2002; all of which are incorporated herein by reference.

FIELD OF THE INVENTION

The present invention relates generally to the field of immunology; and more particularly to reagents for generating cellular responses to a peptide immunogen, and methods for using said reagents for enhancing the immune response of a subject, or for the vaccination of a subject. Even more specifically, the present invention relates to novel lipopeptides having enhanced immunogenic activity, specifically an enhanced ability to activate a T cell response to a CD8+ T cell epitope to induce cell mediated immunity against an invading pathogen or tumour cell. The present invention also provides formulations and vaccine compositions comprising said lipopeptides, such as, for example, in combination with a pharmaceutically acceptable carrier or excipient, and methods for making and using the formulations and vaccine compositions of the invention.

BACKGROUND TO THE INVENTION

1. General

This specification contains amino acid sequence information prepared using PatentIn Version 3.1, presented herein after the Abstract. Each sequence is identified in the sequence listing by the numeric indicator <210> followed by the sequence identifier (e.g. <210>1, <210>2, etc). The length of each sequence and source organism are indicated by information provided in the numeric indicator fields <211> and <213>, respectively. Sequences referred to in the specification are defined by the term "SEQ ID NO:", followed by the sequence identifier (eg. SEQ ID NO: 1 refers to the sequence designated as <400>1).

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step Or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally-equivalent products, compositions and methods are clearly within the scope of the invention, as described herein.

All the references cited in this application are specifically incorporated by reference herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactive, Germany);
10. Sakakibara, D., Teichman, J., Lien, E. Land Fenichel, R. L. (1976). Biochem. Biophys. Res. Commun. 73 336-342
11. Merrifield, R. B. (1963). J. Am. Chem. Soc. 85, 2149-2154.
12. Barany, G. and Merrifield, R. B. (1979) in The Peptides (Gross, E. and Meienhofer, eds.), vol. 2, pp. 1-284, Academic Press, New York.
13. Wünsch, E., ed. (1974) Synthese von Peptiden in Houben-Weyls Methoden der Organischen Chemie (Müler, E., ed.), vol. 15, 4th edn., Parts 1 and 2, Thieme, Stuttgart.
14. Bodanszky, M. (1984) Principles of Peptide Synthesis, Springer-Verlag, Heidelberg.
15. Bodanszky, M. & Bodanszky, A. (1984) The Practice of Peptide Synthesis, Springer-Verlag, Heidelberg.
16. Bodanszky, M. (1985) Int. J. Peptide Protein Res. 25, 449-474.
17. Handbook of Experimental Immunology, Vols. I-IV (D. M. Weir and C. C. Blackwell, eds., 1986, Blackwell Scientific Publications).

2. Description of the Related Art

Immunotherapy or vaccination are attractive for the prophylaxis or therapy of a wide range of disorders, such as, for example, certain infectious diseases, or cancers. However, the application and success of such treatments are limited in part by the poor immunogenicity of the target CTL epitope. Synthetic peptides, representing T cell immunogens elicit only weak immunity when delivered in isolation and as a consequence, are not effective in vaccine compositions. Full-length proteins containing CTL epitopes do not efficiently enter the MHC class I processing pathway. Additionally, CTL epitopes are HLA-restricted and the large degree of HLA polymorphism in human populations means that CTL-based vaccines may not provide broad coverage to all genotypes within a population.

Several techniques are used to enhance the immune response of a subject to a peptide immunogen.

It is known that utilization of an adjuvant formulation that is extrinsic to the peptide immunogen (i.e. it is mixed with the immunogen prior to use), such as, for example, complete Freund's adjuvant (CFA), will enhance the immune response of a subject to a peptide immunogen. However, many of the adjuvants currently available are too toxic for use in humans, or simply ineffective. Moreover, adjuvants of this type require prior formulation with the peptide immunogen—immediately before administration, such formulations often having a low solubility or being insoluble.

Lipopeptides, wherein a lipid moiety that is known to act as an adjuvant is covalently coupled to a peptide immunogen, may be capable of enhancing the immunogenicity of an otherwise weakly immunogenic peptide in the absence of an extrinsic adjuvant [Jung et al., Angew Chem, Int Ed Engl 10, 872, (1985); Martinon et al., J Immunol 149, 3416, (1992); Toyokuni et al., J Am Chem Soc 116, 395, (1994); Deprez, et al., J Med Chem 38, 459, (1995); and Sauzet et al., Vaccine 13, 1339, (1995); BenMohamed et al., Eur. J. Immunol. 27, 1242, (1997); Wiesmuller at al., Vaccine 7, 29, (1989); Nardin et al., Vaccine 16, 590, (1998); Benmohamed, et al. Vaccine 18, 2843, (2000); and Obert, et al., Vaccine 16, 161, (1998)]. Suitable lipopeptides show none of the harmful side effects associated with adjuvant formulations, and both antibody and cellular responses have been observed against lipopeptides.

Several different fatty acids are known for use in lipid moieties. Exemplary fatty acids include, but are not limited to, palmitoyl, myristoyl, stearoyl and decanoyl groups or, more generally, any $C_2$ to $C_{30}$ saturated, monounsaturated, or polyunsaturated fatty acyl group is thought to be useful.

The lipoamino acid N-palmitoyl-S-[2,3-bis(palmitoyloxy) propyl]cysteine, also known as $Pam_3Cys$ or $Pam_3Cys$-OH (Wiesmuller et al., Z. Physiol. Chem. 364 (1983), p 593), is a synthetic version of the N-terminal moiety of Braun's lipoprotein that spans the inner and outer membranes of Gram negative bacteria. $Pam_3Cys$ has the structure of Formula (I):

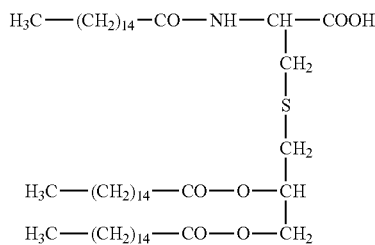

U.S. Pat. No. 5,700,910 to Metzger et al (Dec. 23, 1997) describes several N-acyl-S-(2-hydroxyalkyl)cysteines for use as intermediates in the preparation of lipopeptides that are used as synthetic adjuvants, B lymphocyte stimulants, macrophage stimulants, or synthetic vaccines. Metzger et al. also teach the use of such compounds as intermediates in the synthesis of $Pam_3Cys$-OH (Wiesmuller et al., Z. PhysioL Chem. 364 (1983), p 593), and of lipopeptides that comprise this lipoamino acid or an analog thereof at the N-terminus. The lipopeptides are prepared by coupling a lipoamino acid moiety to the peptide moiety during the synthesis process.

$Pam_3Cys$ when coupled to a CTL epitope peptide has been shown to be capable of stimulating virus-specific cytotoxic T lymphocyte (CTL) responses against influenza virus-infected cells (Deres et al., Nature 342, 561, 1989) and to elicit protective antibodies against foot-and-mouth disease (Wiesmuller et al., Vaccine 7, 29, 1989; U.S. Pat. No. 6,024, 964 to Jung et al., Feb. 15, 2000) when coupled to the N-terminus of an appropriate synthetic B cell epitope.

Recently, $Pam_2Cys$ (also known as dipalmitoyl-5-glyceryl-cysteine or S-[2,3-bis(palmitoyloxy)propyl]cysteine), an analogue of $Pam_3Cys$, has been synthesised (Metzger, J. W., A. G. Beck-Sickinger, M. Loleit, M. Eckert, W. G. Bessler, and G. Jung. 1995. J Pept Sci 1:184.) and been shown to correspond to the lipid moiety of MALP-2, a macrophage-activating lipopeptide isolated from mycoplasma (Sacht, G., A. Marten, U. Deiters, R. Sussmuth, G. Jung, E. Wingender, and P. F. Muhlradt. 1998. Eur J Immunol 28:4207: Muhlradt, P. F., M. Kiess, H. Meyer, R. Sussmuth, and G. Jung. 1998. Infect Immun 66:4804: Muhlradt, P. F., M. Kiess, H. Meyer, R. Sussmuth, and G. Jung. 1997. J Exp Med 185:(1951). $Pam_2Cys$ has the structure of Formula (II):

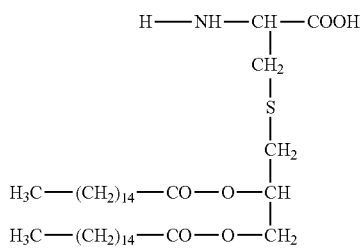

$Pam_2Cys$ is reported to be a more potent stimulator of splenocytes and macrophages than $Pam_3Cys$ (Metzger et al., J Pept. Sci 1, 184, 1995; Muhlradt et al., J Exp Med 185, 1951, 1997; and Muhlradt et al., Infect Immun 66, 4804, 1998).

Generation of a strong CD8+ T cell response against a given CTL epitope requires the generation of a strong T helper cell response. $CD4^+$ T-helper cells function in cell-mediated immunity (CMI) by secreting sufficient cytokines, such as, for example IL-2, to thereby facilitate the expansion of $CD8^+$ T cells or by interacting with the antigen presenting cell (APC) thereby rendering it more competent to activate $CD8^+$ T cells. Accordingly, it is desirable to administer a CTL epitope in conjunction with at least one T-helper cell epitope (Vitiello et al., J. Clin. Invest. 95, 341-349, 1995; Livingston et al., J. Immunol. 159, 1383-1392, 1997). These epitopes are recognized by T-helper cells in the context of MHC class II molecules on the surface of the APC.

The CTL epitope or isolated epitope can be administered in conjunction with a large protein having a range of T helper epitopes in order to accommodate the diversity of class II alleles within a population of individuals. Alternatively, promiscuous or permissive T-helper epitope-containing peptides are administered in conjunction with the CTL epitope or epitopes. Promiscuous or permissive T-helper epitope-containing peptides are presented in the context of a vast majority of MHC class II haplotypes, such that they induce strong $CD4^+$ T helper responses in the majority of an outbred human population. Examples of promiscuous or permissive T-helper epitopes are tetanus toxoid peptide, Plasmodium falciparum pfg27, lactate dehydrogenase, and HIVgp120 (Contreas et al., Infect. Immun, 66, 3579-3590, 1998; Gaudebout et al., J. A.I.D.S. Human Retrovirol 14, 91-101, 1997; Kaumaya et al., J. Mol. Recog. 6, 81-94, 1993; and Fern and Good J. Immunol. 148, 907-913, 1992). Ghosh et al., Immunol 104, 58-66, 2001 and International Patent Application No. PCT/AU00/00070

(WO 00/46390) also describe promiscuous T-helper epitopes from the fusion protein of Canine Distemper Virus (CDV-F). Certain promiscuous T-helper epitopes promote strong CTL responses to a given CTL epitope, and can bypass certain haplotype restricted immune responses (Kaumaya et al., *J. MoL Recog.* 6, 81-94, 1993).

Routinely, a vaccine preparation will comprise a mixture of polypeptides comprising the T-helper cell epitope and CTL epitope, however it is also known to consist of a single polypeptide comprising both the T-helper epitope and the CTL epitope.

SUMMARY OF THE INVENTION

In work leading up to the present invention, the inventors sought to improve methods for producing highly immunogenic lipopeptides having a lipid moiety and a polypeptide moiety comprising both a T helper epitope and a CTL epitope against which an immune response is desired. The inventors showed that a highly immunogenic lipopeptide comprising both T-helper and CTL epitopes can be produced by synthesizing a single polypeptide molecule comprising said epitopes with an internal lysine residue or internal lysine analog residue and then coupling the lipid moiety to the side-chain amino group of said internal lysine residue or said internal lysine analog residue, as opposed to the N-terminal attachments described previously. This enables the lipopeptide of the present invention to be synthesized conveniently using a single amino acid chain, thereby requiring no post-synthesis modification to incorporate both epitopes.

By positioning said one or more lysine residue(s) or one or more internal lysine analog residue(s) at predetermined locations within the polypeptide during peptide synthesis, the attachment site of the lipid is readily specified. Positioning of the lipid moiety in the lipopeptide can thus be targeted to enhance the utility of the end-product for vaccine or adjuvant formulations.

The inventors have found that attachment of the lipid moiety via the side-chain epsilon-amino group of an internal lysine residue or the terminal side-chain group of an internal lysine analog residue positioned between the amino acid sequences of the T helper epitope and the CTL epitope, provides an enhancement of dendritic cell maturation when compared to linear structures obtained in which lipid is attached to the N-terminus of the peptide.

One advantage provided by the lipopeptides of the present invention is that they are sufficiently immunogenic such that it is generally not necessary to include an extrinsic adjuvant in vaccine formulations comprising these lipopeptides.

The present invention clearly encompasses the attachment of a lipid moiety via the epsilon-amino group of an internal lysine residue or the terminal side-chain group of an internal lysine analog residue present in the amino acid sequence of the T helper epitope or the amino acid sequence of the CTL epitope, the only requirement being that the lipid moiety is not attached to the N-terminus or the C-terminus of the peptide. By "internal" means at a location other than the N-terminus or the C-terminus of a polypeptide comprising a T helper epitope and CTL epitope. As will be known to the skilled person, solubility of a vaccine containing CTL epitopes is highly desirable for producing vaccine formulations on a commercial basis.

Preferably, the lipid moiety is attached via the epsilon-amino group of a lysine residue or via the terminal side-chain group of a lysine analog residue positioned between the amino acid sequences of the T helper epitope and the CTL epitope.

Optionally, one or more amino acid spacers is added between the T-helper epitope and the CTL epitope, such as, for example, at either side of an internal lysine or lysine analog positioned between said epitopes.

A spacer of any conventional type can also be added between the lipid moiety and the polypeptide moiety. Particularly preferred spacers in this context consist of serine dimers, trimers, tetramers, etc. Alternative spacers, such as, for example, arginine dimers, trimers, tetramers, or 6-aminohexanoic acid, are also contemplated for use in this context.

As exemplified herein, the present inventors produced the lipopeptide of the invention by coupling the lipid moiety to an exposed epsilon-amino group of an internal lysine residue in the synthetic peptide moiety. Optionally, a spacer may be added to the exposed epsilon amino group before addition of the lipid moiety.

As will be apparent from the disclosure herein, a lipoamino acid of Formula (III) or (IV) may be added directly to the epsilon amino group of the internal lysine residue or to the terminal side-chain group of an internal lysine analog residue. Lipoamino acids selected from the group consisting of: (i) $Pam_2Cys$ (also known as dipalmitoyl-5-glyceryl-cysteine or S-[2,3-bis(palmitoyloxy)propyl]cysteine), (ii) $Ste_2Cys$ (also known as distearoyl-5-glyceryl-cysteine or S-[2,3-bis (stearoyloxy)propyl]cysteine), $Lau_2Cys$ (also known as dilauroyl-5-glyceryl-cysteine or S-[2,3-bis(lauroyloxy)propyl]cysteine), and $Oct_2Cys$ (also known as dioctanoyl-S-glyceryl-cysteine or S-[2,3-bis(octinoyloxy)propyl]cysteine) are also useful.

As exemplified herein, lipopeptides of the invention directed against influenza virus induced a virus-specific CTL response in the absence of external adjuvant, as reflected by their ability to induce potent CTL-mediated virus clearing responses, to induce CD8+ T cell migration to the lungs and to upregulate the surface expression of MHC class II molecules on immature dendritic cells (DC). The enhanced maturation of dendritic cells following administration of the subject lipopeptides is consistent with enhanced T-helper epitope presentation compared to lipopeptides having N-terminally coupled lipid.

As will be clear to those skilled in the art, the nature of the T-helper and CTL epitopes is not critical in the context of the present invention. The novel approach of attaching the lipid moiety to the epsilon amino group of one or more internal lysine residues or lysine analogue residues within the polypeptide portion of the construct has broad application. Accordingly, based on the results presented herein, it will be understood that a wide range of T-helper and CTL epitopes can be used in the lipopeptide constructs.

BRIEF DESCRIPTION OF THE DRAWINGS

FIG. 1 is a schematic representation showing the generalized structure of the peptide and lipopeptide constructs used in this study. Peptide structures consisted of a $CD4^+$ helper T cell epitope [Th] and a CTL cell epitope [CTL] assembled as tandem linear sequences with a linking internal lysine residue (i.e. [Th]-Lys-[CTL]) or without any internal lysine (i.e. [Th]-[CTL]). Lipopeptides were branched structures wherein a lipid moiety was attached through the epsilon-amino group of a lysine residue, Lys, situated between the two epitopes at the approximate centre of the molecule (i.e. [Th]-Lys($Pam_3Cys$-Ser-Ser)-[CTL]; [Th]-Lys($Pam_2Cys$-Ser-Ser)-[CTL]; or [Th]-Lys($Pam_1Cys$-Ser-Ser)-[CTL]. In the case of branched constructs, the centrally located lysine residue to which the lipid is attached is denoted in italics, Lys. In some cases two serine residues (Ser-Ser) were added between the peptide and lipid moiety. For the lipopeptide Pal$_2$LysLys[Th]-[CTL], two palmitic acid residues were attached to the alpha and epsilon-amino groups of the N-terminal lysine residue and [Th] was attached to the epsilon-amino group of the penultimate lysine in the amino acid sequence. In the case of [Th]-Lys(Chol$_2$Lys-Ser-Ser)-[CTL], two residues of cholesterol were attached to an N-terminal lysine residue.

FIG. 2 is a representation of the primary amino acid sequences of the peptide moieties attached to the lipid moieties for the structures shown in FIG. 1. Non-lipidated peptides comprising these amino acid sequences were designated as follows:

(i) [Th] consisting of a CD4+ T-helper epitope from the light chain of influenza virus hemagglutinin as set forth in SEQ ID NO: 1;

(ii) [CTL] consisting of an immunodominant H-2$^d$-restricted CTL epitope consisting of amino acid residues 147-155 of the nucleoprotein of influenza virus strain A/Puerto Rico/8/34 (PR8; H1N1) as set forth in SEQ ID NO: 2;

(iii) [Th]-[CTL] consisting of a polypeptide having (i) and (ii). The sequence of the assembled peptide is shown in SEQ ID NO: 3;

(iv) [Th]-Lys-[CTL] consisting of a polypeptide having (i) and (ii) separated by a lysine residue (bold underlined residue). The sequence of the assembled peptide is shown in SEQ ID NO: 4;

(v) [P25]-Lys-[SIINFEKL] (SIINFEKL disclosed as SEQ ID NO: 173) consisting of a T-helper epitope from CDV-F protein designated P25 (SEQ ID NO: 20) and a CTL epitope from ovalbumin (SEQ ID NO: 173) separated by a lysine residue (bold underlined residue). The sequence of the assembled peptide is shown in SEQ ID NO: 174;

(vi) [P25]-Lys-[LLO91-99] consisting of a T-helper epitope from CDV-F protein designated P25 (SEQ ID NO: 20) and a CTL epitope from *Listeria monocytogenes* (SEQ ID NO: 172) separated by a lysine residue (bold underlined residue). The sequence of the assembled peptide is shown in SEQ ID NO: 175. And (vii) [P25]-Lys-[HCV] consisting of a T-helper epitope from CDV-F protein designated P25 (SEQ ID NO: 20) and a CTL epitope from the core protein of hepatitis C virus (SEQ ID NO: 176) separated by a lysine residue (bold underlined residue). The sequence of the assembled peptide is shown in SEQ ID NO: 177.

Lipopeptides comprising these amino acid sequences were designated as follows:

(i) [Th]-Lys(Pam$_3$Cys-Ser-Ser)-[CTL] consisting of peptide [Th]-Lys-[CTL] (i.e. SEQ ID NO: 4) and a lipid of the Formula (III) conjugated to the epsilon-amino group of the internal lysine (bold underlined residue);

(ii) [Th]-Lys(Pam$_2$Cys-Ser-Ser)-[CTL] consisting of peptide [Th]-Lys-[CTL] (i.e. SEQ ID NO: 4) and a lipid of the Formula (IV) conjugated to the epsilon-amino group of the internal lysine (bold underlined residue);

(iii) [P25]-Lys(Pam$_2$Cys-Ser-Ser)-[LLO91-99] consisting of peptide [P25]-Lys-[LLO91-99] and a lipid of the Formula (IV) conjugated to the epsilon-amino group of the internal lysine (bold underlined residue) of said peptide;

(iv) [P25]-Lys(Pam$_2$Cys-Ser-Ser)-[SIINFEKL] (SIINFEKL disclosed as SEQ ID NO: 173) consisting of peptide [P25]-Lys-[SIINFEKL] (SIINFEKL disclosed as SEQ ID NO: 173) and a lipid of the Formula (IV) conjugated to the epsilon-amino group of the internal lysine (bold underlined residue) of said peptide; and (v) [P25]-Lys(Pam$_2$Cys-Ser-Ser)-(HCV) consisting of peptide [P25]-Lys-[HCV] and a lipid of the Formula (IV) conjugated to the epsilon-amino group of the internal lysine (bold underlined residue) of said peptide.

Figure 3:
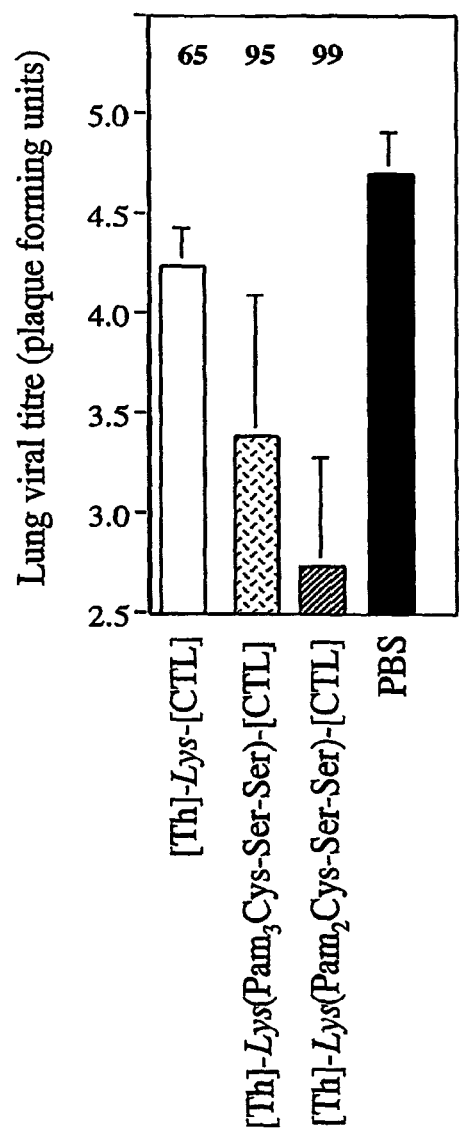

FIG. 3 is a graphical representation showing the reduced viral load of mice primed with lipopeptides referred to in the legend to FIG. 1 and subsequently challenged with influenza virus. Mice were inoculated intranasally with 9 nmol of the lipopeptides [Th]-Lys(Pam$_3$Cys-Ser-Ser)-[CTL] and [Th]-Lys(Pam$_2$Cys-Ser-Ser)-[CTL] in 50 μl PBS (columns 2 and 3, respectively), or for the [Th]-Lys-[CTL] peptide in 50 μl PBS (column 1), or with PBS alone (column 4). Peptide and lipopeptide designations are as for the legend to FIG. 2. On day 9 post immunization, mice were anesthetized using penthrane and challenged intranasally with 30,000 plaque forming units of influenza virus subtype H3N1 known as A/Memphis/1/71 (Mem 71). Five days later, their lungs were removed and assayed for the presence of infectious virus by plaque assay on MDCK cells. Each bar represents the geometric mean titre of viral titres from a group of 5 BALB/c mice and error bars represent the standard deviation of the mean. Numbers above the bars represent the percentage reduction in lung viral titre relative to the PBS control.

Figure 4A:

FIG. 4a is a graphical representation showing enhanced lipopeptide-induced viral clearance in immunized mice receiving the lipopeptides referred to in the legend to FIG. 2. Mice were inoculated with 9 nmoles of the lipopeptides [Th]-Lys(Pam$_3$Cys-Ser-Ser)-[CTL] and [Th]-Lys(Pam$_2$Cys-Ser-Ser)-[CTL] in 50 μl PBS (columns 2 and 3, respectively), or for the [Th]-Lys-[CTL] peptide in 50 μl PBS (column 1), or with PBS alone (column 4). On day 28 post immunization, mice were challenged with 30,000 plaque forming units of Mem 71 virus. Peptide and lipopeptide designations are as for the legend to FIG. 2. Data are expressed as the percentage reduction in lung viral titre on day 5 post challenge. Data show enhanced reduction in infectious virus in the lungs of mice immunized with the lipopeptides [Th]-Lys(Pam$_3$Cys-Ser-Ser)-[CTL] (column 2) or [Th]-Lys(Pam$_2$Cys-Ser-Ser)-[CTL] (column 3) compared to peptide alone (column 1) or PBS alone (column 4) at 5 days post-challenge.

Figure 4B:

FIG. 4b is a graphical representation showing enhanced T cell activation in immunized mice receiving the lipopeptides referred to in the legend to FIG. 2. Mice were inoculated with 9 nmoles of the lipopeptides [Th]-Lys(Pam$_3$Cys-Ser-Ser)-[CTL] and [Th]-Lys(Pam$_2$Cys-Ser-Ser)-[CTL] in 50 μl PBS (columns 2 and 3, respectively), or for the [Th]-Lys-[CTL] peptide in 50 μl PBS (column 1), or with PBS alone (column 4) Immunized mice were killed 9 days post-immunization and a bronchio-alveolar lavage (BAL) performed. Adherent cells were removed by incubation of the BAL sample in a petri dish at 37° C. for 1 hour. The non-adherent cells were recovered and stained for CD8 and CD4 expression. The cells were analyzed by flow cytometry. The lymphocyte population was identified based on the forward and side scatter profile and 10,000 lymphocytes were analysed. Data are expressed as the percentage of non-adherent cells in the BAL fluid that are CD8+ lymphocytes. Data show enhanced activation of virus-specific CD8+ T cells in the BAL samples from mice immunized with the lipopeptides [Th]-Lys(Pam$_3$Cys-Ser-Ser)-[CTL] (column 2) or [Th]-Lys(Pam$_2$Cys-Ser-Ser)-[CTL] (column 3) compared to peptide alone (column 1) or PBS alone (column 4) at 5 days post-challenge. Peptide and lipopeptide designations are as for the legend to FIG. 2.

Figure 4C:
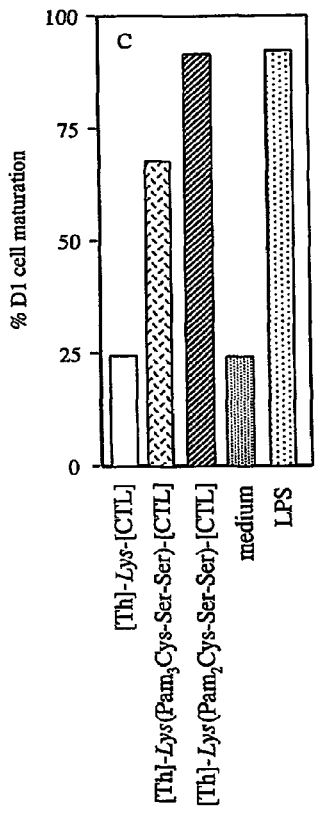

FIG. 4c is a graphical representation showing enhanced maturation of dendritic cells in response to the lipopeptides referred to in the legend to FIG. 2. A line of BALB/c splenic-derived dendritic cells (D1 cells) were incubated overnight with 0.45 nmoles/mL of the peptide [Th]-Lys-[CTL] (column 1) or the lipopeptides lipopeptides [Th]-Lys(Pam$_3$Cys-Ser-Ser)-[CTL] (column 2) or [Th]-Lys(Pam$_2$Cys-Ser-Ser)-[CTL] (column 3) or with medium alone as a negative control (column 4) or lipopolysaccharide as a positive control (LPS; column 5). The percentage of D1 cells expressing high levels of surface MHC class II molecules, and therefore in a mature state, were determined by flow cytometry. Peptide and lipopeptide designations are as for the legend to FIG. 2. Data show enhanced expression of MHC class II molecules on the surface of dendritic cells (ie. enhanced dendritic cell maturation) following exposure to the peptides [Th]-Lys(Pam$_3$Cys-Ser-Ser)-[CTL] or [Th]-Lys(Pam$_2$Cys-Ser-Ser)-[CTL] compared to peptide alone or medium alone.

Figure 5:
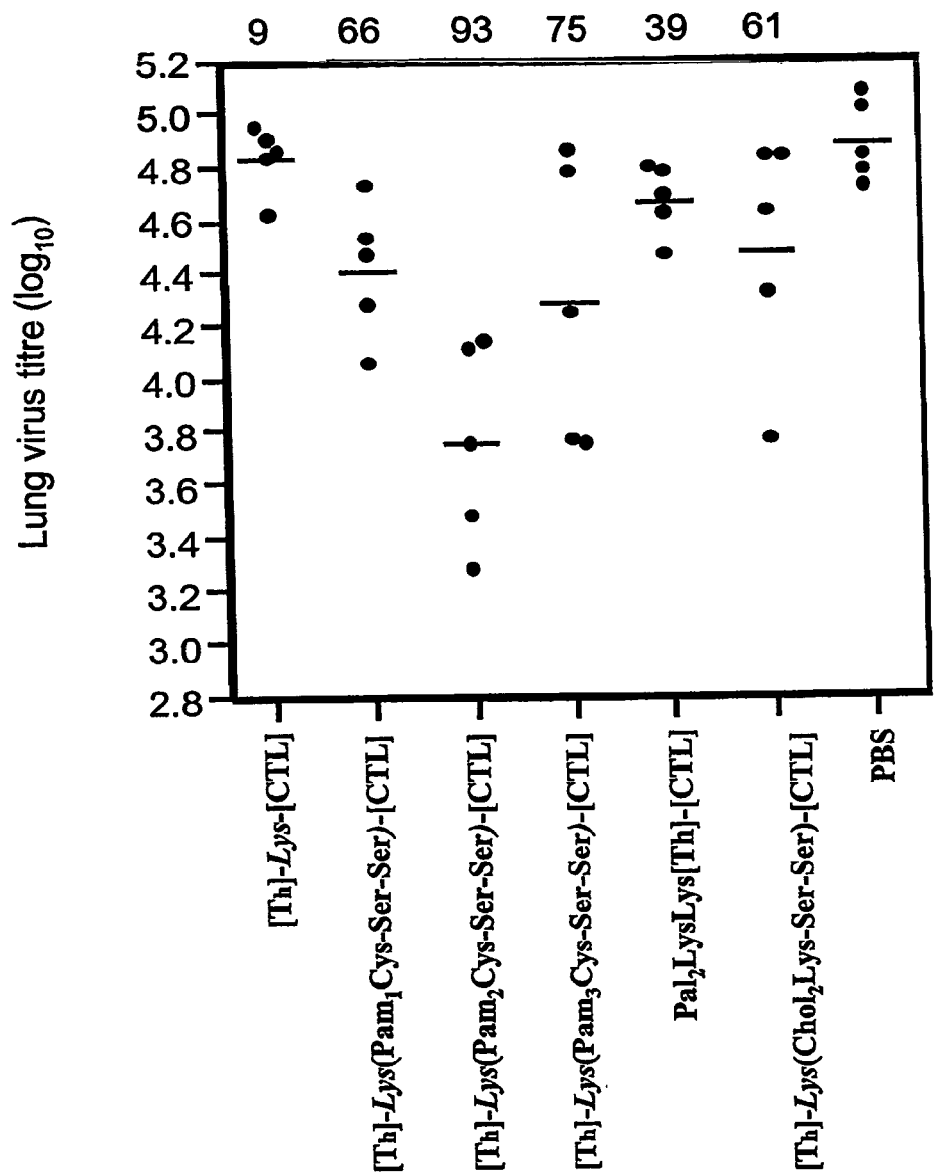

FIG. 5 is a graphical representation showing the induction of pulmonary viral clearing responses in mice inoculated with synthetic immunogens indicated on the x-axis, that each include the CD4$^+$ T-helper epitope set forth in SEQ ID NO: 1 and the H-2$^d$-restricted CTL epitope set forth in SEQ ID NO: 2. Groups of 5 mice were immunised intranasally with 9 nmoles of the specified lipopeptides in PBS. Mice were challenged 28 days after priming with 10$^{4.5}$ PFU of Mem71 influenza virus intranasally. Titres of infectious virus in lung homogenates sampled 5 days following challenge were determined by plaque formation on MDCK cell monolayers. Each circle represents the virus titre of an individual mouse and the line represents the geometric mean titre of the group. The percentage reduction in mean viral titre relative to the PBS control group is shown above each column of data.

Figure 6:
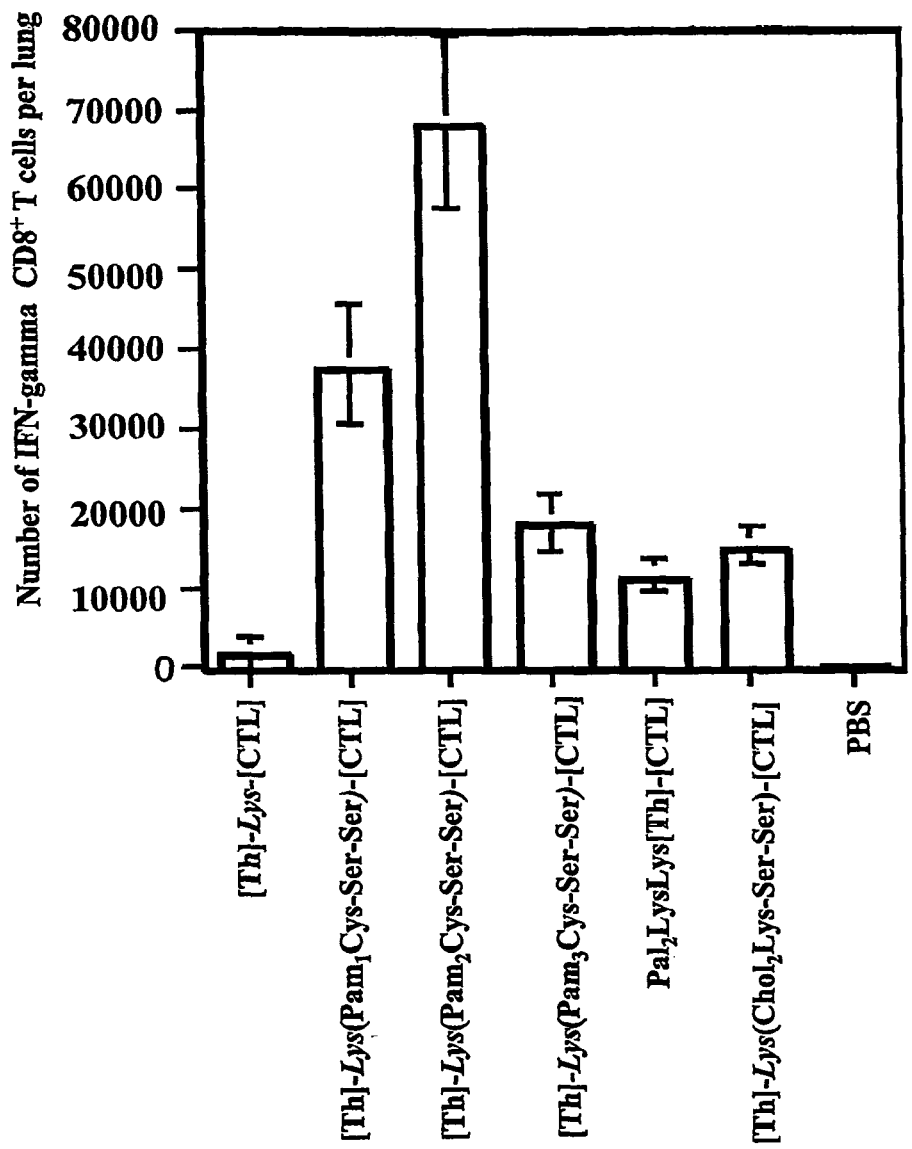

FIG. 6 is a graphical representation showing accelerated influx of CTL derminant-specific CD8$^+$-T cells into the lungs of lipopeptide-vaccinated mice during virus challenge. Lipopeptides comprised the CD4$^+$ T-helper epitope set forth in SEQ ID NO: 1 and the H-2$^d$-restricted CTL epitope set forth in SEQ ID NO: 2. Groups of three mice were inoculated intranasally with 9 nmole of the indicated lipopeptides intranasally. On day 28 post priming, they were challenged intranasally with 10$^{4.5}$ PFU of Mem71 influenza virus intranasally. CTL determinant-specific IFN-gamma-secreting cells were enumerated in the lungs of mice on day 5 post-challenge by an intracellular cytokine production assay. 10,000 CD8+ cells were analysed for each sample. Data represent the mean and standard deviation for each group of mice.

Figure 7:
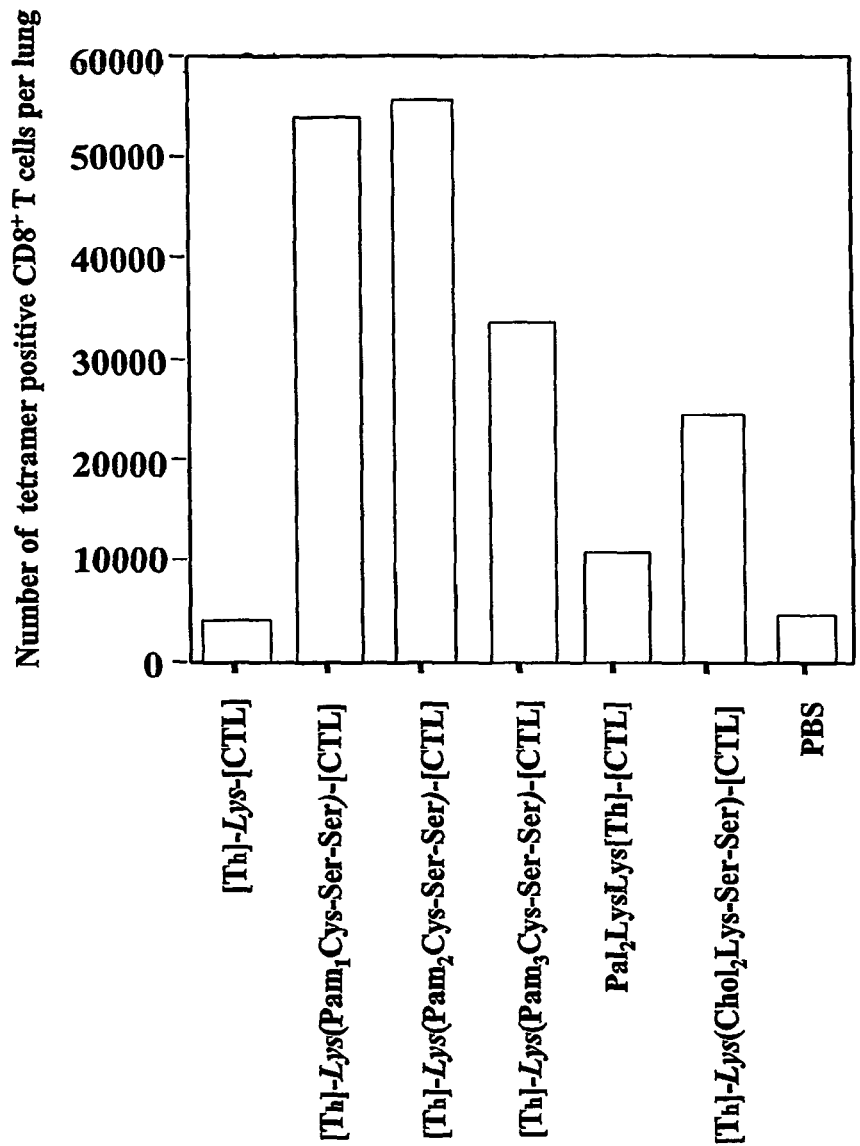

FIG. 7 is a graphical representation showing show accelerated influx of CTL-determinant-specific CD8 T cells into the lungs in mice inoculated with lipopeptides following viral challenge. Lipopeptides comprised the CD4$^+$ T-helper epitope set forth in SEQ ID NO: 1 and the H-2$^d$-restricted CTL epitope set forth in SEQ ID NO: 2. Mice were inoculated intranasally with 9 nmole of the specified lipopeptides in PBS. Nine days after inoculation mice were challenged intranasally with 10$^{4.5}$ PFU of Mem71 influenza virus. On day 5 post infection, CTL-determinant-specific CD8 T cells in the lungs were enumerated by staining the lymphocytes from the lungs with anti-CD8 antibody and with tetrameric MHC class I complexes loaded with the CTL epitope. A total of 30,000 CD8 T cells were analysed.

Figure 8:
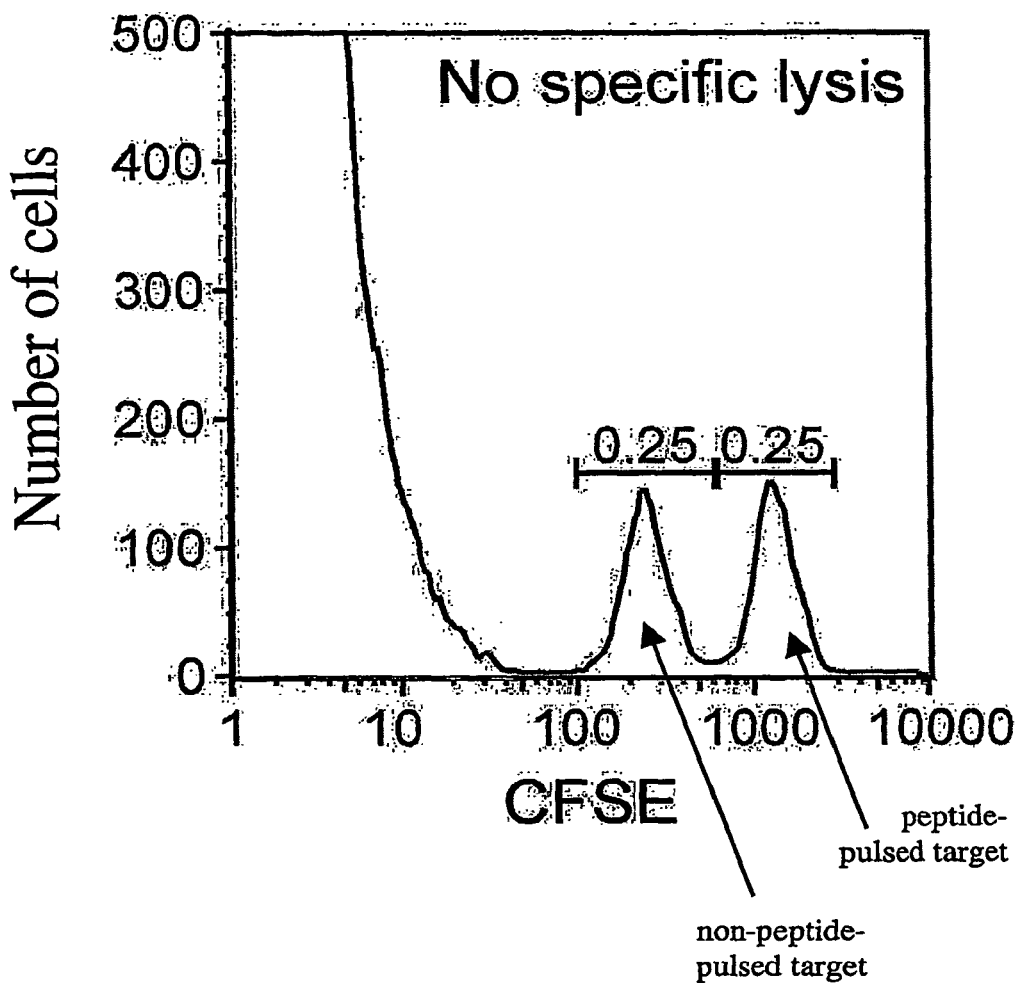

FIG. 8 is a graphical representation showing cytotoxic T cell activity in naïve mice. CTL determinant specific cytotoxicity in vivo was measured using syngeneic spleen cells pulsed with the CTL determinant and labelled with high intensity CFSE. Non-pulsed spleen cells labelled with low intensity CFSE were used as a control. A mixture of 15×10$^6$ cells of each target cell population was injected intravenously on day 4 post-infection into naïve mice. The mice were killed 16 hr later and spleens were analysed for the presence of CFSE-high and CFSE-low cell populations by flow cytometry. A total of 1×10$^6$ lymphocytes were analysed for each sample.

Figure 9:
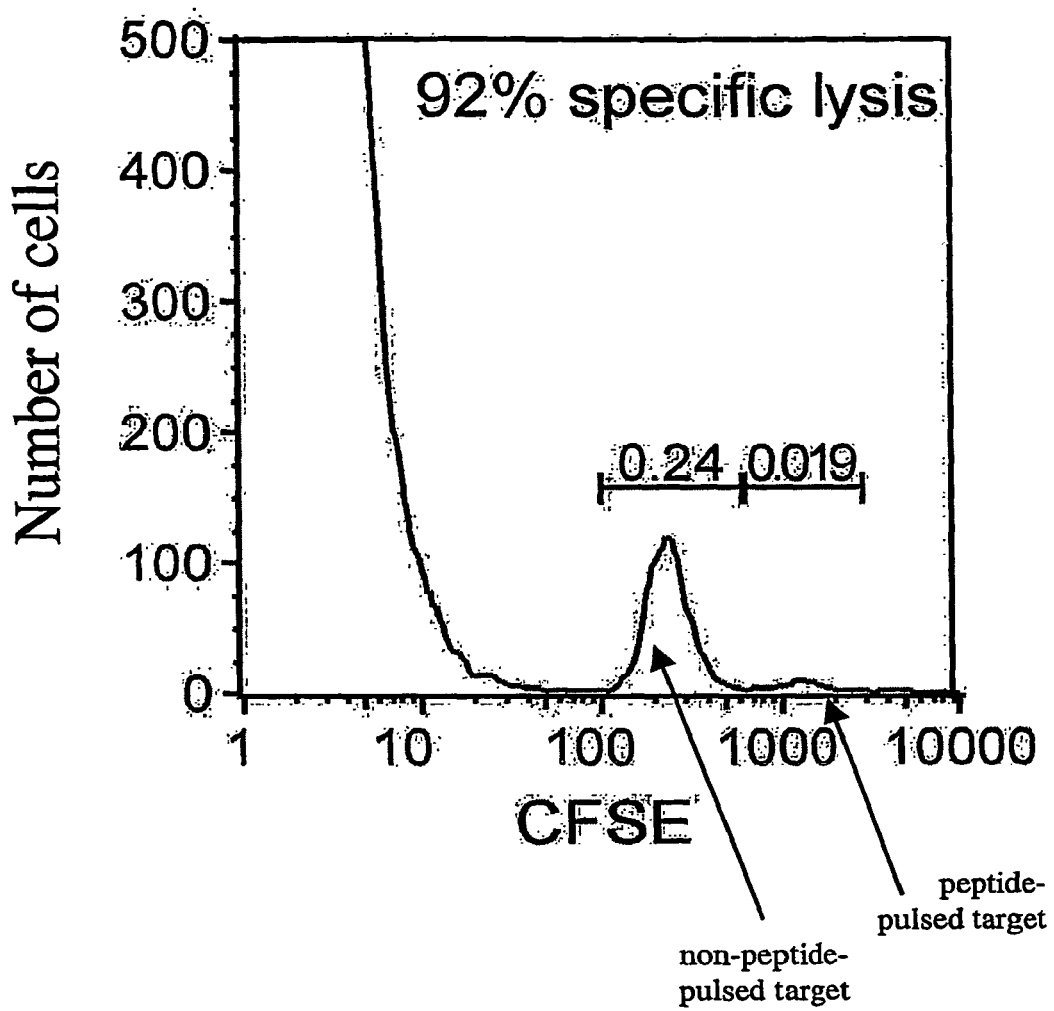

FIG. 9 is a graphical representation showing cytotoxic T cell activity in lipopeptide-primed mice. A mouse was inoculated intranasally with 9 nmoles [TN-Lys(Pam$_2$Cys-Ser-Ser)-[CTL] comprising the CD4$^+$ T-helper epitope set forth in SEQ ID NO: 1 and the H-2$^d$-restricted CTL epitope set forth in SEQ ID NO: 2, in PBS. Mice were challenged with Mem71 on day 28. CTL determinant specific cytotoxicity in vivo was measured using syngeneic spleen cells pulsed with the CTL determinant and labelled with high intensity CFSE. Non-pulsed spleen cells labelled with low intensity CFSE were used as a control. A mixture of 15×10$^6$ cells of each target cell population was injected intravenously on day 4 post-infection into the lipopeptide-primed and challenged mice. The mice were killed 16 hr later and spleens were analysed for the presence of CFSE-high and CFSE-low cell populations by flow cytometry. A total of 1×10$^6$ lymphocytes were analysed for each sample.

Figure 10:
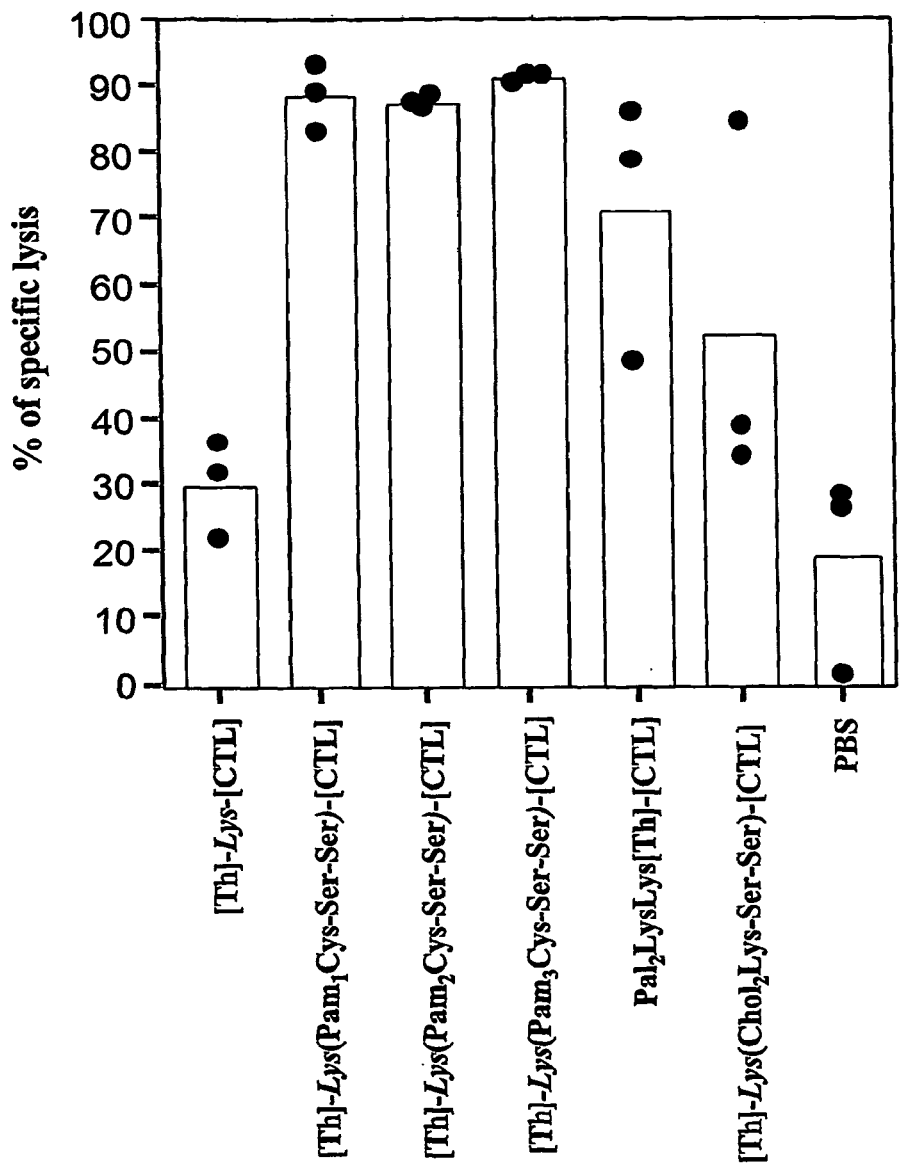

FIG. 10 is a graphical representation showing the ability of various peptide-based immunogens to induce epitope-specific CTL. Lipopeptides comprised the CD4$^+$ T-helper epitope set forth in SEQ ID NO: 1 and the H-2$^d$-restricted CTL epitope set forth in SEQ ID NO: 2. Groups of three mice were inoculated intranasally with various lipopeptides in PBS and challenged with Mem71 on day 28. In order to analyze CTL determinant specific cytotoxicity in vivo, syngeneic spleen cells were pulsed with the CTL determinant and labelled with high intensity CFSE. Antigen-specific lysis was controlled by co-injecting syngeneic spleen cells labelled with low intensity CFSE. A mixture of 15×10$^6$ cells of each target cell population was injected intravenously on day 4 post-infection. The mice were killed 16 hr later and spleens were analysed for the presence of CFSE-high and CFSE-low cell populations by flow cytometry. A total of 1×10$^6$ lymphocytes were analysed for each sample. Individual mice are represented by the closed squares and the bars represent the geometric mean titre.

Figure 11:
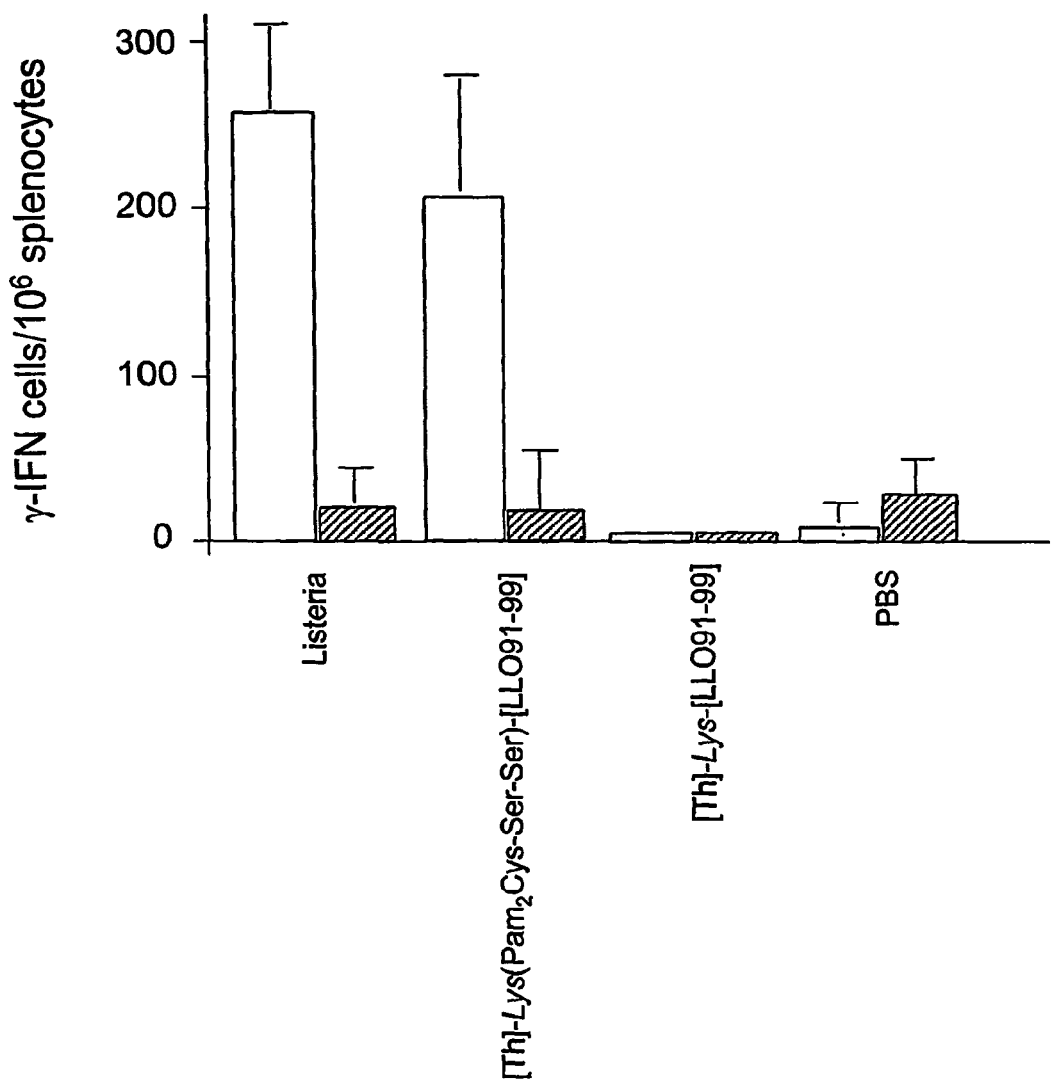

FIG. 11 is a graphical representation showing induction of interferon-gamma producing cells by lipopeptide. Peptide comprising a T-helper epitope and a CTL epitope of *Listeria monocytogenes* linked via the epsilon amino group of an internal lysine residue positioned between said epitopes to Pam$_2$Cys (i.e. the peptide [P25]-Lys(Pam$_2$Cys-Ser-Ser)-[LLO91-99] listed in FIG. 2 and based upon SEQ ID NO: 175), or lipopeptide(s) based on this structure in which Pam$_2$Cys was linked through the epsilon amino group of said lysine, were used to inoculate mice. Five BALB/c mice were inoculated intravenously with bacteria, or subcutaneously with either 9 nmoles of lipidated peptide [P25]-Lys(Pam$_2$Cys-Ser-Ser)-[LLO91-99] or 9 nmoles of non-lipidated peptide [P25]-Lys-[LLO91-99] (SEQ ID NO: 175; FIG. 2) or phosphate buffered saline (PBS), as indicated on the x-axis. Splenocytes were obtained from the immunized animals and stimulated in vitro with either the isolated CTL epitope having the sequence set forth in SEQ ID NO: 172 (open bars) or no antigen (filled bars), and the number of (IFN-gamma) producing cells present was measured 28 days later. The ordinate indicates the number of IFN-gamma producing cells per 1,000,000 splenocytes. Data show enhanced numbers of IFN-gamma producing cells for mice immunized with lipopeptide, indicating an enhanced ability of the lipopeptides to activate T cells relative to non-lipidated peptide.

Figure 12:
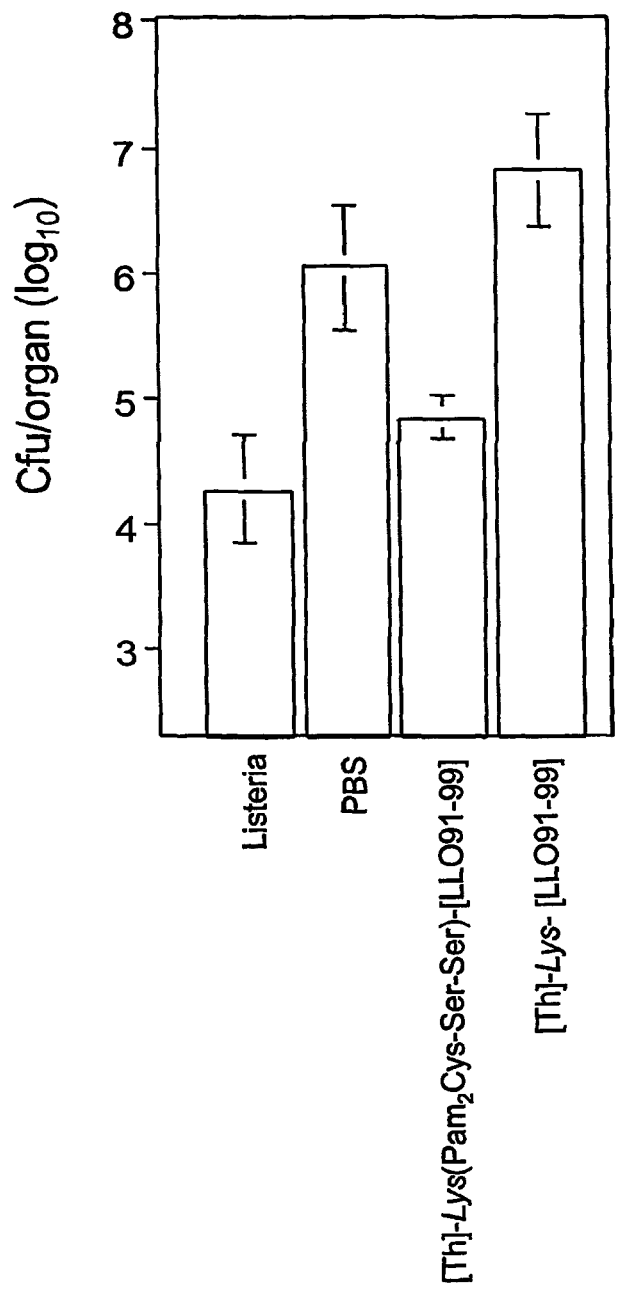

FIG. 12 is a graphical representation showing enhanced protection against *L. monocytogenes* infection for mice immunized with the lipopeptide designated [P25]-Lys (Pam₂Cys-Ser-Ser)-[LLO91-99] in FIG. 2 (based upon SEQ ID NO: 175). Five 5 BALB/c mice were inoculated intravenously with 1,000 bacteria (column 1), or immunized subcutaneously with PBS (column 2) or 9 nmol [P25]-Lys (Pam₂Cys-Ser-Ser)-[LLO91-99] peptide (column 3) or 9 nmol non-lipidated [P25]-Lys-[LLO91-99] peptide (SEQ ID NO: 175; column 4), as indicated on the x-axis. Mice were challenged with whole bacteria and the number of colony forming units present in liver was measured 28 days post-challenge (ordinate).

Figure 13:
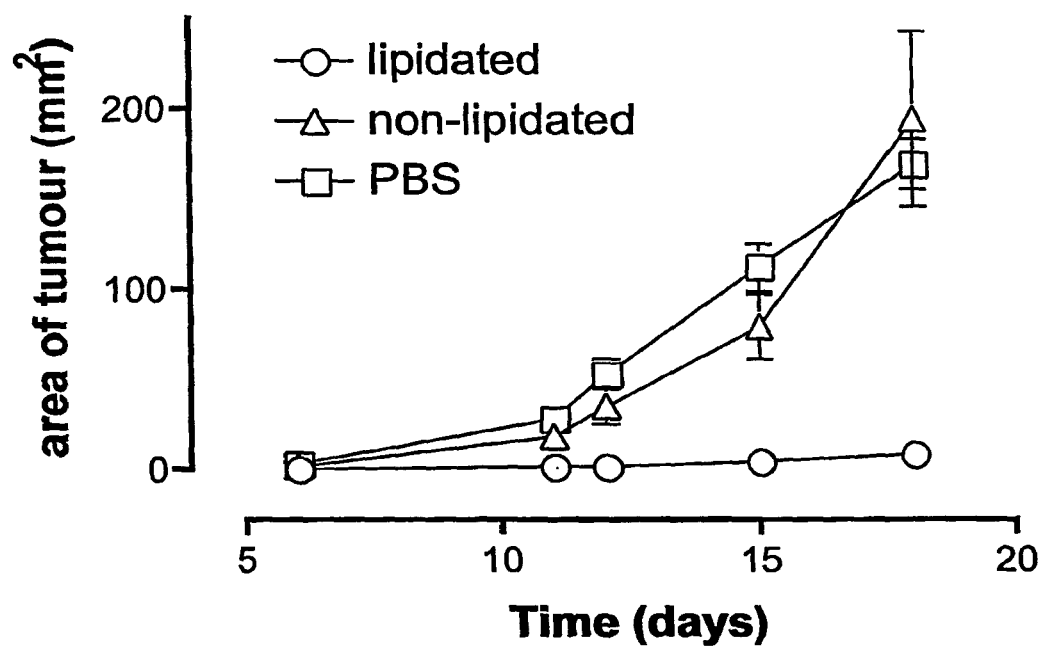

FIG. 13 is a graphical representation showing protection against B16 melanoma with lipopeptide vaccination. C57BL/6 mice were vaccinated with 20 nmoles lipidated peptide [P25]-Lys(Pam₂Cys-Ser-Ser)-[SIINFEKL](SIINFEKL disclosed as SEQ ID NO: 173) (open circles), non-lipidated peptide [P251-Lys-[SIINFEKL] (SIINFEKL disclosed as SEQ ID NO: 173) (open triangles) or with PBS (open squares) subcutaneously in the base of the tail. Mice were then challenged s.c. on the back 14 days later with 2×10⁵ B16-OVA cells (n=6 per group) and tumour growth monitored as described (Anraku, et al., *J. Virol.* 76; 3791-3799, 2002).

Figure 14:
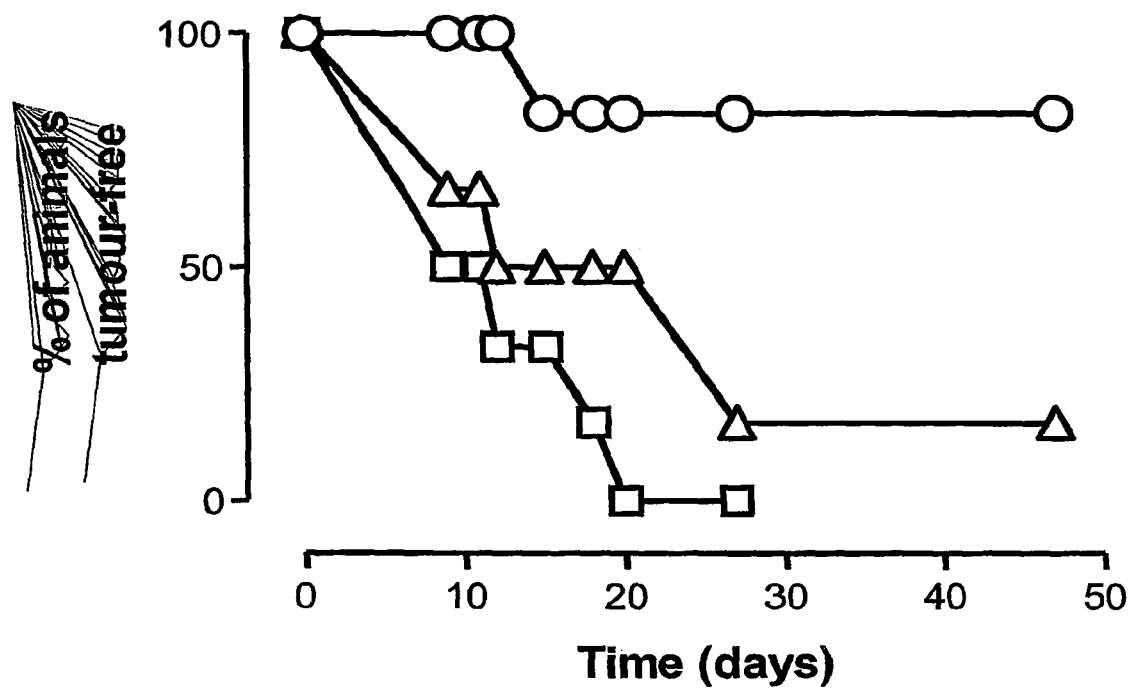

FIG. 14 is a graphical representation showing therapeutic treatment of Lewis Lung tumour with a lipopeptide immunogen, as determined by the percentage of animals that remain tumor free following immunization. Mice were injected with 3×10⁴ Lewis Lung tumour cells that had been transfected with ovalbumin and therefore expressed the CTL epitope SIINFEKL (SEQ ID NO: 173) [Nelson et al., *J Immunol.* 166: 5557-5566, 2001]. Four days after receiving tumour cells, animals were inoculated with 20 nmoles lipidated peptide [P25]-Lys(Pam₂Cys-Ser-Ser)-[SIINFEKL] (SIINFEKL disclosed as SEQ ID NO: 173) (open circles), non-lipidated peptide [P25]-Lys-[SIINFEKL] (SIINFEKL disclosed as SEQ ID NO: 173) (open triangles) or with PBS (open squares) subcutaneously in the base of the tail. A second and similar dose of immunogen was administered eleven days after receiving the tumour cells. Animals were monitored for tumour incidence; animals were euthanased when tumour area exceeded 100 mm².

Figure 15:
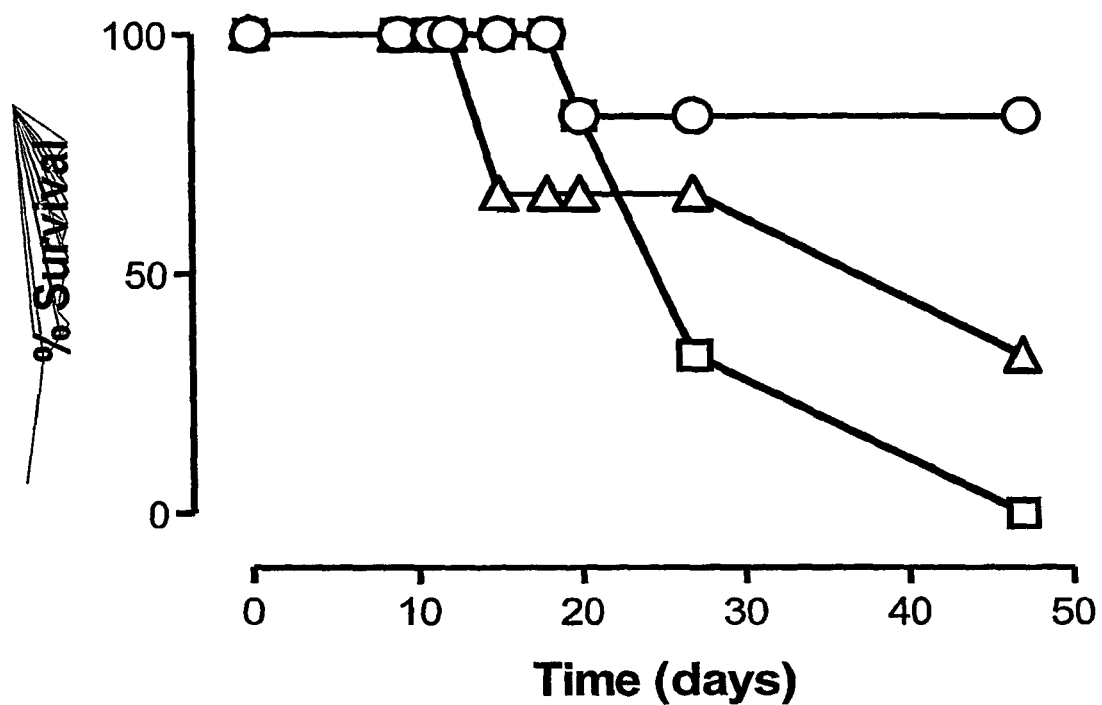

FIG. 15 is a graphical representation showing therapeutic treatment of Lewis Lung tumour with a lipopeptide immunogen, as determined by measuring survival of animals following immunization. Mice were injected with 3×10⁴ Lewis Lung tumour cells that had been transfected with ovalbumin and therefore expressed the CTL epitope SIINFEKL (SEQ ID NO: 173) [Nelson et al., *J. Immunol.* 166: 5557-5566, 2001]. Four days after receiving tumour cells, animals were inoculated with 20 nmoles lipidated peptide [P25]-Lys(Pam₂Cys-Ser-Ser)SIINFEKL] (SIINFEKL disclosed as SEQ ID NO: 173) (open circles), non-lipidated peptide [P25]-Lys-[SIINFEKL] (SIINFEKL disclosed as SEQ ID NO: 173) (open triangles) or with PBS (open squares) subcutaneously in the base of the tail. A second and similar dose of immunogen was administered eleven days after receiving the tumour cells. Animals were monitored for survival; animals were euthanased when tumour area exceeded 100 mm².

Figure 16:
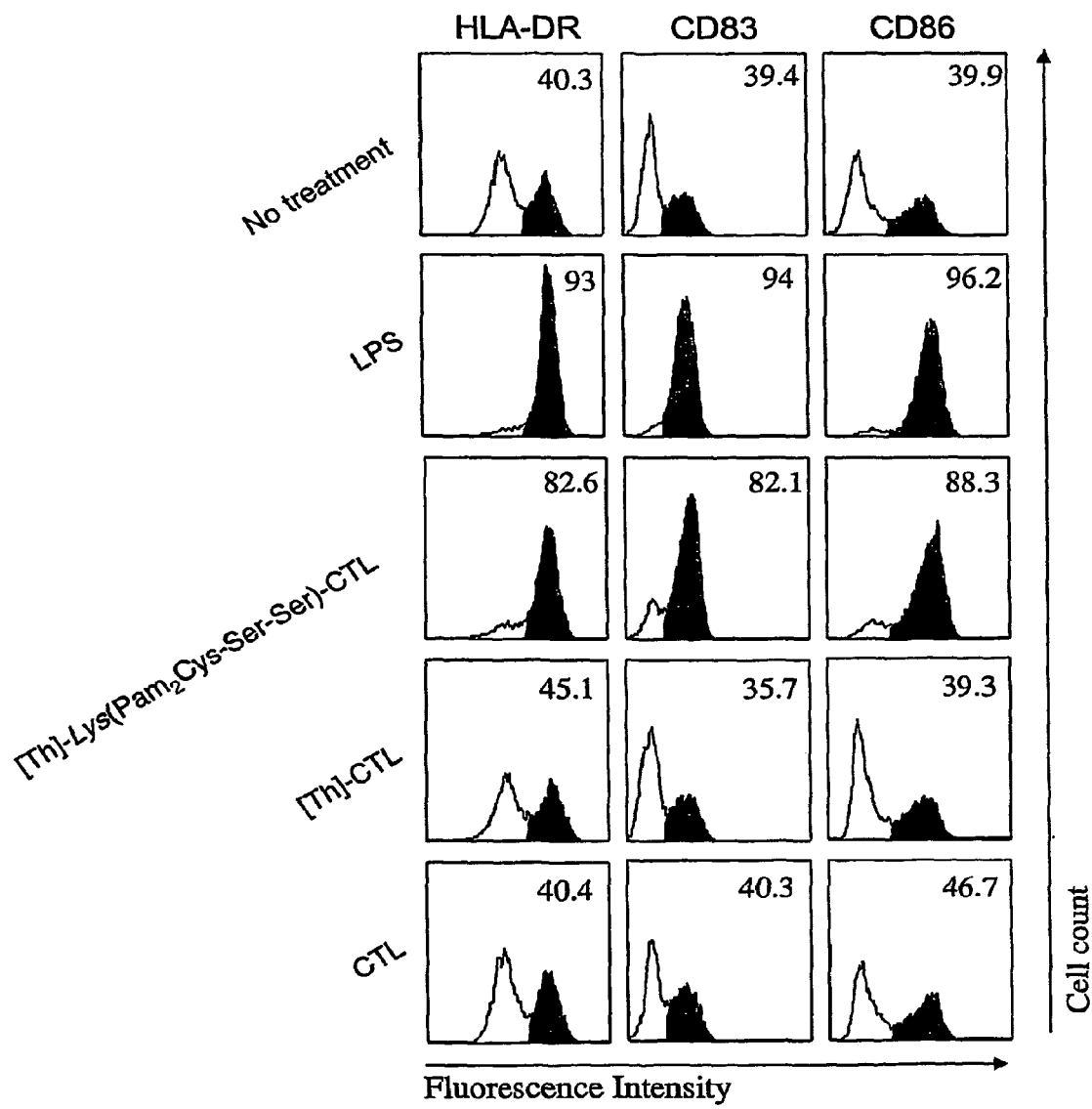

FIG. 16 is a graphical representation showing the ability of peptide and lipopeptide-based immunogens to up-regulate the expression of MHC class II, CD83 and CD86 on human dendritic cells. Human monocyte-derived dendritic cells were incubated with media alone, LPS (5 pg/mL), non-lipidated peptide [P25]-Lys-[HCV] (5 μg/mL) or lipopeptide [P25]-Lys(Pam₂Cys-Ser-Ser)-[HCV] (5 μg/mL) for 48 hours before staining with FITC-conjugated antibodies for HLA-DR, CD83 and CD86 before analysis by flow cytometry. Histograms are representative, of live large granular cells gated on the forward and side scatter dot plot. Regions of histograms shaded in grey and the given values correspond to the percentage of cells that express high levels of antigen within the analysed populations. The T helper cell epitope was identified from Mobillivirus and has the amino acid sequence KLIPNASLIENCTKAEL (SEQ ID NO: 20); the CTL epitope with the amino acid sequence DLMGYIPLV (SEQ ID NO: 176) is an HLA A2-restricted CTL epitope from the core protein of hepatitis C virus.

DETAILED DESCRIPTION OF THE PREFERRED EMBODIMENTS

Lipopeptides

One aspect of the invention provides an isolated lipopeptide comprising a polypeptide conjugated to one or more lipid moieties wherein:
(i) said polypeptide comprises an amino acid sequence that comprises:
 (a) the amino acid sequence of a T helper cell (Th) epitope and the amino acid sequence of a CTL epitope, wherein said amino acid sequences are different; and
 (b) one or more internal lysine residues or internal lysine analog residues for covalent attachment of each of said lipid moieties via the epsilon-amino group or terminal side-chain group of said lysine or lysine analog; and
(ii) each of said one or more lipid moieties is covalently attached directly or indirectly to an epsilon-amino group of said one or more internal lysine residues or to a terminal side-chain group of said internal lysine analog residues.

As used herein, the term "lipopeptide" means any non-naturally occurring composition of matter comprising one or more lipid moieties and one or more amino acid sequences that are directly or indirectly conjugated, said composition of matter being substantially free of conspecific non-conjugated lipid or protein.

By "directly" means that a lipid moiety and an amino acid sequence are juxtaposed in said lipopeptide (i.e. they are not separated by a spacer molecule).

By "indirectly" means that a, lipid moiety and an amino acid sequence are separated by a spacer comprising one or more carbon-containing molecules, such as, for example, one or more amino acid residues. The amino acid sequence may be of any length, constrained by the requirement for functionality of both the T-helper epitope and the CTL epitope.

As used herein, the term "internal lysine residue" means a lysine residue in the polypeptide comprising both the T-helper epitope and the CTL epitope, wherein said lysine is not the N-terminal amino acid residue or the C-terminal residue of said polypeptide. Accordingly, the internal lysine residue may be a C-terminal or N-terminal residue of either the T-helper epitope or the CTL epitope, provided that it is internalized in the polypeptide. This means that the internal lysine residue to which the lipid moiety is attached is a residue that is present in the amino acid sequence of the T helper cell epitope or the amino acid sequence of the CTL epitope. The internal lysine residue may also be distinct from the T-helper epitope or the CTL epitope, in which case it must link these two epitopes of the polypeptide.

Similarly, the term "internal lysine analog residue" means a lysine analog residue in the polypeptide comprising both the T-helper epitope and the CTL epitope, wherein said lysine analog is not the N-terminal amino acid residue or the C-terminal residue of said polypeptide. The criteria for establishing whether or not a lysine residue is "internal" shall apply mutatis mutandis to determining whether or not a lysine analog is internal.

By "lysine analog" is meant a synthetic compound capable of being incorporated into the internal part of a peptide that has a suitable side-group to which the lipid moiety can be coupled, including an amino acid analog or non-naturally occurring amino acid having such an amino side group. Preferred lysine analogs include compounds of the following general Formula (V):

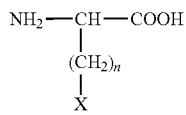

wherein n is an integer from 0 to 3 and wherein X is a terminal side-chain group of said internal lysine analog residue selected from the group consisting of NH, O and S. More preferably, n is an integer having a value from 1 to 3. More preferably, X is an amino group. In a particularly preferred embodiment, the lysine analog is selected from the group consisting of 2,3 diaminopropionic acid (Dpr), 2,4-diaminobutyric acid (Dab) and 2,5-diaminovaleric acid [i.e. ornithine (Om)].

Those skilled in the art will know the meaning of the term "epsilon-amino group". The term "terminal side-chain group" means a substituent on the side chain of a lysine analog the is distal to the alpha-carbon of said analog, such as, for example, a beta-amino of Dpr, gamma-amino of Dab, or delta-amino of Om.

Preferably, the lipid moiety is attached via the epsilon amino group of a lysine residue or to a terminal side-chain group of said internal lysine analog residue that is positioned between the amino acid sequences of the T helper epitope and the CTL epitope.

The enhanced ability of the lipopeptides of the invention to elicit a T cell response is reflected by their ability to upregulate the surface expression of MHC class II molecules on immature dendritic cells (DC), particularly D1 cells, and by the enhanced number of $CD8^+$ T cells in tissue samples of immunized animals. In the case of animals immunized using CTLs of a viral pathogen, the enhanced ability of the lipopeptides of the invention to elicit a T cell response is also indicated by the enhanced viral clearance following immunization of animals.

Preferably, the lipopeptides are soluble, more preferably highly soluble.

As will be known to those skilled in the art, the epsilon amino group of lysine is the terminal amino group of the side chain of this amino acid. Use of the terminal side-chain group of the internal lysine or internal lysine analog for cross-linkage to the lipid moiety facilitates the synthesis of the polypeptide moiety as a co-linear amino acid sequence incorporating both the T-helper epitope and the CTL epitope. There is a clear structural distinction between a lipopeptide having lipid attached via the epsilon amino group of a lysine residue or the terminal side-chain group of a lysine analog, and a lipopeptide having the lipid attached via an alpha amino group of a lysine in the peptide.

Accordingly, it is particularly preferred for at least one internal lysine residue or internal lysine analog to which the lipid moiety is attached to be positioned within the polypeptide moiety so as to separate the immunologically-functional epitopes. For example, the internal lysine residue or internal lysine analog may act as a spacer and/or linking residue between the epitopes. Naturally, wherein the internal lysine or internal lysine analog is positioned between the T-helper epitope and the CTL epitope, the lipid moiety will be attached at a position that is also between these epitopes, albeit forming a branch from the amino acid sequence of the polypeptide. As exemplified herein, a single internal lysine residue is used to separate CTL and T-helper epitopes (eg. SEQ ID No: 4).

The present invention clearly contemplates the nesting of the internal lysine residue or internal lysine analog residue within a third amino acid sequence that does not function as a CTL epitope or T-helper epitope. For example, the internal lysine or internal lysine analog may be conjugated to one or more different amino acid residues.

The epsilon amino group of the internal lysine or terminal side-chain group of an internal lysine analog can be protected by chemical groups which are orthogonal to those used to protect the alpha-amino and side-chain functional groups of other amino acids. In this way, the epsilon amino group or other side-chain group of an internal lysine or lysine analog can be selectively exposed to allow attachment of chemical groups, such as lipid-containing moieties, specifically to the epsilon amino group or side-chain amino group, as appropriate.

For peptide syntheses using Fmoc chemistry, a suitable orthogonally protected epsilon group of lysine is provided by the modified amino acid residue Fmoc-Lys(Mtt)-OH (Nα-Fmoc-Nε-4-methyltrityl-L-lysine). Similar suitable orthogonally-protected side-chain groups are available for various lysine analogs contemplated herein, eg. Fmoc-Om(Mtt)-OH (Nα-Fmoc-Nδ-4-methyltrityl-L-Ornithine), Fmoc-Dab(Mtt)-OH (Nα-Fmoc-Nγ4-methyltrityl-L-diaminobutyric acid) and Fmoc-Dpr(Mtt)-OH (Nα-Fmoc-Nβ-4-methyltrityl-L-diaminopropionic acid). The side-chain protecting group Mtt is stable to conditions under which the Fmoc group present on the alpha amino group of lysine or a lysine analog is removed but can be selectively removed with 1% trifluoroacetate acid in dichloromethane. Fmoc-Lys(Dde)-OH (Nα-Fmoc-Nε-1-(4,4-dimethyl-2,6-dioxocyclohex-1-ylidene) ethyl-L-lysine) or Fmoc-Lys(ivDde)-OH (Nα-Fmoc-Nε-1-(4,4-dimethyl-2,6-dioxocyclohex-1-ylidene)-3-methylbutyl-L-lysine) can also be used in this context, wherein the Dde side-chain protecting groups is selectively removed during peptide synthesis by treatment with hydrazine.

For peptide syntheses using Boc chemistry, Boc-Lys (Fmoc)-OH can be used. The side-chain protecting group Fmoc can be selectively removed by treatment with piperidine or DBU (1,8-Diazabicyclo[5.4.0]undec-7-ene) but remain in place when the Boc group is removed from the alpha terminus using trifluoroacetic acid.

Preferably, the T helper epitope and CTL epitope are separated by at least one or two or three or four or five amino acid residues including a single internal lysine residue or internal lysine analog residue.

The present invention clearly contemplates the addition of multiple lipid moieties to the polypeptide moiety. For example, the polypeptide may include multiple internal lysine residues and/or multiple internal lysine analogs. Steric hindrance may occur in the addition of lipid if multiple internal lysines or multiple lysine analogs are positioned more closely together, thereby producing a mixture of end-products, or a reduced yield.

Relevant to this consideration is the fact that it is not necessary for the entire amino acid sequence comprising the T-helper epitope or the entire amino acid sequence comprising the CTL epitope to have an immune function. Accordingly, the said amino acid sequences, whilst comprising said epitopes may have additional sequence not possessing T-helper cell activity or a CTL epitope. Where such additional sequences include one or more internal lysine or lysine analog residues, the terminal side-chain groups of such residues may serve as attachment sites for the lipid moiety. Naturally, it is essential to retain both T-helper function and CTL epitope function.

The positioning of the internal lysine residue or internal lysine analog for attachment of the lipid moiety should also be selected such that attachment of the lipid moiety does not interfere with the immune function of the T-helper epitope or the CTL epitope in a subject to whom the lipopeptide is administered. For example, depending upon the selection of lipid moiety, the attachment of said lipid within the CTL epitope may sterically hinder CTL epitope presentation.

A generalized preferred form of the lipopeptide of the invention, wherein the internal lysine or internal lysine analog is positioned between the T-helper and CTL epitopes is provided by the general Formula (VI).

Formula (VI):

```
[epitope]—A—NH—CH—CO—A—[epitope]
              |
            (CH₂)ₙ
              |
              X
              |
              Y
              |
              Z
``` wherein:
epitope is a T-helper epitope or CTL epitope;
A is either present or absent and consists of an amino acid spacer of about 1 to about 6 amino acids in length;
n is an integer having a value of 1, 2, 3, or 4;
X is a terminal side-chain group selected from the group consisting of NH, O and S and preferably consisting of NH;
Y is either present of absent and consists of an amino acid spacer of about 1 to about 6 amino acids in length, wherein it is preferred for said amino acid to be serine; and
Z is a lipid moiety, preferably Pam$_2$Cys or Pam$_3$Cys.

The T-helper epitope is any T-helper epitope known to the skilled artisan for enhancing an immune response in a particular target subject (i.e. a human subject, or a specific non-human animal subject such as, for example, a rat, mouse, guinea pig, dog, horse, pig, or goat). Preferred T-helper epitopes comprise at least about 10-24 amino acids in length, more generally about 15 to about 20 amino acids in length.

Promiscuous or permissive T-helper epitopes are particularly preferred as these are readily synthesized chemically and obviate the need to use longer polypeptides comprising multiple T-helper epitopes.

Examples of promiscuous or permissive T-helper epitopes suitable for use in the lipopeptides of the present invention are selected from the group consisting of:
(i) a rodent or human T-helper epitope of tetanus toxoid peptide (TTP), such as, for example amino acids 830-843 of TTP (Panina-Bordignon et al., *Eur. J. Immun.* 19, 2237-2242, 1989);
(ii) a rodent or human T-helper epitope of *Plasmodium falciparum* pfg27;
(iii) a rodent or human T-helper epitope of lactate dehydrogenase;
(iv) a rodent or human T-helper epitope of the envelope protein of HIV or HIVgp120 (Berzofsky et al., *J. Clin. Invest.* 88, 876-884, 1991);
(v) a synthetic human T-helper epitope (PADRE) predicted from the amino acid sequence of known anchor proteins (Alexander et al., *Immunity* 1, 751-761, 1994);
(vi) a rodent or human T-helper epitope of measles virus fusion protein (MV-F; Muller et al., *Mol. Immunol.* 32, 37-47, 1995; Partidos et al., *J. Gen. Virol.*, 71, 2099-2105, 1990);
(vii) a T-helper epitope comprising at least about 10 amino acid residues of canine distemper virus fusion protein (CDV-F) such as, for example, from amino acid positions 148-283 of CDV-F (Ghosh et al., *Immunol.* 104, 58-66, 2001; International Patent Publication No. WO 00/46390);
(viii) a human T-helper epitope derived from the peptide sequence of extracellular tandem repeat domain of MUC1 mucin (US Patent Application No. 0020018806);
(ix) a rodent or human T-helper epitope of influenza virus hemagglutinin (IV-H) (Jackson et al. *Virol.* 198, 613-623, 1994); and
(x) a bovine or camel T-helper epitope of the VP3 protein of foot and mouth disease virus (FMDV-01 Kaufbeuren strain), comprising residues 173 to 176 of VP3 or the corresponding amino acids of another strain of FMDV.

As will be known to those skilled in the art, a T-helper epitope may-be recognised by one or more mammals of different species. Accordingly, the designation of any T-helper epitope herein is not to be considered restrictive with respect to the immune system of the species in which the epitope is recognised. For example, a rodent T-helper epitope can be recognised by the immune system of a mouse, rat, rabbit, guinea pig, or other rodent, or a human or dog.

More preferably, the T-helper epitope will comprise an amino acid sequence selected from the group consisting of:

| | | |
|---|---|---|
| (i) | ALNNRFQIKGVELKS from IV-H; | (SEQ ID NO: 1) |
| (ii) | GALNNRFQIKGVELKS from IV-H; | (SEQ ID NO: 14) |
| (iii) | LSEIKGVIVHRLEGV from MV-F; | (SEQ ID NO: 15) |
| (iv) | TAAQITAGIALHQSNLN from CDV-F; | (SEQ ID NO: 16) |
| (v) | IGTDNVHYKIMTRPSHQ from CDV-F; | (SEQ ID NO: 17) |
| (vi) | YKIMTRPSHQYLVIKLI from CDV-F; | (SEQ ID NO: 18) |
| (vii) | SHQYLVIKLIPNASLIE from CDV-F; | (SEQ ID NO: 19) |
| (viii) | KLIPNASLIENCTKAEL from CDV-F; | (SEQ ID NO: 20) |
| (ix) | LIENCTKAELGEYEKLL from CDV-F; | (SEQ ID NO: 21) |
| (x) | AELGEYEKLLNSVLEPI from CDV-F; | (SEQ ID NO: 22) |
| (xi) | KLLNSVLEPINQALTLM from CDV-F; | (SEQ ID NO: 23) |
| (xii) | EPINQALTLMTKNVKPL from CDV-F; | (SEQ ID NO: 24) |

-continued

```
(xiii)      TLMTKNVKPLQSLGSGR from CDV-F;           (SEQ ID NO: 25)

(xiv)       KPLQSLGSGRRQRRFAG from CDV-F;           (SEQ ID NO: 26)

(xv)        SGRRQRRFAGVVLAGVA from CDV-F;           (SEQ ID NO: 27)

(xvi)       FAGWLAGVALGVATAA from CDV-F;            (SEQ ID NO: 28)

(xvii)      GVALGVATAAQITAGIA from CDV-F;           (SEQ ID NO: 29)

(xviii)     GIALHQSNLNAQAIQSL from CDV-F;           (SEQ ID NO: 30)

(xix)       NLNAQAIQSLRTSLEQS from CDV-F;           (SEQ ID NO: 31)

(xx)        QSLRTSLEQSNKAIEEI from CDV-F;           (SEQ ID NO: 32)

(xxi)       EQSNKAIEEIREATQET from CDV-F;           (SEQ ID NO: 33)

(xxii)      SSKTQTHTQQDRPPQPS from CDV-F;           (SEQ ID NO: 34)

(xxiii)     QPSTELEETRTSRARHS from CDV-F;           (SEQ ID NO: 35)

(xxiv)      RHSTTSAQRSTHYDPRT from CDV-F;           (SEQ ID NO: 36)

(xxv)       PRTSDRPVSYTMNRTRS from CDV-F;           (SEQ ID NO: 37)

(xxvi)      TRSRKQTSHRLKNIPVH from CDV-F;           (SEQ ID NO: 38)

(xxvii)     TELLSIFGPSLRDPISA from CDV-F;           (SEQ ID NO: 39)

(xxviii)    PRYIATNGYLISNFDES from CDV-F;           (SEQ ID NO: 40)

(xxix)      CIRGDTSSCARTLVSGT from CDV-F;           (SEQ ID NO: 41)

(xxx)       DESSCVFVSESAICSQN from CDV-F;           (SEQ ID NO: 42)

(xxxi)      TSTIINQSPDKLLTFIA from CDV-F;           (SEQ ID NO: 43)

(xxxii)     SPDKLLTFIASDTCPLV from CDV-F;           (SEQ ID NO: 44)

(xxxiii)    STAPPAHGVTSAPDTRAPGSTAPP from MUC-1;    (SEQ ID NO: 45)

(xxxiv)     GVTSAPDTRPAPGSTASSL from MUC-1;         (SEQ ID NO: 46)

(xxxv)      GVTSAPDTRPAPGSTASL from MUC-1;          (SEQ ID NO: 47)

(xxxvi)     TAPPAHGVTSAPDTRPAPGSTAPPKKG from MUC-1; (SEQ ID NO: 48)

(xxxvii)    STAPPAHGVTSAPDTRPAPGSTAPPK of MUC-1;    (SEQ ID NO: 49)

(xxxviii)   GVAE from FMDV-VP3 protein;             (SEQ ID NO: 50)

(xxxix)     TASGVAETTN of FMDV-VP3                  (SEQ ID NO: 51)
            (residues 170 to 179);
```

-continued and

```
(xl)        TAKSKKFPSYTATYQF from FMDV.             (SEQ ID NO: 52)
```

The T-helper epitopes disclosed herein are included for the purposes of exemplification only. Using standard peptide synthesis techniques known to the skilled artisan, the T-helper epitopes referred to herein are readily substituted for a different T-helper epitope to adapt the lipopeptide of the invention for use in a different species. Accordingly, additional T-helper epitopes known to the skilled person to be useful in eliciting or enhancing an immune response in a target species are not to be excluded.

Additional T-helper epitopes may be identified by a detailed analysis, using in vitro T-cell stimulation techniques of component proteins, protein fragments and peptides to identify appropriate sequences (Goodman and Sercarz, *Ann. Rev. Immunol.*, 1, 465, (1983); Berzofsky, In "The Year in Immunology, Vol. 2" page 151, Karger, Basel, 1986; and Livingstone and Fathman, *Ann. Rev. Immunol.*, 5, 477, (1987)).

The CTL epitope is conveniently derived from the amino acid sequence of an immunogenic protein, lipoprotein, or glycoprotein of a virus, prokaryotic or eukaryotic organism, including but not limited to a CTL epitope derived from a mammalian subject or a bacterium, fungus, protozoan, or parasite that infects said subject. Mimotopes of the CTL epitopes are specifically included within the scope of the invention.

The CTL epitope will be capable of eliciting a T cell response when administered to a mammal, preferably by activating CD8+ T cells specific for the epitope or antigen from which the epitope was derived, and more preferably, by inducing cell mediated immunity against the pathogen or tumour cell from which the epitope is derived.

Shorter CTL epitopes are preferred, to facilitate peptide synthesis. Preferably, the length of the CTL epitope will not exceed about 30 amino acids in length. More preferably, the CTL epitope sequence consists of about 25 amino acid residues or less, and more preferably less than 20 amino acid residues, and even more preferably about 8-12 amino acid residues in length.

Preferred CTL epitopes from parasites are those associated with *leishmania*, malaria, trypanosomiasis, babesiosis, or schistosomiasis, such as, for example a CTL epitope of an antigen of a parasite selected from the group consisting of: *Plasmodium falciparum*; *Circumsporozoa*; *Leishmania donovani*; *Toxoplasma gondii*; *Schistosoma mansoni*; *Schistosoma japonicum*; *Schistosoma hematobium*; and *Trypanosome brucei*.

Particularly preferred CTL epitopes of *P. falciparum* are derived from an antigen selected from the group consisting of: circumsporozoite protein (CSP), sporozoite surface protein 2 (PfSSP2), liver stage antigen 1 (LSA1), merozoite surface protein 1 (MSP1), serine repeat antigen (SERA), and AMA-1 antigen (Amante, et al. *J. Immunol.* 159, 5535-5544, 1997; Chaba et al. *Int. J. Immunopharm.* 20, 259-273, 1998; Shi et al., *Proc. Natl. Acad. Sci.* (USA) 96, 1615-1620, 1999; Wang et al. *Science* 282, 476-479, 1998; and Zevering et al. *Immunol.* 94, 445-454, 1998). Particularly preferred CTL epitopes of *L. donovani* are derived from the Repetitive Peptide (Liew et al., *J. Exp. Med.* 172, 1359 (1990)). Particularly preferred CTL epitopes of *T. gondii* are derived from the P30 surface protein (Darcy et al., *J. Immunol.* 149, 3636 (1992)).

Particularly preferred CTL epitopes of *S. mansoni* are derived from the Sm-28GST antigen (Wolowxzuk et al., *J. Immunol* 146:1987 (1991)).

Preferred virus-specific CTL epitopes are derived from Rotaviruses, Herpes viruses, Corona viruses, Picornaviruses (eg. *Apthovirus*), Respiratory Synctial virus, *Influenza* Virus, Parainfluenza virus, Adenovirus, Pox viruses, Bovine herpes virus Type I, Bovine viral diarrhea virus, Bovine rotaviruses, Canine Distemper Virus (CDV), Foot and Mouth Disease Virus (FMDV), Measles Virus (MV), Human Immunodeficiency Viruses (HIV), Feline Immunodeficiency Viruses (FIV), Epstein-Barr virus (EBV), Human Cytomegalovirus (HCMV), or hepatitis viruses, and the like.

Particularly preferred CTL epitopes of HIV-1 are derived from the env, gag, or pol proteins. Particularly preferred CTL epitopes of influenza virus are derived from the nucleoprotein (Taylor et al., *Immunogenetics* 26, 267 (1989); Townsend et al., *Nature* 348, 674 (1983)), matrix protein (Bednarek et al., *J. Immunol.* 147, 4047 (1991)) or polymerase protein (Jameson et al., *J. Virol* 72, 8682-8689, 1998; and Gianfrani et al., *Human Immunol.* 61, 438-452, 2000). Particularly preferred CTL epitopes of Lymphocytic choriomeningitis virus (LCMV) are derived from glycoprotein-1 antigen (Zinkarnagel et al. *Nature* 248, 701-702, 1974). Particularly preferred CTL epitopes of cytomegalovirus are derived from an antigen selected from the group consisting of: of pp28, pp50, pp65, pp71, pp150, gB, gH, 1E-1, 1E-2, US2, US3, US6, US11, and UL18 (eg. Diamond, U.S. Pat. No. 6,074,645, Jun. 13, 2000; Longmate et al., *Immunogenet.* 52, 165-173, 2000; Wills et al., *J. Virol.* 70, 7569-7579, 1996; Solache et al., *J. Immunol.* 163, 5512-5518, 1999; Diamond et al., *Blood* 90, 1751-1767, 1997; Kern et al., *Nature Med.* 4, 975-978, 1998; Weekes et al., *J. Virol.* 73, 2099-2108, 1999; Retière et al., *J. Virol.* 74, 3948-3952, 2000; and Salquin et al., *Eur. J. Immunol.* 30, 2531-2539, 2000). Particularly preferred CTL epitopes of Measles Virus are derived from the fusion glycoprotein (MV-F) and particularly from residues 438-446 thereof (Herberts et al. *J. Gen Virol.* 82, 2131-2142, 2001). Particularly preferred epitopes from Epstein-Barr virus (EBV) are derived from a latent nuclear antigen (EBNA) or latent membrane protein (LMP) of EBV, such as, for example, EBNA 2A, EBNA 3A, EBNA 4A, or EBNA 14a from EBV type A; EBNA 2B, EBNA 3B, EBNA 4B, or EBNA 14b from EBV type B; LMP1; or LMP2 (International Patent Application No. PCT/AU95/00140 published Sep. 16, 1995; International Patent Application No. PCT/AU97/00328 published Nov. 24, 1997; and International Patent Application No. PCT/AU98/00531 published Jan. 10, 1998).

Preferred bacteria-specific CTL epitopes are derived from *Pasteurella, Actinobacillus, Haemophilus, Listeria monocytogenes, Mycobacterium tuberculosis, Staphylococcus, Neisseria gonorrhoeae, Helicobacter pylori, Streptococcus pneumoniae, Salmonella enterica, E. coli, Shigella*, and the like.

Suitable bacterial CTL epitopes include, for example, those CTL epitopes derived from the *Mycobacterium tuberculosis* 65 kd protein (Lamb et al., *EMBO J.*, 6, 1245 (1987)); *M. tuberculosis* ESAT-6 protein (Morten et al., *Infect. Immun.* 66, 717-723, 1998); *Staphylococcus aureus* nuclease protein (Finnegan et al., *J. Exp. Med.* 164, 897 (1986)); *Escherichia coli* heat stable enterotoxin (Cardenas et al., *Infect. Immunity* 61, 4629 (1993)); and *Escherichia coli* heat labile enterotoxin (Clements et al., *Infect. Immunity* 53, 685 (1986)).

Preferred CTL epitopes from mammalian subjects are derived from and/or capable of generating T cell responses against a tumor CTL antigen. Tumor-specific CTL epitopes are usually native or foreign CTL epitopes, the expression of which is correlated with the development, growth, presence or recurrence of a tumor. In as much as such CTL epitopes are useful in differentiating abnormal from normal tissue, they are useful as a target for therapeutic intervention. Such CTL epitopes are well known in the art. Indeed, several examples are well-characterized and are currently the focus of great interest in the generation of tumor-specific therapies. Non-limiting examples of tumor CTL epitopes are derived from carcinoembryonic antigen (CEA), prostate specific antigen (PSA), melanoma antigen (MAGE, BAGE, GAGE), and mucins, such as MUC-1.

Preferred CTL epitopes for administering to a cancer patient are derived from a protein that induces cancer, such as, for example, an oncoprotein (e.g., p53, ras etc.).

In a particularly preferred embodiment, the CTL epitope will comprise or consist of an amino acid sequence selected from the group consisting of:

(i) TYQRTRALV from the NP of PR8 virus; (SEQ ID NO: 2)

(ii) KPKDELDYENDIEKKICKMEKCS of *P. falciparum* CSP; (SEQ ID NO: 53)

(iii) D1EKKICKMEKCSSVFNVVNS from *P. falciparum* CSP; (SEQ ID NO: 54)

(iv) KPIVQYDNF from *P. falciparum* LSA1; (SEQ ID NO: 55)

(v) GISYYEKVLAKYKDDLE from *P. falciparum* MSP1; (SEQ ID NO: 56)

(vi) EFTYMINFGRGQNYWEHPYQKS of *P. falciparum* AMA-1; (SEQ ID NO: 57)

(vii) DQPKQYEQHLTDYEKIKEG from *P. falciparum* AMA-1; (SEQ ID NO: 58)

(viii) NMWQEVGKAM from HIV-1 env protein; (SEQ ID NO: 59)

(ix) APTKAKRRVV from HIV-1 env protein; (SEQ ID NO: 60)

(x) CTRPNNNTRK from HIV-1 env protein; (SEQ ID NO: 61)

(xi) TVYYGVPVWK from HIV-1 env protein; (SEQ ID NO: 62)

(xii) RPVVSTQLL from HIV-1 env protein; (SEQ ID NO: 63)

(xiii) SLYNTVATLY from HIV-1 gag protein; (SEQ ID NO: 64)

(xiv) ELRSLYNTVA from HIV-1 gag protein; (SEQ ID NO: 65)

(xv) KIRLRPGGKK from HIV-1 gag protein; (SEQ ID NO: 66)

(xvi) IRLRPGGKKK from HIV-1 gag protein; (SEQ ID NO: 67)

(xvii) RLRPGGKKK from HIV-1 gag protein; (SEQ ID NO: 68)

(xviii) GPGHKARVLA from HIV-1 gag protein; (SEQ ID NO: 69)

-continued (xix) SPIETVPVKL from HIV-1 pol protein; (SEQ ID NO: 70)

(xx) ILKEPVHGVY from HIV-1 pol protein; (SEQ ID NO: 71)

(xxi) AIFQSSMTK from HIV-1 pol protein; (SEQ ID NO: 72)

(xxii) SPAIFQSSMT from HIV-1 pol protein; (SEQ ID NO: 73)

(xxiii) QVRDQAEHLK from HIV-1 pol protein; (SEQ ID NO: 74)

(xxiv) GPKVKQWPLT from HIV-1 pol protein; (SEQ ID NO: 75)

(xxv) TYQRTRALV from influenza virus nucleoprotein; (SEQ ID NO: 76)

(xvi) TYQRTRALVRTGMDP from influenza nucleoprotein; (SEQ ID NO: 77)

(xvii) IASNENMDAMESSTL from influenza virus nucleoprotein; (SEQ ID NO: 78)

(xxviii) KAVYNFATM from LCMV gp1; (SEQ ID NO: 79)

(xxix) QVKWRMTTL from EBV; (SEQ ID NO: 80)

(xxx) VFSDGRVAC from EBV; (SEQ ID NO: 81)

(xxxi) VPAPAGPIV from EBV; (SEQ ID NO: 82)

(xxxii) TYSAGIVQI from EBV; (SEQ ID NO: 83)

(xxxiii) LLDFVRFMGV from EBV; (SEQ ID NO: 84)

(xxxiv) QNGALAINTF from EBV; (SEQ ID NO: 85)

(xxxv) VSSDGRVAC from EBV; (SEQ ID NO: 86)

(xxxvi) VSSEGRVAC from EBV; (SEQ ID NO: 87)

(xxxvii) VSSDGRVPC from EBV; (SEQ ID NO: 88)

(xxxviii) VSSDGLVAC from EBV; (SEQ ID NO: 89)

(xxxix) VSSDGQVAC from EBV; (SEQ ID NO: 90)

(xl) VSSDGRVVC from EBV; (SEQ ID NO: 91)

(xli) VPAPPVGPIV from EBV; (SEQ ID NO: 92)

(xlii) VEITPYEPTG from EBV; (SEQ ID NO: 93)

(xliii) VEITPYEPTW from EBV; (SEQ ID NO: 94)

(xliv) VELTPYKPTW from EBV; (SEQ ID NO: 95)

(xlv) RRIYDLIKL from EBV; (SEQ ID NO: 96)

(xlvi) RKIYDLIEL from EBV; (SEQ ID NO: 97)

(xlvii) PYLFWLAGI. from EBV; (SEQ ID NO: 98)

(xlviii) TSLYNLRRGTALA from EBV; (SEQ ID NO: 99)

(xlix) DTPLIPLTIF from EBV; (SEQ ID NO: 100)

(l) TVFYN1PPMPL from EBV; (SEQ ID NO: 101)

(li) VEITPYKPTW from EBV; (SEQ ID NO: 102)

(lii) VSFIEFVGW from EBV; (SEQ ID NO: 103)

(liii) FRKAQIQGL from EBV; (SEQ ID NO: 104)

(liv) FLRGRAYGL from EBV; (SEQ ID NO: 105)

(lv) QAKWRLQTL from EBV; (SEQ ID NO: 106)

(lvi) SVRDRLARL from EBV; (SEQ ID NO: 107)

(lvii) YPLHEQHGM from EBV; (SEQ ID NO: 108)

(lviii) HLAAQGMAY from EBV; (SEQ ID NO: 109)

(lix) RPPIFIRRL from EBV; (SEQ ID NO: 110)

(lx) RLRAEAGVK from EBV; (SEQ ID NO: 111)

(lxi) IVTDFSVIK from EBV; (SEQ ID NO: 112)

(lxii) AVFDRKSDAK from EBV; (SEQ ID NO: 113)

(lxiii) NPTQAPVIQLVHAVY from EBV; (SEQ ID NO: 114)

(lxiv) LPGPQVTAVLLHEES from EBV; (SEQ ID NO: 115)

(lxv) DEPASTEPVHDQLL from EBV; (SEQ ID NO: 116)

(lxvi) RYSIFFDY from EBV; (SEQ ID NO: 117)

(lxvii) AVLLHEESM from EBV; (SEQ ID NO: 118)

(lxviii) RRARSLSAERY from EBV; (SEQ ID NO: 119)

(lxix) EENLLDFVRF from EBV; (SEQ ID NO: 120)

(lxx) KEHVIQNAF from EBV; (SEQ ID NO: 121)

(lxxi) RRIYDLIEL from.EBV; (SEQ ID NO: 122)

-continued (lxxii) QPRAPIRPI from EBV; (SEQ ID NO: 123)

(lxxiii) EGGVGWRHW from EBV; (SEQ ID NO: 124)

(lxxiv) CLGGLLTMV from EBV; (SEQ ID NO: 125)

(lxxv) RRRWRRLTV from EBV; (SEQ ID NO: 126)

(lxxvi) RAKFKQLL from EBV; (SEQ ID NO: 127)

(lxxvii) RKCCRAKFKQLLQHYR from EBV; (SEQ ID NO: 128)

(lxxviii) YLLEMLWRL from EBV; (SEQ ID NO: 129)

(lxxvix) YFLEILWGL from EBV; (SEQ ID NO: 130)

(lxxx) YLLEILWRL from EBV; (SEQ ID NO: 131)

(lxxxi) YLQQNWWTL from EBV; (SEQ NO: 132)

(lxxxii) LLLALLFWL from EBV; (SEQ ID NO: 133)

(lxxxiii) LLVDLLWLL from EBV; (SEQ ID NO: 134)

(lxxxiv) LLLIALWNL from EBV; (SEQ ID NO: 135)

(lxxxv) WLLLFLAIL from EBV; (SEQ ID NO: 136)

(lxxxvi) TLLVDLLWL from EBV; (SEQ ID NO: 137)

(lxxxvii) LLWLLLFLA from EBV; (SEQ ID NO: 138)

(lxxxviii) ILLIIALYL from EBV; (SEQ ID NO: 139)

(lxxxix) VLFIFGCLL from EBV; (SEQ ID NO: 140)

(xc) RLGATIWQL from EBV; (SEQ ID NO: 141)

(xci) ILYFIAFAL from EBV; (SEQ ID NO: 142)

(xcii) SLVIVTTFV from EBV; (SEQ ID NO: 143)

(xciii) LMIIPLINV from EBV; (SEQ ID NO: 144)

(xciv) TLFIGSHVV from EBV; (SEQ ID NO: 145)

(xcv) LIPETVPYI from EBV; (SEQ ID NO: 146)

(xcvi) VLQWASLAV from EBV; (SEQ ID NO: 147)

(xcvii) QLTPHTKAV from EBV; (SEQ ID NO: 148)

(xcviii) SVLGPISGHVLK from HCMV pp65; (SEQ ID NO: 149)

(xcix) FTSQYRIQGKL from HCMV pp65; (SEQ ID NO: 150)

(c) FVFPTKDVALR from HCMV pp65; (SEQ ID NO: 151)

(ci) FPTKDVAL from HCMV pp65; (SEQ ID NO: 152)

(cii) NLVPMVATV from HCMV pp65; (SEQ ID NO: 153)

(ciii) MLNIPSINV from HCMV pp65; (SEQ ID NO: 154)

(civ) RIFAELEGV from HCMV pp65; (SEQ ID NO: 155)

(cv) TPRVTGGGGAM from HCMV pp65; (SEQ ID NO: 156)

(cvi) RPHERNGFTVL from HCMV pp65; (SEQ ID NO: 157)

(cvii) RLLQTGIHV from HCMV pp65; (SEQ ID NO: 158)

(cviii) VIGDQYVKV from HCMV pp65; (SEQ ID NO: 159)

(cix) ALFFFDIDL from HCMV pp65; (SEQ ID NO: 160)

(cx) YSEHPTFTSQY from HCMV pp65; (SEQ ID NO: 161)

(cxi) VLCPKNMII from HCMV pp65; (SEQ ID NO: 162)

(cxii) DIYRIFAEL from HCMV pp65; (SEQ ID NO: 163)

(cxiii) ILARNLVPMV from HCMV pp65; (SEQ ID NO: 164)

(cxiv) EFFWDANDIY from HCMV pp65; (SEQ ID NO: 165)

(cxv) IPSINVHHY) from HCMV pp65; (SEQ ID NO: 166)

(cxvi) YILEETSVM from HCMV IE-1; (SEQ ID NO: 167)

(cxvii) CVETMCNEY from HCMV IE-1; (SEQ ID NO: 168)

(cxviii) RRIEEICMK from HCMV 1E-1; (SEQ ID NO: 169)

(cxix) TTVYPPSSTAK from HCMV pp150; (SEQ ID NO: 170)

(cxx) RRYPDAVYL from Measles Virus Fusion glycoprotein; (SEQ ID NO: 171)

(cxxi) GYKDGNEYI from *Listeria monocytogenes*; (SEQ ID NO: 172)

(cxxii) SIINFEKL from ovalbumin; and (SEQ ID NO: 173)

(cxxiii) DLMGYIPLV from the core protein of hepatitis C virus. (SEQ ID NO: 176)

It will be apparent from the preceding description that the polypeptide moiety of the subject lipopeptide is synthesized conveniently as a single amino acid chain, thereby requiring no post-synthesis modification to incorporate both epitopes. As exemplified herein, a polypeptide moiety comprising an amino acid sequence selected from the group consisting of the following is preferred:

(i)     ALNNRFQIKGVELKSTYQRTRALV;  (SEQ ID NO: 3)

(ii)    ALNNRFQIKGVELKSKTYQRTRALV; (SEQ ID NO: 4)

(iii)   KLIPNASLIENCTKAELKTYQRTRALV; (SEQ ID NO: 5)

(iv)    KLIPNASLIENCTKAELKNLVPMVATV; (SEQ ID NO: 6)

(v)     AELGEYEKLLNSVLEPIKNLVPMVATV; (SEQ ID NO: 7)

(vi)    TAAQITAGIALHQSNLNKNLVPMVATV; (SEQ ID NO: 8)

(vii)   PRYIATNGYLISNFDESKNLVPMVATV; (SEQ ID NO: 9)

(viii)  KLIPNASLIENCTKAELKYLLEMLWRL; (SEQ ID NO: 10)

(ix)    AELGEYEKLLNSVLEPIKYLLEMLWRL; (SEQ ID NO: 11)

(x)     TAAQITAGIALHQSNLNKYLLEMLWRL; (SEQ ID NO: 12)

(xi)    PRYIATNGYLISNFDESKYLLEMLWRL; (SEQ ID NO: 13)

(xii)   KLIPNASLIENCTKAELKSIINFEKL; (SEQ ID NO: 174)

(xiii) and KLIPNASLIENCTKAELKGYKDGNEYI (SEQ ID NO: 175)

(xiv)   KLIPNASLIENCTKAELKDLMGYIPLV. (SEQ ID NO: 177)

For the purposes of nomenclature, SEQ ID Nos: 3-4 relate to synthetic peptides comprising a T-helper epitope from the light chain of influenza virus hemagglutinin (i.e. SEQ ID NO: 1) and an immunodominant H-2$^d$-restricted CTL epitope from the nucleoprotein of influenza virus strain PR8 (i.e. SEQ ID NO: 2) wherein the internal lysine residue that provides a lipid attachment site at its epsilon-amino group is indicated in bold type.

In SEQ ID No: 4, an additional internal lysine residue has been engineered between the T-helper end CTL epitope (K16 in SEQ ID NO: 4).

SEQ ID No: 5 relates to a synthetic peptide comprising a T-helper epitope from canine distemper virus (CDV-F; SEQ ID NO: 20) that is active in dogs, mice, and humans and an immunodominant H-2$^d$-restricted CTL epitope from the nucleoprotein of influenza virus strain PR8 (i.e. SEQ ID NO: 2) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 5).

SEQ ID No: 6 relates to a synthetic peptide comprising a T-helper epitope from canine distemper virus (CDV-F; SEQ ID NO: 20) that is active in dogs, mice, and humans and an immunodominant HLA A2-restricted CTL epitope from the immunodominant pp65 antigen of the cytomegalovirus of humans (i.e. HCMV pp65 antigen) (i.e. SEQ ID NO: 153) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 6).

SEQ ID No: 7 relates to a synthetic peptide comprising a T-helper epitope from canine distemper virus (CDV-F; SEQ ID NO: 22) that is active in dogs, mice, and humans and an immunodominant HLA A2-restricted CTL epitope from HCMV pp65 antigen (i.e. SEQ ID NO: 153) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 7).

SEQ ID No: 8 relates to a synthetic peptide comprising a T-helper epitope from canine distemper virus (CDV-F; SEQ ID NO: 16) that is active in dogs, mice, and humans and an immunodominant HLA A2-restricted CTL epitope from HCMV pp65 antigen (i.e. SEQ ID NO: 153) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 8).

SEQ ID No: 9 relates to a synthetic peptide comprising a T-helper epitope from canine distemper virus (CDV-F; SEQ ID NO: 40) that is active in dogs, mice, and humans and an immunodominant HLA A2-restricted CTL epitope from HCMV pp65 antigen (i.e. SEQ ID NO: 153) wherein the internal lysine residue that provides a lipid attachment site at its epsilon-amino group is indicated in bold type. In this peptide, an additional internal lysine residue has been engineered between the T-helper and CTL epitope (K18 in SEQ ID. NO: 9).

SEQ ID No: 10 relates to a synthetic peptide comprising a T-helper epitope from canine distemper virus (CDV-F; SEQ ID NO: 20) that is active in dogs, mice, and humans and an immunodominant HLA A2-restricted CTL epitope from Epstein-Barr virus LMP1 antigen (i.e. EBV LMP1; SEQ ID NO: 129) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 10):

SEQ ID No: 11 relates to a synthetic peptide comprising a T-helper epitope from canine distemper virus (CDV-F; SEQ ID NO: 22) that is active in dogs, mice, and humans and an immunodominant HLA A2-restricted CTL epitope from EBV LMP1 (SEQ ID NO: 129) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 11).

SEQ ID No: 12 relates to a synthetic peptide comprising a T-helper epitope from canine distemper virus (CDV-F; SEQ ID NO: 16) that is active in dogs, mice, and humans and an immunodominant HLA A2-restricted CTL epitope from EBV LMP1 (SEQ ID NO: 129) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 12).

SEQ ID No: 13 relates to a synthetic peptide comprising a T-helper epitope from canine distemper virus (CDV-F; SEQ ID NO: 40) that is active in dogs, mice, and humans and an immunodominant HLA A2-restricted CTL epitope from EBV LMP1 (SEQ ID NO: 129) wherein the internal lysine residue that provides a lipid attachment site at its epsilon-amino group is indicated in bold type. In this peptide, an additional internal lysine residue has been engineered between the T-helper and CTL epitope (K18 in SEQ ID NO: 13).

SEQ ID No: 174 relates to a synthetic peptide comprising a T-helper epitope from canine distemper virus (CDV-F; SEQ ID NO: 20) that is active in dogs, mice, and humans and an immunodominant CTL epitope from ovalbumin (i.e. SEQ ID NO: 173) wherein the internal lysine residues that provide possible lipid attachment sites at its epsilon-amino group are indicated in bold type. Preferably, the lipid is attached via K18 in SEQ ID NO: 174, which is an additional internal lysine residue that has been engineered between the T-helper and CTL epitope.

SEQ ID No: 175 relates to a synthetic peptide comprising a T-helper epitope from canine distemper virus (CDV-F; SEQ ID NO: 20) that is active in dogs, mice, and humans and an immunodominant CTL epitope from a *Listeria monocytogenes* antigen (i.e. SEQ ID NO: 172) wherein the internal lysine residues that provide possible lipid attachment sites at its epsilon-amino group are indicated in bold type. Preferably, the lipid is attached via K18 in SEQ ID NO: 175 which is an additional internal lysine residue that has been engineered between the T-helper and CTL epitope.

SEQ ID No: 177 relates to a synthetic peptide comprising a T-helper epitope from canine distemper virus (CDV-F; SEQ ID NO: 20) that is active in dogs, mice, and humans and an immunodominant CTL epitope from the core protein of hepatitis C virus (SEQ ID NO: 176) wherein the internal lysine residues that provide possible lipid attachment sites at its epsilon-amino group are indicated in bold type. Preferably, the lipid is attached via K18 in SEQ ID NO: 177.

The skilled artisan will readily be able to synthesize additional polypeptide moieties to those exemplified herein for use in the subject lipopeptides, by substituting the T-helper epitope and/or the CTL epitope of anyone of SEQ ID Nos: 3-13, 174, 175 or 177 with another T-helper epitope or CTL epitope, such as, for example a T-helper epitope set forth in any one of SEQ ID Nos: 14-52, or a CTL epitope set forth in any one of SEQ ID Nos: 53-173 or 176. Moreover, the selection of appropriate T-helper epitope and CTL combinations will be apparent to the skilled artisan from the disclosure provided herein, according to the target species and the CTL epitope against which an immune response is sought.

The amino acid sequences of the polypeptide moities described herein, including those exemplified polypeptides set forth in SEQ ID Nos: 3-13, 174, 175 and 177 may be modified for particular purposes according to methods well known to those of skill in the art without adversely affecting their immune function. For example, particular peptide residues may be derivatized or chemically modified in order to enhance the immune response or to permit coupling of the peptide to other agents, particularly lipids. It also is possible to change particular amino acids within the peptides without disturbing the overall structure or CTL immunogenicity of the peptide. Such changes are therefore termed "conservative" changes and tend to rely on the hydrophilicity or polarity of the residue. The size and/or charge of the side chains also are relevant factors in determining which substitutions are conservative.

It is well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which specific amino acids may be substituted. Particular embodiments encompass variants that have one, two, three, four, five or more variations in the amino acid sequence of the peptide. Of course, a plurality of distinct proteins/peptides with different substitutions may easily be made and used in accordance with the invention.

Those skilled in the art are well aware that the following substitutions are permissible conservative substitutions (i) substitutions involving arginine, lysine and histidine; (ii) substitutions involving alanine, glycine and serine; and (iii) substitutions involving phenylalanine, tryptophan and tyrosine. Peptides incorporating such conservative substitutions are defined herein as biologically functional equivalents.

The importance of the hydropathic amino acid index in conferring interactive biological function on a protein is generally understood in the art (Kyte & Doolittle, *J. MoL Biol.* 157, 105-132, 1982). It is known that certain amino acids may be substituted for other amino acids having a similar hydropathic index or score and still retain a similar biological activity. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within. +/−0.2 is preferred. More preferably, the substitution will involve amino acids having hydropathic indices within +/−0.1, and more preferably within about +/−0.05.

It is also understood in the art that the substitution of like amino acids is made effectively on the basis of hydrophilicity, particularly where the biological functional equivalent protein or peptide thereby created is intended for use in immunological embodiments, as in the present case (e.g. U.S. Pat. No. 4,554,101). As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05.

Having identified peptides suitable for use as immunogens, it also is contemplated that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Another method for determining the "equivalence" of modified peptides involves a functional approach. For example, a suitable variant peptide will comprise an amino acid sequence that interacts at a significant level with a MHC Class I allele as determined using a predictive algorithm for determining MHC Class I-binding epitopes, such as, for example, the SYFPEITHI algorithm of the University of Tuebingen, Germany, or the algorithm of the HLA Peptide Binding Predictions program of the BioInformatics and Molecular Analysis Section (BIMAS) of the National Institutes of Health of the Government of the United States of America. Such variant sequences will also bind to and/or stabilize an MHC Class I molecule on the surface of an APC (eg in the PBMC fraction or buffy coat fraction of serum) and/or will induce a memory CTL response or elicit IFN-γ production and/or will stimulate CTL activity in a standard cytotoxicity assay. The determination of such functionalities is readily achievable by those skilled in the art.

The polypeptide moiety of the lipopeptide is readily synthesized using standard techniques, such as the Merrifield method of synthesis (Merrifield, *J Am Chem Soc*, 85:2149-2154, 1963) and the myriad of available improvements on that technology (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in *The Peptides* (Gross, E. and Meienhofer, J. eds.), vol. 2, pp. 1-284, Academic Press, New York; Wünsch, E., ed. (1974) *Synthese von Peptiden in Houben-Weyls Methoden der Organischen Chemie* (Müller, E., ed.), vol. 15, 4th edn., Parts 1 and 2, Thieme, Stuttgart; Bodanszky, M. (1984) *Principles of Peptide Synthesis*, Springer-Verlag, Heidelberg; Bodanszky, M. & Bodanszky, A. (1984) *The Practice of Peptide Synthesis*, Springer-Verlag, Heidelberg; Bodanszky, M. (1985) *Int. J. Peptide Protein Res.* 25, 449-474.

The lipid moiety may comprise any $C_2$ to $C_{30}$ saturated, monounsaturated, or polyunsaturated linear or branched fatty acyl group, and preferably a fatty acid group selected from the group consisting of: palmitoyl, myristoyl, stearoyl, lauroyl, octanoyl and decanoyl. Lipoamino acids are particularly preferred lipid moieties within the present context. As used herein, the term "lipoamino acid" refers to a molecule comprising one or two or three or more lipids covalently attached to an amino acid residue, such as, for example, cysteine or serine, lysine or an analog thereof. In a particularly preferred embodiment, the lipoamino acid comprises cysteine and optionally, one or two or more serine residues.

The structure of the lipid moiety is not essential to activity of the resulting lipopeptide and, as exemplified herein, palmitic acid and/or cholesterol and/or $Pam_1Cys$ and/or $Pam_2Cys$ and/or $Pam_3Cys$ can be used. The present invention clearly contemplates a range of other lipid moieties for use in the lipopeptides, such as, for example, lauric acid, stearic acid or octanoic acid, without loss of immunogenicity. Accordingly, the present invention is not to be limited by the structure of the lipid moiety, unless specified otherwise, or the context requires otherwise.

Similarly, the present invention is not to be limited by a requirement for a single lipid moiety unless specified otherwise or the context requires otherwise. The addition of multiple lipid moieties to the peptide moiety, such as, for example, to a position within the T-helper epitope, and to a position between the T-helper epitope and the B-cell epitope, is clearly contemplated.

The lipid moiety is preferably a compound having a structure of General Formula (VII):

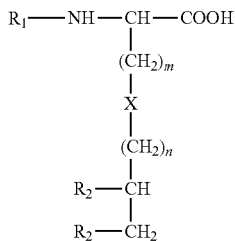

wherein:
(i) X is selected from the group consisting of sulfur, oxygen, disulfide (—S—S—), and methylene (—CH$_2$—), and amino (—NH—);
(ii) m is an integer being 1 or 2;
(iii) n is an integer from 0 to 5;
(iv) $R_1$ is selected from the group consisting of hydrogen, carbonyl (—CO—), and R'—CO— wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group;
(v) $R_2$ is selected from the group consisting of R'—CO—O—, R'—O—, R'—O—CO—; R'—NH—CO—, and R'—CO—NH—, wherein R' is selected from the group consisting of alkyl having 7 to 25 carbon atoms, alkenyl having 7 to 0.25 carbon atoms, and alkynyl having 7 to 25 carbon atoms, wherein said alkyl, alkenyl or alkynyl group is optionally substituted by a hydroxyl, amino, oxo, acyl, or cycloalkyl group; and
(vi) $R_3$ is selected from the group consisting of R'—CO—O—, R'—O—, R'-β-CO—, R'—NH—CO—, and R'—CO—NH—, wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group
and wherein each of $R_1$, $R_2$ and $R_3$ are the same or different.

Depending upon the substituent, the lipid moiety of general structure V may be a chiral molecule, wherein the carbon atoms directly or indirectly covalently bound to integers $R_1$ and $R_2$ are asymmetric dextrorotatory or levorotatory (i.e. an R or S) configuration.

Preferably, X is sulfur; m and n are both 1; $R_1$ is selected from the group consisting of hydrogen, and R'—CO—, wherein R' is an alkyl group having 7 to 25 carbon atoms; and $R_2$ and $R_3$ are selected from the group consisting of R'—CO—O—, R'—O—, R'—O—CO—, R'—NH—CO—, and R'—CO—NH—, wherein R' is an alkyl group having 7 to 25 carbon atoms.

Preferably, R' is selected from the group consisting of: palmitoyl, myristoyl, stearoyl and decanoyl. More preferably, R' is palmitoyl.

Each integer R' in said lipid moiety may be the same or different.

In a particularly preferred embodiment, X is sulfur; m and n are both 1; $R_1$ is hydrogen or R'—CO— wherein R' is palmitoyl; and $R_2$ and $R_3$ are each R'—CO—O— wherein R' is palmitoyl. These particularly preferred compounds are shown by Formula (I) and Formula (II) supra.

The lipid moiety can also have the following General Formula (VIII):

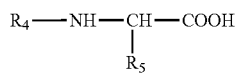

wherein:
(i) $R_4$ is selected from the group consisting of: (i) an alpha-acyl-fatty acid residue consisting of between about 7 and about 25 carbon atoms; (ii) an alpha-alkyl-beta-hydroxy-fatty acid residue; (iii) a beta-hydroxy ester of an alpha-alkyl-beta-hydroxy-fatty acid residue wherein the ester group is preferably a straight chain or branched chain comprising more than 8 carbon atoms; and (iv) a lipoamino acid residue; and
(ii) $R_5$ is hydrogen or the side chain of an amino acid residue.

Preferably, $R_4$ consists of between about 10 and about 20 carbon atoms, and more preferably between about 14 and about 18 carbon atoms.

Optionally, wherein $R_4$ is a lipoamino acid residue, the side-chain of the integers $R_4$ and $R_5$ can form a covalent linkage. For example, wherein $R_4$ comprises an amino acid selected from the group consisting of lysine, ornithine, glutamic acid, aspartic acid, a derivative of lysine, a derivative of ornithine, a derivative of glutamic acid, and a derivative of aspartic acid, then the side chain of that amino acid or derivative is covalently attached; by virtue of an amide or ester linkage, to $R_5$.

Preferably, the structure set forth in General Formula VIII is a lipid moiety selected from the group consisting of: N,N'-diacyllysine; N,N'-diacylornithine; di(monoalkyl)amide or ester of glutamic acid; di(monoalkyl)amide or ester of aspartic acid; a N,O-diacyl derivative of serine, homoserine, or threonine; and a N,S-diacyl derivative of cysteine or homocysteine.

Amphipathic molecules, particularly those having a hydrophobicity not exceeding the hydrophobicity of $Pam_3Cys$ (Formula (I)) are also preferred.

The lipid moieties of Formula (I), Formula (II), Formula (VI) or Formula (VIII) are further modified during synthesis or post-synthetically, by the addition of one or more spacer molecules, preferably a spacer that comprises carbon, and more preferably one or more amino acid residues. These are conveniently added to the lipid structure via the terminal carboxy group in a conventional condensation, addition, substitution, or oxidation reaction. The effect of such spacer molecules is to separate the lipid moiety from the polypeptide moiety and increase immunogenicity of the lipopeptide product.

Serine dimers, trimers, tetramers, etc, are particularly preferred for this purpose.

Preferably, such spacers include a terminal protected amino acid residue to facilitate the later conjugation of the modified lipoamino acid to the polypeptide.

Exemplary modified lipoamino acids produced according to this embodiment are presented as Formulae (III) and (IV), which, are readily derived from Formulae (I) and (II), respectively by the addition of a serine homodimer. As exemplified herein, $Pam_3Cys$ of Formula (I), or $Pam_2Cys$ of Formula (II) is conveniently synthesized as the lipoamino acids $Pam_3Cys$-Ser-Ser of Formula (III), or $Pam_2Cys$-Ser-Ser of Formula (IV) for this purpose.

Formula (III):
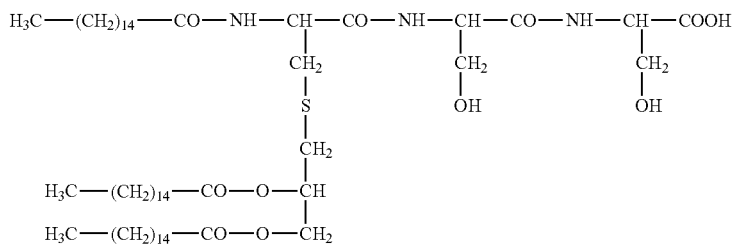

Formula (IV):
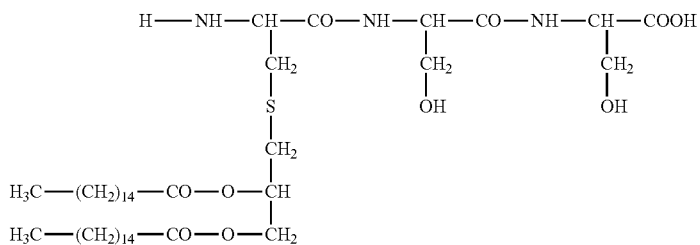

As an alternative to the addition of a spacer to the lipid moiety, the spacer may be added to the epsilon amino group of the internal lysine residue or to the terminal side-chain group of a lysine analog in the polypeptide moiety, either as a short peptide, such as, for example a serine homodimer, homotrimer, homotetramer, etc, or alternatively, by the sequential addition of amino acid residues, thereby producing a branched polypeptide chain. This approach takes advantage of the modified nature of the terminal side-chain group on the internal lysine or lysine analog to achieve specificity in the addition of the spacer. Naturally, to avoid sequential spacer addition, the terminal amino acid residue of the spacer should preferably be protected, such that de-protection can facilitate conjugation of the lipid moiety to the branched polypeptide.

Alternatively, the spacer may be added to a non-modified epsilon amino group of the polypeptide by conventional nucleophilic substitution reaction. However, it is preferred to follow this approach if the polypeptide has an amino acid sequence comprising a single internal lysine residue and a blocked N-terminus.

The lipid moiety is prepared by conventional synthetic means, such as, for example, the methods described in U.S. Pat. Nos. 5,700,910 and 6,024,964, or alternatively, the method described by Wiesmuller et al, *Hoppe Seylers Zur Physiol. Chem.* 364, 593 (1983), Zeng et al., *J. Pept. Sci* 2, 66 (1996); Jones et al., *Xenobiotica* 5, 155 (1975), or Metzger et al., *Int. J. Pept. Protein Res.* 38, 545 (1991). Those skilled in the art will be readily able to modify such methods to achieve the synthesis of a desired lipid for use conjugation to a polypeptide.

Combinations of different lipids are also contemplated for use in the lipopeptides of the invention. For example, one or two myristoyl-containing lipids or lipoamino acids are attached via internal lysine or lysine analog residues to the polypeptide moiety, optionally separated from the polypeptide by a spacer, with one or two palmitoyl-containing lipid or lipoamino acid molecules attached to carboxy terminal lysine amino acid residues. Other combinations are not excluded.

The lipopeptides of the invention are readily modified for diagnostic purposes. For example, it is modified by addition of a natural or synthetic hapten, an antibiotic, hormone, steroid, nucleoside, nucleotide, nucleic acid, an enzyme, enzyme substrate, an enzyme inhibitor, biotin, avidin, polyethylene glycol, a peptidic polypeptide moiety (e.g. tuftsin, polylysine), a fluorescence marker (e.g. FITC, RITC, dansyl, luminol or coumarin), a bioluminescence marker, a spin label, an alkaloid, biogenic amine, vitamin, toxin (e.g. digoxin, phalloidin, amanitin, tetrodotoxin), or a complex-forming agent.

As exemplified herein, highly immunogenic lipopeptides capable of inducing CTL responses are provided, said lipopeptides comprising $Pam_3Cys$ of Formula (I), or $Pam_2Cys$ of Formula (II) conjugated via the epsilon amino group of a lysine residue positioned between the CD4+ T-helper epitope and a $CD8^+$ CTL epitope.

Preparation of Lipopeptides

A second aspect of the invention provides a method of producing a lipopeptide comprising:
(i) producing a polypeptide comprising an amino acid sequence that comprises:
  (a) the amino acid sequence of a T helper cell (Th) epitope and the amino acid sequence of a CTL epitope, wherein said amino acid sequences are different; and
  (b) one or more internal lysine residues or internal lysine analog residues; and
(iii) covalently attaching each of said one or more lipid moieties directly or indirectly to an epsilon-amino group of said one or more internal lysine residues or to the terminal side-chain group of said one or more internal lysine analog residues so as to produce a lipopeptide having the lipid moiety attached to the epsilon amino group of said internal lysine residue or having the lipid moiety attached to the terminal side-chain group of said internal lysine analog residue.

Preferably, the method further comprises production of the lipid moiety.

Conventional chemical syntheses referred to herein are the preferred means for producing the polypeptide moiety and the lipid moiety.

Preferably, the internal lysine or lysine analog is modified by selective removal of a blocking group (eg: Mtt) from the terminal side-chain group so as to permit the addition of an amino acid residue, a spacer or lipid moiety, including a lipoamino acid, at that position.

For attachment of the lipid to the polypeptide, it is convenient for the functional groups of the polypeptide to be protected in a manner known in the art of peptide synthesis, to ensure that no undesirable reactions at those groups takes place at a significant reaction rate.

By known coupling processes, the polypeptide is synthesized on a solid or soluble carrier, such as a polymer (for example Merrifield resin) and made available for conjugation to a spacer, amino acid, or lipid. For example, the terminal side chain group of the lysine or lysine analog (eg. epsilon amino group of the internal lysine) is protected by one of a number of protecting groups. Blocking groups (also called protecting groups or masking groups) are used to protect the amino group of the amino acid having an activated carboxyl group that is involved in the coupling reaction, or to protect the carboxyl group of the amino acid having an acylated amino group that is involved in the coupling reaction. For coupling to occur, a blocking group must be removed without disrupting a peptide bond, or any protecting group attached to another part of the peptide.

For solid phase peptide synthesis, blocking groups that are stable to the repeated treatments necessary for removal of the amino blocking group of the growing peptide chain and for repeated amino acid couplings, are used for protecting the amino acid side-chains. Additionally, the peptide-resin anchorage that protects the C-terminus of the peptide must be protected throughout the synthetic process until cleavage from the resin is required. Accordingly, by the judicious selection of orthogonally protected alpha-amino acids, lipids and/or amino acids are added at desired locations to a growing peptide whilst it is still attached to the resin.

Preferred amino blocking groups are easily removable but sufficiently stable to survive conditions for the coupling reaction and other manipulations, such as, for example, modifications to the side-chain groups. Preferred amino blocking groups are selected from the group consisting of: (i) a benzyloxycarbonyl group (Z or carbobenzoxy) that is removed easily by catalytic hydrogenation at room temperature and ordinary pressure, or using sodium in liquid ammonia and hydrobromic acid in acetic acid; (ii) a t-Butoxycarbonyl group (Boc) that is introduced using t-butoxycarbonyl azide or di-tert-butyldicarbonate and removed using mild acid such as, for example, trifluoroacetic acid (50% TFA in dichloromethane), or HCl in acetic acid/dioxane/ethylacetate; (iii) a 9-fluorenylmethyloxycarbonyl group (Fmoc) that is cleaved under mildly basic, non-hydrolytic conditions, such as, for example, using a primary or secondary amine (eg. 20% piperidine in dimethyl formamide); (iv) a 2-(4-biphenylyl) propyl(2)oxycarbonyl group (Bpoc); (v) a 2-nitro-phenylsulfenyl group (Nps); and (vi) a dithia-succinoyl group (Dts).

Side chain-protecting groups will vary for the functional side chains of the amino acids forming the peptide being synthesized. Side-chain protecting groups are generally based on the Bzl group or the tBu group. Amino acids having alcohols or carboxylic acids in the side-chain are protected as Bzl ethers, Bzl esters, cHex esters, tBu ethers, or tBu esters. Side-chain protection of Fmoc amino acids requires blocking groups that are ideally base stable and weak acid (TFA) labile. For example, the epsilon-amino group of Lysine is protected using Mtt (eg. Fmoc-lysine(Mtt)-OH). Alternatively, a halogenated benzyl derivative such as ClZ is used to protect the lysine side chain should enhanced acid stability be required.

The thiol group of Cystine, the imidazole of Histidine, or guanidino group of Arginine, generally require specialised protection. Many different protecting groups for peptide synthesis have been described (see The Peptides, Gross et al. eds., Vol. 3, Academic Press, New York, 1981).

The two most widely used protection strategies are the Boc/Bzl- and the Fmoc/tBu-strategies. In Boc/Bzl, Boc is used for amino protection and the side-chains of the various amino acids are protected using Bzl- or cHex-based protecting groups. A Boc group is stable under catalytic hydrogenation conditions and is used orthogonally along with a Z group for protection of many side chain groups. In Fmoc/tBu, Fmoc is used for amino protection and the side-chains are protected with tBu-based protecting groups.

Peptides are lipidated by methods well known in the art. Standard condensation, addition, substitution or oxidation (e.g. disulfide bridge formation or amide bond formation between a terminal amino group on the internal lysine or lysine analog with the carboxy terminal group of an incoming amino acid or peptide or lipoamino acid) reactions result in the addition of lipid to the polypeptide.

In an alternative embodiment, a peptide of the present invention for use as an immunogen is produced by chemoselective ligation or chemical conjugation or oxime chemistry. Such methods are well-known in the art, and allow for the individual peptide components to be produced by chemical or recombinant means, followed by their chemoselective ligation in an appropriate configuration or conformation or order (eg. Nardin et al., *Vaccine* 16, 590 (1998); Nardin et al., *J. Immunol.* 166, 481 (2001); Rose et al., *Mol. Immunol.* 32, 1031 (1995); Rose et al., *Bioconjug. Chem* 7, 552 (1996); and Zeng et al., *Vaccine* 18, 1031 (2000), which are incorporated herein by reference).

Lipopeptide Formulations

The lipopeptide is conveniently formulated in a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the pharmaceutical composition are adjusted according to routine skills in the art.

The addition of an extrinsic adjuvant to the lipopeptide formulation, although generally not required, is also encompassed by the invention. Such extrinsic adjuvants include all acceptable immunostimulatory compounds such as, for example, a cytokine, toxin, or synthetic composition. Exemplary adjuvants include IL-1, IL-2, BCG, aluminum hydroxide, N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), lipid A, MKL and RIBI, which contains three components extracted from bacteria, monophosphoryl lipid A, trehalose dimycolate and cell wall skeleton (MPL+TDM+CWS) in a 2% squalene/Tween 80 emulsion.

It may be desirable to co-administer biologic response modifiers (BRM) with the lipopeptide, to down regulate suppressor T cell activity. Exemplary BRM's include, but are not limited to, Cimetidine (CIM; 1200 mg/d) (Smith/Kline, PA, USA); Indomethacin (IND; 150 mg/d) (Lederle, N.J., USA); or low-dose Cyclophosphamide (CYP; 75, 150 or 300 mg/m.sup.2) (Johnson/Mead, N.J., USA).

Use of the Lipopeptide in Immunization

The novel lipopeptides of the invention differ in essential aspects from known lipopeptide conjugates of CTL epitopes in having the lipid moiety conjugated exclusively through the terminal side-chain group of an internal lysine or lysine analog residue, thereby enhancing T cell responses without the administration of additional adjuvant. Accordingly, a particular utility of the lipopeptides of the present invention is in the fields of eliciting a T cell response either in vivo or ex vivo, synthetic vaccine preparation, diagnostic methods employing T cells, and immunotherapy for veterinary and human medicine.

More particularly, the lipopeptide of the present invention enhances CTL memory responses against the CTL epitope moiety when administered to an animal subject, without any requirement for an adjuvant to achieve a similar level of CTL activation. In addition, enhanced maturation of dendritic cells and other biological effects which include induction of IFN-γ producing CD8+ cells as well as viral, bacterial and tumour cell clearance have been observed following administration of vaccine:

Accordingly, a further aspect of the invention provides a method of enhancing cell mediated immunity against the organism from which the CTL epitope is derived in a subject comprising administering the lipopeptide of the invention or a derivative or a functionally equivalent variant of said lipopeptide or a vaccine composition comprising said lipopeptide or variant or derivative for a time and under conditions sufficient to activate a CTL and/or a CTL precursor of said subject.

By "CTL precursor" is meant a naive T cell (ie. a T cell that expresses one or more T cell receptors on its surface and is capable of proliferating and differentiating into a memory T cell or effector T cell).

Preferably, the lipopeptide or vaccine is administered prophylactically to a subject not harboring a latent or active infection by a parasite, bacterium or virus, or suffering from a cancer or administered therapeutically to a subject harboring a latent or active infection by a parasite, bacteria or Virus or suffering from a cancer. In the present context, the term "activate" means that the ability of a T cell to recognize and lyse a cell harboring an antigen from which the CTL epitope is derived is enhanced, or that the ability of a T cell to recognize a T cell epitope of said antigen is enhanced, either transiently or in a sustained manner. The term "activate" shall also be taken to include a reactivation of a T cell population following activation of a latent infection by a parasite or bacteria or virus, or following re-infection with a parasite or bacteria or virus, or following immunization of a previously-infected subject with a lipopeptide or composition of the invention.

Those skilled in the art are aware that optimum T cell activation requires cognate recognition of antigen/MHC by the T cell receptor (TcR), and a co-stimulation involving the ligation of a variety of cell surface molecules on the T cell with those on an antigen presenting cell (APC). The costimulatory interactions CD28/B7, CD40L/CD40 and OX40/OX40L are preferred, but not essential for T cell activation. Other costimulation pathways may operate.

For determining the activation of a CTL or precursor CTL or the level of epitope-specific activity, standard methods for assaying the number of $CD8^+$ T cells in a specimen can be used. Preferred assay formats include a cytotoxicity assay, such as for example the standard chromium release assay, the assay for IFN-γ production; such as, for example, the ELISPOT assay. These assay formats are described in detail in the accompanying examples.

MHC class −1 Tetramer assays can also be utilized, particularly for CTL. Epitope-specific quantitation of $CD8^+$ T cells (Altman et al., *Science* 274, 94-96, 1996; Ogg et al., *Curr Opin Immunol.* 10, 393-396, 1998). To produce tetramers, the carboxyl terminus of an MHC molecule, such as, for example, the HLA A2 heavy chain, is associated with a specific peptide epitope or polyepitope, and treated so as to form a tetramer complex having bound hereto a suitable reporter molecule, preferably a fluorochrome such as, for example, fluoroscein isothiocyanate (FITC), phycoerythrin, phycocyanin or allophycocyanin. Tetramer formation is achieved, for example, by producing the MHC-peptide fusion protein as a biotinylated molecule and then mixing the biotinylated MHC-peptide with deglycosylated avidin that has been labeled with a fluorophore, at a molar ratio of 4:1. The Tetramers produced bind to a distinct set of $CD8^+$ T cell receptors (TcRs) on a subset of $CD8^+$ T cells derived from the subject (eg in whole blood or a PBMC sample), to which the peptide is HLA restricted. There is no requirement for in vitro T cell activation or expansion. Following binding, and washing of the T cells to remove unbound or non-specifically bound Tetramer, the number of $CD8^+$ cells binding specifically to the HLA-peptide Tetramer is readily quantified by standard flow cytometry methods, such as, for example, using a FACSCalibur Flow cytometer (Becton Dickinson). The Tetramers can also be attached to paramagnetic particles or magnetic beads to facilitate removal of non-specifically bound reporter and cell sorting. Such particles are readily available from commercial sources (eg. Beckman Coulter, Inc., San Diego, Calif., USA) Tetramer staining does not kill the labeled cells; therefore cell integrity is maintained for further analysis. MHC Tetramers enable the accurate quantitative analyses of specific cellular immune responses, even for extremely rare events that occur at less than 1% of $CD8^+$ T cells (Bodinier et al., *Nature Med.* 6, 707-710, 2000; Ogg et al., *Curr Opin Immunol.* 10, 393-396, 1998).

The total number of $CD8^+$ cells in a sample can also be determined readily, such as, for example, by incubating the sample with a monoclonal antibody against CD8 conjugated to a different reporter molecule to that used for detecting the Tetramer. Such antibodies are readily available (eg. Becton Dickinson). The relative intensities of the signals from the two reporter molecules used allows quantification of both the total number of $CD8^+$ cells and Tetramer-bound T cells and a determination of the proportion of total T cells bound to the Tetramer.

Because $CD4^+$ T-helper cells function in CMI as producers of cytokines, such as, for example IL-2, to facilitate the expansion of $CD8^+$ T cells or to interact with the APC thereby rendering it more competent to activate $CD8^+$ T cells, cytokine production is an indirect measure of T cell activation. Accordingly, cytokine assays can also be used to determine the activation of a CTL or precursor CTL or the level of cell mediated immunity in a human subject. In such assays, a cytokine such as, for example, IL-2, is detected or production of a cytokine is determined as an indicator of the level of epitope-specific reactive T cells.

Preferably, the cytokine assay format used for determining the level of a cytokine or cytokine production is essentially as described by Petrovsky and Harrison, *J. Immunol. Methods* 186, 37-46, 1995, which assay reference is incorporated herein.

Preferably, the cytokine assay is performed on whole blood or PBMC or buffy coat.

Preferably, the lipopeptide or derivative or variant or vaccine composition is administered for a time and under conditions sufficient to elicit or enhance the expansion of $CD8^+$ T cells.

Still more preferably, the lipopeptide or derivative or variant or vaccine composition is administered for a time and under conditions sufficient for cell mediated immunity (CMI) to be enhanced in the subject.

By "CMI" is meant that the activated and clonally expanded CTLs are MHC-restricted and specific for a CTL epitope. CTLs are classified based on antigen specificity and MHC restriction, (ie., non-specific CTLs and antigen-specific, MHC-restricted CTLs). Non-specific CTLs are composed of various cell types, including NK cells and can function very early in the immune response to decrease pathogen load, while antigen-specific responses are still being established. In contrast, MHC-restricted CTLs achieve optimal activity later than non-specific CTL, generally before antibody production. Antigen-specific CTLs inhibit or reduce the spread of a pathogen and preferably terminate infection.

CTL activation, clonal expansion, or CMI can be induced systemically or compartmentally localized. In the case of compartmentally localized effects, it is preferred to utilize a vaccine composition suitably formulated for administration to that compartment. On the other hand, there are no such stringent requirements for inducing CTL activation, expansion or CMI systemically in the subject.

The effective amount of lipopeptide to be administered, either solus or in a vaccine composition to elicit CTL activation, clonal expansion or CMI will vary, depending upon the nature of the immunogenic epitope, the route of administration, the weight, age, sex, or general health of the subject immunized, and the nature of the CTL response sought. All such variables are empirically determined by art-recognized means.

The lipopeptide, optionally formulated with any suitable or desired carrier, adjuvant, BRM, or pharmaceutically acceptable excipient, is conveniently administered in the form of an injectable composition. Injection may be intranasal, intramuscular, sub-cutaneous, intravenous, intradermal, intraperitoneal, or by other known route. For intravenous injection, it is desirable to include one or more fluid and nutrient replenishers.

The optimum dose to be administered and the preferred route for administration are established using animal models, such as, for example, by injecting a mouse, rat, rabbit, guinea pig, dog, horse, cow, goat or pig, with a formulation comprising the lipopeptide, and then monitoring the CTL immune response using any conventional assay.

The use of HLA A2/$K^b$ transgenic mice carrying a chimeric human-mouse Class I major histocompatibility complex (MHC) locus composed of the α1 and α2 domains of the human HLA A*0201 allele and the α3 domain of the mouse H-2$K^b$ Class I molecules (Vitiello et al., *J. Exp. Med.* 173, 1007, 1991) is particularly preferred for testing responses in vivo to a lipopeptide of the invention that comprises a HLA A2-restricted CTL epitope or a vaccine composition comprising same.

Without being bound by any theory or mode of action, we believe that the biological effects of the lipopeptides are exerted through their ability to stimulate and mature dendritic cells. It is the dendritic cells which then activate CD4+ and CD8+ T cells in the draining lymph nodes. For this reason, we would not nor would it be possible to activate T cells: directly as envisaged. The following section has therefore been modified accordingly to accommodate the notion of dendritic cell activation.

In a related embodiment, the invention provides a method of enhancing the cell mediated immunity of a subject, said method comprising contacting ex vivo cells, preferably dendritic cells, obtained from a subject with an immunologically active lipopeptide of the invention or a derivative or variant thereof or a vaccine composition comprising said lipopeptide or derivative or variant for a time and under conditions sufficient to mature said dendritic cells. Said dendritic cells are then capable of conferring epitope specific activation of T cells.

In a preferred embodiment, the invention provides a method of enhancing the cell mediated immunity of a subject, said method comprising:
(i) contacting ex vivo dendritic cells obtained from a subject with an immunologically active lipopeptide of the invention or a derivative or variant thereof or a vaccine composition comprising said lipopeptide or derivative or variant for a time and under conditions sufficient to mature said dendritic cells; and
(ii) introducing the activated dendritic cells autologously to the subject or syngeneically to another subject in order that T cell activation occurs.

The T cell may be a CTL or CTL precursor cell.

The subject from whom the dendritic cells are obtained may be the same subject or a different subject to the subject being treated. The subject being treated can be any subject carrying a latent, or active infection by a pathogen, such as, for example, a parasite, bacterium or virus or a subject who is otherwise in need of obtaining vaccination against such a pathogen or desirous of obtaining such vaccination. The subject being treated may also be treated for a tumour that they are carrying.

By "epitope specific activity" is meant that the T cell is rendered capable of being activated as defined herein above (ie. the T cell will recognize and lyze a cell harboring a pathogen from which the CTL epitope is derived, or is able to recognize a T cell epitope of an antigen of a pathogen either transiently or in a sustained manner). Accordingly, it is particularly preferred for the T cell to be a CTL precursor which by the process of the invention is rendered able to recognize and lyze a cell harboring the pathogen or able to recognize a T cell epitope of an antigen of the pathogen either transiently or in a sustained manner.

For such an ex vivo application; the dendritic cells are preferably contained in a biological sample obtained from a subject, such as, for example, blood, PBMC or a buffy coat fraction derived therefrom.

Another aspect of the invention provides a method of providing or enhancing immunity against a pathogen in an uninfected subject comprising administering to said subject an immunologically active lipopeptide of the invention or a derivative or variant thereof or a vaccine composition comprising said lipopeptide or derivative or variant for a time and under conditions sufficient to provide immunological memory against a future infection by the pathogen. As with the other embodiments described herein, the pathogen may be a parasite, virus or bacterium, and is preferably a parasite, virus or bacterium referred to herein above from which a CTL epitope has been identified.

In a related embodiment, the invention provides a method of enhancing or conferring immunity against a pathogen in an uninfected subject comprising contacting ex vivo dendritic cells obtained from said subject with an immunologically active lipopeptide of the invention or a derivative or variant thereof or a vaccine composition comprising said lipopeptide or derivative or variant for a time and under conditions sufficient to confer epitope specific activity on T cells.

Accordingly, this aspect of the invention provides for the administration of a prophylactic vaccine to the subject, wherein the active substituent of said vaccine (i.e. the lipopeptide of the invention) induces immunological memory via memory T cells in an uninfected individual. The preferred embodiments of vaccination protocols described herein for enhancing the cell mediated immunity of a subject apply mutatis mutandis to the induction of immunological memory against the pathogen in a subject.

The present invention is further described with reference to the following non-limiting examples and the drawings. The examples provided herein in mice are accepted models for equivalent diseases in humans and the skilled person will readily be capable of extending the findings presented herein for such models to a human disease context without undue experimentation.

EXAMPLE 1

Materials and Methods

Chemicals

Unless otherwise stated chemicals were of analytical grade or its equivalent. N,N'-dimethylformamide (DMF), piperidine, trifluoroacetic acid (TFA), O'benzotriazole-N,N,N',N'-tetramethyluronium hexafluorophosphate (HBTU), 1-hydroxybenzotriazole (HOBt) and diisopropylethylamine (DIPEA) and diisopropylcarbodiimide (DIPCDI) were obtained from Auspep Pty. Ltd., Melbourne, Australia and Sigma-Aldrich Pty. Ltd., Castle Hill, Australia. O'benzotriazole-N,N,N',N'-tetramethyluronium tetrafluoroborate (TBTU) was obtained from Bachem, (Bachem AG, Switzerland). Dichloromethane (DCM) and diethylether were from Merck Pty Ltd. (Kilsyth, Australia). Phenol and triisopropylsilane (TIPS) were from Aldrich (Milwaukee, Wis.) and trinitrobenzylsulphonic acid (TNBSA) and diaminopyridine (DMAP) from Fluka; 1,8-diazabicyclo[5.4.0]undec-7-ene (DBU) was obtained from Sigma and palmitic acid was from Fluka.

Viruses

The type A influenza viruses used in this study were an H3N1 subtype virus referred to as Mem 71, which was derived by genetic reassortment of A/Memphis/I/71 (H3N2) X A/Bellamy/42 (H1N1). Virus was grown for 2 days in the allantoic cavity of 10-day embryonated hen's eggs. Allantoic fluid containing virus was stored in aliquots at −70° C. Infectious virus titers were obtained by assay of plaque formation in monolayers of Madin-Darby canine kidney (MDCK) cells (Tannock et al, *Infect. Immun.* 43, 457-462, 1984) and are expressed as PFU/milliliter.

Bacteria

*Listeria monocytogenes* EGD was cultured overnight at 37° C. on Horse Blood Agar (HBA) plates. The bacteria were washed off the plates using sterile PBS and the concentration adjusted to $5 \times 10^3$ *Listeria* cells/ml. Balb/c mice were infected intravenously with $1 \times 10^3$ *Listeria* cells. The dose was checked retrospectively by plating serial 10-fold dilutions on HBA plates.

Peptide Syntheses

Peptides Comprising Influenza Virus CTL Epitopes

A panel of immunogens was synthesized that incorporated peptides representing a minimal determinant for CD8+ T cells and/or a determinant for CD4+ T cells, both from influenza virus. The peptide NP (147-155) with the sequence TYQRTRALV (a CTL determinant present in the NP of PR8 virus; SEQ ID NO: 2) is the dominant CD8+ T-cell determinant recognized by BALB/c mice and is common to all type A influenza virus strains (Bodmer et al, *Cell* 52, 253-258; 1988; and Sherman et al, *J. Exp. Med.* 175, 1221-1226, 1992). The peptide HA2 (166-180), with the sequence ALNNRF-QIKGVELKS (SEQ ID NO: 1), is a CD4+ T-helper determinant present within the HA2 chain of Mem71 influenza virus hemagglutinin elicits CD4+ T cells that are crossreactive with all viruses of the H3 subtype (Jackson et al, *Virology* 198, 153-170, 1994).

Peptides Comprising *L. monocytocenes* CTL Epitopes

An immunogenic peptide was synthesized that incorporated a minimal CTL epitope with amino acid sequence GYKDGNEYI (residues 91-99 of the protein literialysin) from *L. monocytogenes* (ie. SEQ ID NO: 172) and a T-helper epitope from CDV-F (SEQ ID NO: 20).

Peptides comprising a CTL epitope expressed by B16-OVA tumour cell line.

An immunogenic peptide was synthesized that incorporated a CTL epitope with amino acid sequence SIINFEKL (SEQ ID NO: 173) and a T-helper epitope from CDV-F (SEQ ID NO: 20).

Peptides comprising a CTL epitope from the core protein of hepatitis C virus.

An immunogenic peptide was synthesized that incorporated a CTL epitope with amino acid sequence DLMGYIPLV (SEQ ID NO: 176) and a T-helper epitope from CDV-F (SEQ ID NO: 20).

General Procedures

Synthetic immunogens were assembled by conventional solid-phase methodology using Fmoc chemistry. The general procedure used for the peptide synthesis has been described by Jackson et al., *Vaccine* 18, 355 (1999). To enable lipid attachment between the CD4+ T helper epitope and the CTL epitope, Fmoc-lysine(Mtt)-OH was inserted at a point between the two epitopes in the approximate centre of the resin-bound peptide. Following completion of peptide synthesis the Mtt group was removed by continual flow washing with 1% TFA in dichloromethane over a period of 30-45 mins.

Synthesis of Lipid Moieties of Formulae (I)

Pam$_3$Cys was prepared according to the method described by Weismuller et al., *Hoppe Seylers Z Physiol Chem* 364, 593 (1983), as modified according to the method described by Zeng et al., *J Pept Sci* 2, :66 (1996). The lipoamino acid Pam$_3$Cys is coupled to the exposed epsilon-amino group of lysine according to the procedure described by Zeng et al. (supra). Briefly, a 2-fold excess of Pam$_3$Cys, TBTU and HOBt was dissolved in DCM and a 3-fold excess of DIPEA added. This solution was then added to the resin-bound peptide to generate the lipopeptide.

Synthesis of Lipid Moieties of Formulae (II)

The synthesis of Pam$_2$Cys was adapted from previously described methods as described by Jones et al., *Xenobiotica* 5, 155 (1975) and Metzger et al., *Int J Pept Protein Res* 38, 545 (1991), with the exception that 3-bromo-propan-1,2-diol was used instead of 3-chloro-propan-1,2-diol, and centrifugation and not filtration was used to recover the product.

Synthesis of Lipopeptides

Lipopeptides produced in this study had the general structures shown in FIG. 1. Amino acid sequences of the peptide moieties included in the various lipopeptides are shown in FIG. 2. Pam$_2$Cys was coupled to peptides according to the methods described by Jones et al., *Xenobiotica* 5, 155 (1975.) and Metzger et al., *Int J Pept Protein Res* 38, 545 (1991), with the following modifications:

I. Synthesis of S-(2,3-Dihydroxypropyl)cysteine

Triethylamine (6 g, 8.2 ml, 58 mmoles) was added to L-cysteine hydrochloride (3 g, 19 mmole) and 3-bromo-propan-1,2-diol (4.2 g, 2.36 ml, 27 mmole) in water and the homogeneous solution kept at room temperature for 3 days. The solution was reduced in vacuo at 40° C. to a white residue which was boiled with methanol (100 ml), centrifuged and the residue dissolved in water (5 ml). This aqueous solution was added to acetone (300 ml) and the precipitate isolated by centrifugation. The precipitate was purified by several precipitations from water with acetone to give S-(2,3-dihydroxypropyl)cysteine as a white amorphous powder (2.4 g, 12.3 mmol, 64.7%).

II. Synthesis of N-Fluorenylmethoxycarbonyl-S-(2, 3-dihydroxypropyl)-cysteine (Fmoc-Dhc-OH)

S-(2,3-dihydroxypropyl)cysteine (2.45 g, 12.6 mmole) was dissolved in 9% sodium carbonate (20 ml). A solution of fluorenylmethoxycarbonyl-N-hydroxysuccinimide (3.45 g, 10.5 mmole) in acetonitrile (20 ml) was added and the mixture stirred for 2 h, then diluted with water (240 ml), and extracted with diethyl ether (25 ml×3). The aqueous phase was acidified to pH 2 with concentrated hydrochloric acid and was then extracted with ethyl acetate (70 ml×3). The extract was washed with water (50 ml×2) and saturated sodium chloride solution (50 ml×2), dried over sodium sulfate and evaporated to dryness. Recrystallisation from ether and ethyl acetate at −20° C. yielded a colourless powder (2.8 g, 6.7 mmole, 63.8%).

III. Coupling of Fmoc-Dhc-OH to Resin-Bound Peptide

Fmoc-Dhc-OH (100 mg, 0.24 mmole) was activated in DCM and DMF (1:1, v/v, 3 ml) with HOBt (36 mg, 0.24 mmole) and DICI (37 ul, 0.24 mmol) at 0° C. for 5 min. The mixture was then added to a vessel containing the resin-bound peptide (0.04 mmole, 0.25 g amino-peptide resin). After shaking for 2 h the solution was removed by filtration and the resin was washed with DCM and DMF (3×30 ml each). The reaction was monitored for completion using the TNBSA test. If necessary a double coupling was performed.

IV. Palmitoylation of the Two Hydroxy Groups of the Fmoc-Dhc-Peptide Resin

Palmitic acid (204 mg, 0.8 mmole), DICI (154 ul, 1 mmole) and DMAP (9.76 mg, 0.08 mmole) were dissolved in 2 ml of DCM and 1 ml of DMF. The resin-bound Fmoc-Dhc-peptide resin (0.04 mmole, 0.25 g) was suspended in this solution and shaken for 16 h at room temperature. The solution was removed by filtration and the resin was then washed with DCM and DMF thoroughly to remove any residue of urea. The removal of the Fmoc group was accomplished with 2.5% DBU (2×5 mins).

All resin-bound peptide constructs were cleaved from the solid phase support with reagent B (88% TFA, 5% phenol, 2% TIPS, 5% water) for 2 hr, and purified by reversed phase chromatography as described by Zeng et al., *Vaccine* 18, 1031 (2000).

Analytical reversed phase high pressure liquid chromatography (RP-HPLC) was carried out using a Vydac C4 column (4.6×300 mm) installed in a Waters HPLC system and developed at a flow rate of 1 ml/min using 0.1% TFA in H$_2$O and 0.1% TFA in CH$_3$CN as the limit solvent. All products presented as a single major peak on analytical RP-HPLC and had the expected mass when analysed by MALDI-TOF mass spectrometry on a Bruker BIFLEX instrument equipped with delayed ion extraction.

In some cases two serine residues (Ser-Ser) were added between the peptide and lipid moiety in which case serine residues were added to the ε-amino group of the central lysine residue before the lipid moiety was attached.

A schematic diagram of the peptides and lipopeptides used in this study is shown in FIG. 1.

Immunization Protocols

Peptides Comprising Influenza Virus CTL Epitopes

Groups of female BALB/c mice, 6 to 8 weeks old, were inoculated at day 0 and again on day 28. For subcutaneous (s.c.) inoculations 9 nmoles of lipopeptide constructs were prepared in 100 µl volume of saline per dose and non-lipidated peptides formulated as an emulsion in an equal volume of complete Freund's adjuvant (CFA) for the primary injection or incomplete Freund's adjuvant for the secondary inoculation. For intranasal (i.n.) inoculations, 9 nmoles of peptide in 50 µl of saline were applied to the nares of mice anaesthetised with penthrane for inhalation.

Peptides Comprising a CTL Epitope of L. monocytogenes

5 BALB/c mice were inoculated with 9 nmoles of non-lipidated peptide ([P25]-Lys-[LL091-99]), or lipidated peptide ([P25]-Lys(Pam$_2$Cys-Ser-Ser)-[LL091-99]) in which lipid was attached between the two epitopes at the approximate centre of the molecule, or with 1000 bacteria: In the case of peptide vaccine, inoculation was subcutaneous and in the case of bacteria inoculation was intravenous. The number of interferon-γ producing cells present in spleen was measured on day 28 following in vitro stimulation with the CTL epitope or no antigen. The vertical axis shows the number of interferon-γ producing cells per 1,000,000 splenocytes.

Peptides Comprising a CTL Epitope of Ovalbumin

Each of 9 C57BL/6 mice (8-10 wks) were immunised subcutaneously with nmoles of lipidated [P25]-Lys(Pam$_2$Cys-Ser-Ser)-[SIINFEKL] (SIINFEKL disclosed as SEQ ID NO: 173) or non-lipidated [P25]-Lys-[SIINFEKL] (SIINFEKL disclosed as SEQ ID NO: 173) peptide in 100 µl volume of saline. In the case of lipidated peptide, lipid was attached between the two epitopes at the approximate centre of the molecule.

Peptides Comprising a CTL Epitope of Hepatitis C Virus Core Protein

Human monocyte-derived dendritic cells were incubated with lipopeptide [P25]-Lys(Pam$_2$Cys-Ser-Ser)-[HCV] (5 µg/mL) for 48 hours before staining with FITC-conjugated antibodies for HLA-DR, CD83 and CD86 before analysis by flow cytometry.

Challenge of Immunized Mice with Influenza Virus

Penthrane anesthetized mice previously immunized with peptides comprising CTL epitopes of influenza virus were challenged intranasally (i.n.) with $10^{4.5}$ PFU of infectious Mem 71 influenza virus. Each mouse received 50 µl of virus in the form of allantoic fluid diluted in PBS. At 5 days after challenge; the mice were killed by cervical dislocation, and the lungs were removed and transferred aseptically to bottles containing 1.5 ml of Hank's balanced salt solution supplemented with 100 U of penicillin, 100 µg of streptomycin, and 30 µg of gentamicin per ml. Lung homogenates were prepared by using a tissue homogenizer, and the cell material was pelleted by centrifugation at 300×g for 5 min. The supernatants were removed, divided into aliquots and stored at −70° C. until required. Titers of infectious virus in the lung supernatants were determined by plaque assay on monolayers of MDCK cells (Tannock et al, Infect. Immun. 431, 457-462, 1984).

Challenge of Immunized Mice with L. monocytogenes

Mice immunized s.c. with 9 nmol peptide immunogen or PBS, or i.v. with 1000 bacteria, were challenged by i.v. injection with bacteria 28 days after priming and the number of colony forming units of bacteria present in the liver determined 28 days after challenge.

Challenge of Immunised Mice with Tumour Cells.

Melanoma Challenge.

14 days after inoculation with non-lipidated (P25]-Lys-[SIINFEKL] (SIINFEKL disclosed as SEQ ID NO: 173) or lipidated peptide [P25]-Lys(Pam$_2$Cys-Ser-Ser)-(SIINFEKL] (SIINFEKL disclosed as SEQ ID NO: 173), 6 mice from each group were challenged with 2×10$^5$ melanoma cells expressing ovalbumin [B16-OVA] and therefore expressed the CTL epitope SIINFEKL (SEQ ID NO: 173) (Bellone, at al, J. Immunol. 165:2651-2656). Hair around the injection site was removed with an electric shaver prior to injection to facilitate measurement of the emerging tumors. Growing tumors were monitored, and the animals were sacrificed when tumor size reached 15 by 15 mm. Mean tumor area was calculated for each treatment group at the indicated number of days after the tumor challenge.

Lewis Lung Carcinoma Challenge.

Mice were injected with 3×10$^4$ Lewis Lung tumour cells that had been transfected with ovalbumin and therefore expressed the CTL epitope (Nelson et al., J. Immunol. 166: 5557-5566, 2001). Four days after receiving tumour cells, animals were inoculated with 20 nmoles of lipidated peptide [P25]-Lys(Pam$_2$Cys-Ser-Ser)-[SIINFEKL] (SIINFEKL disclosed as SEQ ID NO: 173), non-lipidated peptide [P25]-Lys-[SIINFEKL] (SIINFEKL disclosed as SEQ ID NO: 173) or with PBS subcutaneously in the base of the tail. A second dose of immunogen was administered eleven days after receiving the tumour cells. Animals were monitored for tumour incidence and survival; animals were euthanased when tumour area exceeded 100 mm$^2$.

Tetramer Staining of Peptide-Specific CD8+ T Cells

CD8$^+$ T cells specific for an immunodominant H-2K$^d$-restricted CTL epitope consisting of amino acid residues 147-155 of the nucleoprotein of influenza virus strain A/Puerto Rico/8/34 (PR8; H1N1) in the lipopeptide immunogen, as set forth in SEQ ID NO: 2, were identified using tetrameric complexes of the H-2K$^d$ glycoprotein with bound CTL peptide (TYQRTRALV; SEQ ID NO: 2) (Bodmer et al, Cell 52: 253-258, 1988; Sherman et al, J. Exp. Med. 175: 1221-1226, 1992).

The monomer was a gift from Professor Peter Doherty, Department of Microbiology and Immunology, University of Melbourne and was made at St. Jude Children's Research Hospital, Memphis Tenn., USA. Tetramer was made by incubating the monomer with Streptavidin-phycoerythrin (Molecular Probes, Eugene, Oreg., USA) at a 4:1 molar ratio.

Lymphocytes from the lung were first treated with 20 µL of normal mouse serum (NMS) for 5 mins at room temperature and then stained for 60 min with the tetrameric complexes at a 1:25 dilution. This was followed by staining with anti-CD8α, (53-6.7) conjugated with Allophycocyanin for 30 mins on ice and washed twice and analysed by a fluorescence-activated cell sorter (FACSort, Becton Dickinson, San Jose's, USA). The data were analysed by FlowJo (Tree Star, Inc, Calif., USA).

T-Cell Culture Medium

T-cell culture medium consisted of RPM1 1640 (CSL Ltd.) supplemented with 10% (vol/vol) heat-inactivated fetal calf serum, 2 mM L-glutamine, 2 mM sodium pyruvate, 30 µg of gentamicin/ml, 100 µg of streptomycin/ml, 100 IU of penicillin/ml, and 10$^{-4}$ M 2-mercaptoethanol.

Cytotoxic T-Cell Assays

Secondary effector cells were generated either from inguinal and popliteal lymph nodes of mice that had been immunized s.c. 7 days previously with lipopeptide immunogens or from spleen cells of mice primed at least 28 days previously with the lipopeptide immunogens. Briefly, $4\times10^7$ lymph node cells or spleen cells, depleted of erythrocytes by treatment with Tris-buffered ammonium chloride (0.15 M $NH_4Cl$ in 17 mM Tris-HCl at pH 7.2), were cultured with $10^7$ irradiated (2,200 rads, $^{60}Co$ source) virus-infected or lipopeptide-pulsed syngeneic spleen cells in 25-$cm^2$ tissue culture flasks (Falcon) containing 15 ml of T-cell culture medium. The virus-infected spleen cells had been preincubated at 37° C. for 30 min with 3,000 hemagglutinating units of either infectious Mem 71 or PR8 virus in 1 ml of serum-free RPM1 and washed once prior to addition to the flask. The lipopeptide-pulsed spleen cells had been preincubated at 37° C. for 60 min with 100 μg of the CTL lipopeptide/ml and also washed once prior to addition to the flask. After 5 days of culture at 37° C. in a humidified atmosphere containing 5% $CO_2$, the cells were washed three times and. used in $^{51}Cr$-release assays. The $^{51}Cr$-release assays were performed in triplicate as described previously (Harling-McNabb et al, *Int. Immunol.* 11, 1431-1439, 1999) by using P815 mastocytoma cells ($H-2^d$, DBA/2) as targets.

In Vivo Cytotoxic T.-Cell Assays

The ability of various peptide-based immunogens to induce epitope-specific CTL was determined in vivo. Groups of three mice were inoculated intranasally with various lipopeptides in 50 μl PBS and challenged with Mem71 on day 28. In order to analyze CTL determinant specific cytotoxicity in vivo, syngeneic spleen cells were pulsed with the CTL determinant and labelled with high intensity CFSE (2.5 μM). Antigen-specific lysis was controlled by co-injecting syngeneic spleen cells labelled with low intensity CFSE (0.25 μM). A mixture of $15\times10^6$ cells of each target cell population was injected intravenously on day 4 post-infection. The mice were killed 16 hr later and spleens were analysed for the presence of CFSE-high and CFSE-low cell populations by flow cytometry. A total of $1\times10^6$ lymphocytes were analysed for each sample. Individual mice are represented by the closed squares and the bars represent the geometric mean titre.

ELISPOT Assay for IFN-γ-Secreting Cells

CTL-specific IFN-γ-secreting cells were enumerated by an ELISPOT assay modified from that of Murali-Krishna et al, *Immunity* 8, 177-187, 1998. Flat-bottom polyvinyl chloride microtiter plates (96-well: Dynatech) were coated overnight with 50 μl of rat anti-(mouse IFN-γ) antibody (clone R4-14a2) at 5 μg/ml in PBS. Unoccupied sites on the wells were then blocked by incubation for 1 h with 10 mg of bovine serum albumin/ml in PBS; and the plates were washed three times with PBS containing 0.05% Tween 20 (PBST). Twofold dilutions of spleen or lymph node cells in T-cell medium were then added to the wells, together with $5\times10^5$ irradiated (2,200 rads, $^{60}Co$ source) syngeneic spleen cells from unimmunized mice and 10 U of recombinant human interleukin-2 (Pharmingen, San Diego, Calif.)/well. Cells were incubated at 37° C. in 5% $CO_2$ for 18 h the presence or absence of the CTL peptide at a concentration of 1 μg of peptide/ml. Cells were then lysed and removed by rinsing the plate, initially with distilled water and then PBST. Then, 50 μl of a 1/500 dilution of biotinylated anti-(mouse IFN-γ) antibody (clone XMG 1.2; Pharmingen) was added, and the plates were incubated at room temperature for 2 h. Plates were again washed, and 50 μl of streptavidin-alkaline phosphatase (Pharmingen; 1/400 dilution in 5 mg of bovine serum albumin/ml of PBST) was added to each well; the mixtures were then incubated for a further 2 h. The plates were washed. and 100 μl of ELISPOT substrate (Sedgwick et al, *J. Immunol. Methods* 57, 301-309, 1983) containing 1 mg of BCIP (5-bromo-4-chloro-3-indolylphosphate) per ml of 2-amino-2-methyl-1-propynol buffer (Sigma) was added to each well. When blue-green spots had developed, the plates were washed with water and dried, and the spots were counted with the aid of an inverted microscope.

DI Dendritic Cell Cultures

Dendritic cells (DC) were cultured in medium based on complete IDDM. This consisted of Iscove's Modified Dulbecco's Medium (IMDM) containing 25 mM HEPES and without alpha-thioglycerol or L-glutamine (JRH Bioscience, Lenexa, USA), supplemented with 10° A) (v/v) heat inactivated (56° C., 30 min) foetal calf serum (CSL Ltd., Parkville, Victoria, Australia), gentamicin (24 μg/mL), glutamine (2 mM), sodium pyruvate (2 mM), penicillin (100 IU/mL), streptomycin (180 μg/mL) and 2-mercaptoethanol (0.1 mM). For DC generation complete IMDM was further supplemented with 30% supernatant from cultured NIH/3T3 cells and 5% GM-CSF in the form of a supernatant from Ag8653 cells transfected with the GM-CSF gene (DC medium).

The culture method for immature dendritic cells was adapted from Winzler et al., *J. Exp Med.* 185, 317 (1997). Spleen cells from a BALB/c mouse were seeded at $1.5\times10^6$ cells per 55 mm dish (Techno-Plas, S.A., Australia) in 3 ml DC medium and incubated at 37° C. with 5% $CO_2$. All the equipment used for culturing was pyrogen free. The medium was changed every 4 days and all cells returned to the dish. On day 12, both suspended and weakly adherent cells were collected by forcefully pipetting and then aspirating the medium. The procedure was repeated with 2 ml of PBS. The remaining strongly adherent cells were discarded. The collected cells were pelleted by centrifugation and reseeded into a new dish. Cells were subsequently maintained on a 4 day alternating cycle of media change and passage. After 1 month of continuous culturing, the floating and semi-adherent cells took on the appearance and staining characteristics of immature DC and are referred to as D1 cells. Under these passage conditions the majority of cultured D1 cells maintain an immature phenotype characterized by an intermediate expression level of cell surface MHC class II molecules.

Flow Cytometric Analysis of D1 Cells

D1 cells ($1\times10^5$ cells per sample) were seeded in a new Petri dish with 1 mL of DC media and incubated with 0.0045 nmole of lipopeptide, dissolved in complete IMDM medium. Lipopolysaccharide (LPS) purified from *E. coli* serotype 0111:B4 (Difco, Detroit, Mich., USA, was used at 5 μg/mL as a positive control for DC maturation. After overnight incubation, the cells were harvested and washed once with PBS with 1% FCS. To prevent non-specific binding to FCγRII/III, the cells were pre-incubated with 20 μL of normal mouse serum for 5 mins at room temperature. The cells were then exposed to FITC-conjugated monoclonal antibody 14-4-4S ($IgG_{2a}$, anti-1-$E^{k,d}$; Ozato et al., *J. Immunol.*, 124, 533 (1980)) for 30 min on ice. Monoclonal antibody 36/1 (Brown et al., *Arch Virol* 114: 1, 1990), which is specific for the antigen of influenza virus from which the T-helper epitope is derived, was used as an isotype control. All antibodies were used at 2.5 μg/mL. The samples were washed once with PBS containing 1% FCS and fixed with PBS containing 4% paraformaldehyde on ice for 15 minutes. Flow cytometry analysis was performed using a FACSort (Becton Dickinson, San Jose, USA) and the data were analysed using FlowJo software (Tree Star, Inc., San Carlos, Calif., USA).

Human Dendritic Cell Cultures

Generation of Monocyte-Derived Dendritic Cells

Peripheral blood mononuclear cells (PMBCs) were prepared from buffy coat preparations obtained from blood donors (Red Cross Blood Bank, Melbourne, Australia) by Ficoll Paque (Amersham Pharmacia, Sweden) gradient separation. The cells were washed three-times in PBS and incubated with optimal amounts of murine anti-CD14 hybridoma supernatant (3C10, American Type Culture Collection) for 45 minutes on ice. After two washes, cells were further incubated with goat anti-murine IgG microbeads (Miltenyi Biotech, Germany) according to the manufacturer's protocol. CD14$^+$ monocytes were then positively selected by affinity purification using a magnet-activated cell sorting (MACS) column. Immature DC were generated by culturing the monocytes in GM-CSF and IL-4 (40 ng/ml and 20 ng/ml, respectively [Schering Plough, USA]) supplemented RPMI-1640 (Gibco, USA) containing 10% FCS(CSL, Australia), 2 mmol/L glutamine, 2 mmol/L sodium pyruvate, 100 U/ml penicillin, 100 µg/ml streptomycin, 30 µg/ml gentamicin and 0.1 mmol/L 2-mercaptoethanol. Cells were cultured for 5 days before use with half volume changes of media every 2 days.

Measurement of DC Maturation

The ability of peptide and lipopeptide-based immunogens to up-regulate the expression of MHC class II, CD83 and CD86 on human monocyte-derived dendritic cells was determined by incubating $5 \times 10^5$ cells per ml for 2 days in medium supplemented with GM-CSF and IL-4 and either LPS (5 µg/mL), non-lipidated peptide [Th]-Lys-[CTL] (5 µg/mL) or lipopeptide [Th]-Lys(Pam$_2$Cys-Ser-Ser)-[CTL] (5 µg/mL) for 48 hours. Phenotypic analysis of surface markers was performed by staining with fluorochrome-conjugated monoclonal antibodies to HLA-DR (G46-6 [L243]), CD83 (HB15e), CD86 (Cat. No. 2331 [FUN-1]) and appropriate isotype matched antibodies (MOPC-21 and G155-178) from Becton Dickinson (USA), according to the manufacturer's protocols. Cells were then washed, fixed in 1% formaldehyde and analysed on a flow cytometer. The histograms are representative of large granular cells gated on the forward and side scatter dot plot. The shaded regions of the histograms and the associated numerical values identify the percentage of cell populations expressing high levels of CD83, CD86 or HLA-DR.

EXAMPLE 2

Immunogenicity of Lipopeptides Comprising CTL Epitopes from Influenza Virus

Lipopeptides having a CTL epitope from influenza virus and in particular the lipopeptides [Th]-Lys(Pam$_2$Cys-Ser-Ser)-(CTL) and [Th]-Lys(Pam$_3$Cys-Ser-Ser)-[CTL], which comprise the amino acid sequence set forth in SEQ ID NO: 4 were tested for their ability to induce enhanced CTL-mediated viral clearance and to enhance dendritic cell maturation. As a negative control, a non-lipidated peptide having the amino acid sequence of SEQ ID NO: 4 was used in all experiments.

Viral Clearance

The lipopeptides elicited a higher level of viral clearance than non-lipidated peptides (FIGS. 3, 4a). Viral load in the lungs of mice primed with the lipopeptides and challenged with infectious Mem 71 virus 9 days later was reduced by 95% ([Th]-Lys(Pam$_3$Cys-Ser-Ser)-[CTL]; FIG. 3) or 99% ([Th]-Lys(Pam$_2$Cys-Ser-Ser)-[CTL]; FIG. 3) compared to samples from mice immunized with PBS alone. In contrast, non-lipidated peptide achieved only a 65% reduction in viral load ([Th]-Lys-(CTL); FIG. 3). Enhanced viral clearance was also observed in lipopeptide-inoculated animals that had been challenged with Mem 71 virus 28 days after the initial inoculation. In contrast, the ability to clear virus is significantly weaker at this time point in mice inoculated with the non-lipidated peptide.

As shown in FIG. 4b, there was also enhanced CD8$^+$ T cell activation in immunized mice receiving the lipopeptides referred to in the legend to FIG. 2, compared to mice receiving only non-lipidated peptide or PBS as seen by the number of CD8+ T cells found in the BAL fluids.

Dendritic Cell Maturation

The priming of naïve CD4+ T cells and CD8+ T cells in secondary lymphoid organs by dendritic cells is preceded by maturation of DC upon exposure to antigen epitope. This maturation is characterised by up-regulation of MHC products and co-stimulatory molecules on the DC surface. We therefore determined whether the various peptides and lipopeptides could differentially activate dendritic cells in an attempt to explain the different immunogenic properties of these vaccine candidates. The results of experiments in which a line of immature DC, D1 cells, were exposed to peptides, stained for surface expression of MHC class II molecules then analysed by flow cytometry, demonstrated that there was enhanced maturation of dendritic cells following their exposure to the peptides [Th]-Lys(Pam$_3$Cys-Ser-Ser)-[CTL] or [Th]-Lys(Pam$_2$Cys-Ser-Ser)-[CTL] compared to [Th]-Lys-[CTL] peptide or medium alone (FIG. 4c).

[Th]-Lys(Pam$_2$Cys-Ser-Ser)-[CTL] was the most effective and the non-lipidated peptide [Th]-Lys-[CTL] was the least effective in causing maturation of DC, with [Th]-Lys(Pam$_3$Cys-Ser-Ser)-[CTL] being nearly as effective as [Th]-Lys(Pam$_2$Cys-Ser-Ser)-[CTL] (FIG. 4c). The ability of the lipidated peptide [Th]-Lys(Pam$_2$Cys-Ser-Ser)-[CTL] to up-regulate class II expression was the same as for bacterial lipopolysaccharide (LPS). The non-lipidated peptide was unable to induce maturation of D1 cells greater than about 26%, a level that occurs spontaneously in culture. The relative abilities of these lipopeptides to induce maturation of D1 cells directly reflected their ability to induce CTL-mediated viral clearing responses and CD8+ T cells in the BAL.

Effects of Different Lipids on Cytotoxicity and T Cell Proliferation In Vitro and In Vivo The effects of conjugating different lipids, including Pam$_1$Cys, Pam$_2$Cys, Pam$_3$Cys, palmitic acid and cholesterol, to the peptide immunogen were also determined:

As shown in FIG. 5, viral load in the lungs of mice primed with Pam$_2$Cys-containing lipopeptides were lower than for mice primed with lipopeptides comprising the other lipids tested, suggesting that Pam$_2$Cys is preferred for conferring protection against virus. All lipids however, offered some protection against virus. This effect was also reflected in the IFN-gamma CD8+ T cell count (FIG. 6). Collectively, these data suggest that it is important to attach the lipid to the cysteine glycerol residue, as in the [Th]-Lys(Pam$_2$Cys-Ser-Ser)-[CTL] epitope structure, for maximum cytotoxic effect.

In tetramer assays, the highest number of tetramer positive CD8+ T cells per lung were observed for lipopeptides wherein the lipid moiety was added to the epsilon amino group of an internal lysine residue (e.g., lipopeptides ITIA-Lys(PamiCysSer-Ser)-[CTL], [Th]-1-Ys(Pam2Cys-Ser-Ser)-[CTL], [TIA-Lys(Pam3Cys-Ser-Ser)-[CTL], and [Th]-Lys(Chol2Lys-Ser-Ser)-[CTL] in FIG. 7) compared to nonlipidated peptide or lipopeptide having lipid added to the N-terminus of the peptide (e.g., construct Pal2LysLys[Th]-[CTL] in FIG. 7). These data also confirm that the positioning of the lipid internal to the peptide, by attachment to the epsilon amino group of an internal lysine residue, enhances cytotoxic activity of the CTL epitope.

To analyze CTL determinant specific cytotoxicity in vivo, mice were inoculated intranasally with 9 nmoles of various lipopeptides in PBS and challenged with Mem71 virus on day 28. CTL determinant-specific cytotoxicity in vivo was measured using syngeneic spleen cells pulsed with the CTL determinant and labelled with high intensity CFSE. Non-pulsed spleen cells labelled with low intensity CFSE were used as a control. A mixture of cells of each target cell population was injected intravenously on day 4 post-infection. The mice were killed 16 hr later and spleens were analysed for the presence of CFSE-high and CFSE-low cell populations by flow cytometry. A total of $1 \times 10^6$ lymphocytes were analysed for each sample. Data in FIG. 8 is a graphical representation showing cytotoxic T cell activity in naïve mice. FIG. 9 indicates that the lipopeptide [Th]-Lys(Pam$_2$Cys-Ser-Ser)-(CTL) comprising the CD4+ T-helper epitope set forth in SEQ ID NO: 1 and the H-2$^d$-restricted CIL epitope set forth in SEQ ID NO: 2, induced significant cytotoxicity in vivo.

As shown in FIG. 10, lipopeptides have higher activity than non-lipidated peptide, with the lipopeptides designated [Th]-Lys(Pam$_1$Cys-Ser-Ser)-[CTL], [Th]-Lys(Pam$_2$Cys-Ser-Ser)-[CTL] and [Th]-Lys(Pam$_3$Cys-Ser-Ser)-[CTL] providing a marked enhancement of specific lysis in vivo compared to the non-lipidated peptide [Th]-Lys-(CTL) and other lipopeptides tested. These data again confirm that positioning of the lipid internal to the peptide, by attachment to the epsilon amino group of an internal lysine residue, enhances cytotoxic activity of the CTL epitope in vivo.

EXAMPLE 3

Immunogenicity of Lipopeptides Comprising a CTL Epitope from *L. monocytogenes*

A lipopeptide having a CTL epitope from *L. monocytogenes* and in particular the lipopeptide [P25]-Lys(Pam$_2$Cys-Ser-Ser)-[LLO91-99] comprising the amino acid sequence set forth in SEQ ID NO: 175 was tested for its ability to induce a CD8+ T cell response, and to protect against a challenge with *L. monocytogenes*. As a negative control, PBS or a non-lipidated peptide having the amino acid sequence of SEQ ID NO: 175 was used in all experiments. Isolated bacteria were used as a positive control.

IFN-γ Production by Splenocytes

The lipopeptide tested in this study induced a specific CD8+ T cell response against the immunizing CTL epitope, as evidenced by the enhanced number of IFN-γ producing splenocytes present in mice immunized with lipidated peptide relative to non-lipidated peptide. Mice immunized with 9 nmoles lipidated peptide vaccine [P25]-Lys (Pam$_2$Cys-Ser-Ser)-[LLO91-99] comprising the amino acid sequence set forth in SEQ ID NO: 175 produced about 15-fold more IFN-γ producing cells per million splenocytes than mice receiving non-lipidated peptide or a PBS control, indicating an enhanced activation of IFN-γ producing CD8+ T cells in the mice. receiving the lipidated peptide (FIG. 11).

Protection Against Challenge with Isolated Bacteria

Data in FIG. 12 indicate that the lipidated [P25]-Lys (Pam$_2$Cys-Ser-Ser)-[LLO91-99] peptide successfully provides protection against a subsequent challenge with whole bacteria. A significantly enhanced protection was also observed in mice immunized with the lipidated [P25]-Lys (Pam$_2$Cys-Ser-Ser)-(LLO91-99] peptide relative to mice immunized with non-lipidated [P25]-Lys-[LLO91-99] peptide or PBS (i.e. non-immunized mice).

EXAMPLE 4

Protection Against Challenge with Tumour Cells

Protection Against Challenge with Melanoma Cells

The ability of the lipopeptide vaccine containing the ovalbumin CTL epitope (SIINFEKL) (SEQ ID NO: 173) to induce protection against melanoma cells expressing this CTL epitope (B16-OVA cells) was assessed. IFN-γ production was determined in mice inoculated with lipopeptide comprising a CDV-F T-helper epitope (P25) and a CTL epitope (SIINFEKL) (SEQ ID NO: 173) of ovalbumin linked via the epsilon amino group of an internal lysine residue positioned between said epitopes to Pam$_2$Cys (i.e. the peptide [P25]-Lys(Pam$_2$Cys-Ser-Ser)-[SIINFEKL](SIINFEKL disclosed as SEQ ID NO: 173) listed in FIG. 2 and based upon SEQ ID NO: 174). C57BL/6 mice were vaccinated with 20 nmoles lipidated peptide [P25]-Lys(Pam$_2$Cys-Ser-Ser)-[SIINFEKL] (SIINFEKL disclosed as SEQ ID NO: 173), non-lipidated peptide [P25]-Lys-[SIINFEKL] (SIINFEKL disclosed as SEQ ID NO: 173) or with PBS subcutaneously in the base of the tail. Mice were then challenged subcutaneously on the back 14 days later with B16-OVA cells. Splenocytes were obtained from the inoculated animals and stimulated in vitro with the CTL epitope having the sequence SIINFEKL (SEQ ID NO: 173) and the number of IFN-γ producing cells per 1,000,000 splenocytes was measured. Data show enhanced numbers of IFN-γ producing cells for mice inoculated with lipopeptide (Table 1), indicating an enhanced ability of the lipopeptides to activate T cells relative to non-lipidated peptide.

Importantly, control of tumour growth was elicited by immunisation with lipopeptide compared to mice immunized with the non-lipidated peptide [P25)-Lys-[SIINFEKL] (SIINFEKL disclosed as SEQ ID NO: 173) or PBS alone (FIG. 13). No tumour growth was observed over a 15 day period in mice immunised with [P25]-Lys(Pam$_2$Cys-Ser-Ser)SIINFEKL] (SIINFEKL disclosed as SEQ ID NO: 173). Conversely, tumours of greater than 75 mm$^2$ in diameter were observed in mice immunised with [P25]-Lys-[SIINFEKL] (SIINFEKL disclosed as SEQ ID NO: 173) or PBS alone. Together, these data confirm the protective ability of the lipopeptide compared to non-lipidated peptide in protection against tumours.

TABLE 1

Numbers of IFN-γ secreting splenocytes in representative melanoma samples receiving [P253-Lys(Pam$_2$Cys-Ser-Ser)-[SIINFEKL] (SIINFEKL disclosed as SEQ ID NO: 173) lipopeptide compared to non-lipidated [P25]-Lys-[SIINFEKL] (SIINFEKL disclosed as SEQ ID NO: 173) peptide or PBS

PEPTIDE/LIPOPEPTIDE IMMUNOGEN

| [P25]-Lys(Pam$_2$Cys-Ser-Ser)-[SIINFEKL | [P25]-Lys-[SIINFEKL] | PBS |
|---|---|---|
| No. IFN-γ secreting splenocytes per 10$^6$ splenocytes | | |
| 284 | 18 | 5 |
| 205 | 14 | 0 |
| 192 | 10 | 0 |

TABLE 1-continued

Numbers of IFN-γ secreting splenocytes in
representative melanoma samples receiving
[P253-Lys(Pam₂Cys-Ser-Ser)-[SIINFEKL]
(SIINFEKL disclosed as SEQ ID NO: 173)
lipopeptide compared to non-lipidated
[P25]-Lys-[SIINFEKL] (SIINFEKL disclosed
as SEQ ID NO: 173) peptide or PBS
PEPTIDE/LIPOPEPTIDE IMMUNOGEN

| [P25]-Lys(Pam₂Cys-Ser-Ser)-[SIINFEKL] | [P25]-Lys-[SIINFEKL] | PBS |
|---|---|---|
| Average | | |
| 227 | 14 | 3 |
| Std. deviation | | |
| 49 | 4 | 24 |

Protection Against Challenge with Lewis Lung Tumour Cells

The ability of the lipopeptide to provide protection against Lewis Lung tumor development in animals in vivo was also tested. Mice were injected with $3 \times 10^4$ Lewis Lung tumour cells transfected with ovalbumin and therefore expressing the CTL epitope SIINFEKL (SEQ ID NO: 173) (Nelson et al., *J. Immunol.* 166: 5557-5566, 2001). Four days after receiving tumour cells, animals were inoculated subcutaneously in the base of the tail with 20 nmoles lipidated peptide [P25]-Lys(Pam₂Cys-Ser-Ser)-[SIINFEKL] (SIINFEKL disclosed as SEQ ID NO: 173), or alternatively, non-lipidated peptide [P25]-Lys-[SIINFEKL] (SIINFEKL disclosed as SEQ ID NO: 173) or PBS. A second and similar dose of immunogen was administered eleven days after receiving the tumour cells. Data in FIG. 14 indicate that the percentage of animals with fewer lesions developing was significantly higher for animals receiving the lipopeptide compared to animals receiving the non-lipidated peptide or PBS. As shown in FIG. 15, animals receiving the lipopeptide immunogen also survived for longer than those receiving the non-lipidated peptide or PBS. These data further confirm the protective ability of the lipopeptide compared to non-lipidated peptide for protection against tumours.

EXAMPLE 5

Enhanced Expression of MHC Class II, CD83 and CD86 on Human Dendritic Cells Following Administration of a Lipopeptide Comprising a CDV-F T-Helper Epitope and a CTL Epitope from Hepatitis C Virus The lipopeptide [P251-Lys(Pam₂Cys-Ser-Ser)HCV] described in the legend to FIG. 2 was tested for its ability to up-regulate the expression of MHC class II, CD83 and CD86 on human dendritic cells. Human monocyte-derived dendritic cells were incubated with media alone, LPS (5 µg/mL), non-lipidated peptide [P25]-Lys-[HCV] (5 µg/mL) or lipopeptide [P25]-Lys(Pam₂Cys-Ser-Ser)-[HCV] (5 µg/mL) for 48 hours before staining with FITC-conjugated antibodies for HLA-DR, CD83 and CD86 before analysis by flow cytometry. Data shown in FIG. 16 demonstrate a higher percentage of dendritic cell populations that express HLA-DR, CD83 and CD86 antigens on their cell surface are present following treatment with lipidated peptide than following treatment with non-lipidated peptide or PBS alone. The ability of the lipopeptide to induce maturation of human dendritic cells directly reflected the immunogenic ability of the lipopeptide compared to the non-lipidated peptide, providing a possible mechanism for immunogenicity.

EXAMPLE 6

Discussion

In this study we describe the assembly of a variety of lipopeptide immunogens composed of a CD4⁺ T cell epitope, a CD8⁺ CTL epitope and Pam₃Cys or Pam₂Cys linked thereto via the epsilon amino group of an internal lysine residue.

The precise nature of the lipid moiety in generating an immune response was not shown to be critical, because a range of lipids, including cholesterol, palmitic acid, Pam₁Cys, Pam₂Cys, and Pam₃Cys were shown to successfully elicit T cell proliferation and cytotoxicity. However, significant differences were observed in terms of protection and IFN-gamma production, at least in the case of lipopeptides directed against influenza virus, suggesting that lipid structure may be an important consideration in vivo. In particular, at least for vaccines incorporating the influenza virus CTL epitope, Pam₂Cys linked to the epsilon amino group of an internal lysine residue in the peptide were most effective in conferring protection, suggesting that a linkage to the cysteine glycerol is preferred.

The lipopeptides of the invention are effective in enhancing the CD8+ T cell responses of immunized animals against bacterial and viral pathogens and also against tumour cells. Given the success of the self-adjuvanting peptides exemplified herein to protect against viral and bacterial pathogens as well as tumour cells, it is reasonable to expect that this technology is generally applicable to a wide range of vaccination protocols.

Insertion of serine residues between the lipid moiety and the peptide sequence does not adversely affect the potency of the resulting Pam₂Cys-containing immunogens.

The lipopeptides can trigger an immune response in the absence of additional adjuvant and can be delivered by both parenteral and non-parenteral routes, particularly intranasally.

Taken together, the data provided herein demonstrate that placement of a wide range of lipids, including but not limited to Pam₂Cys and Pam₃Cys, between the CTL epitope and the T helper epitope, at the approximate centre of a totally synthetic peptide vaccine increases the immunogenicity of the vaccine.

The invention claimed is:

1. A lipopeptide comprising a polypeptide conjugated to one or more lipid moieties wherein:
   (i) said polypeptide comprises an amino acid sequence wherein the linkages between the amino acids making up the amino acid sequence consist of alpha-amino acid linkages and the amino acid sequence comprises:
       (a) the amino acid sequence of a T helper cell (Th) epitope and the amino acid sequence of a cytotoxic T cell (CTL) epitope, wherein said amino acid sequences are different; and
       (b) one or more internal lysine residues or internal lysine analog residues for covalent attachment of each of said lipid moieties via the epsilon-amino group or terminal side-chain group of said lysine or lysine analog; and
   (ii) each of said one or more lipid moieties is covalently attached to an epsilon-amino group of said one or more internal lysine residues or to a terminal side-chain group of said one or more internal lysine analog residues, wherein an internal lysine residue or internal lysine analog residue to which a lipid moiety is attached is positioned in the polypeptide amino acid sequence between the Th epitope and the CTL epitope.

2. The lipopeptide of claim 1 wherein the lipid moiety has a structure of General Formula (VII):

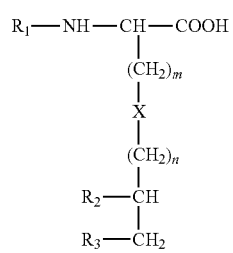

Formula (VII)

wherein:
   (i) X is selected from the group consisting of sulfur, oxygen, disulfide (—S—S—), and methylene (—CH$_2$—), and amino (—NH—);
   (ii) m is an integer being 1 or 2;
   (iii) n is an integer from 0 to 5;
   (iv) R$_1$ is selected from the group consisting of hydrogen, carbonyl (—CO—), and R'—CO— wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group;
   (v) R$_2$ is selected from the group consisting of R'—CO—O—, R'—O—, R'—O—CO—, R'—NH—CO—, and R'—CO—NH—, wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group; and
   (vi) R$_3$ is selected from the group consisting of R'—CO—O—, R'—O—, R'—O—CO—, R'—NH—CO—, and R'—CO—NH—, wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group;
   and wherein each of R$_1$, R$_2$ and R$_3$ are the same or different.

3. The lipopeptide of claim 2 wherein X is sulfur; m and n are both 1; R$_1$ is selected from the group consisting of hydrogen, and R'—CO—, wherein R' is an alkyl group having 7 to 25 carbon atoms; and R$_2$ and R$_3$ are selected from the group consisting of R'—CO—O—, R'—O—, R'—O—CO—, R'—NH—CO—, and R'—CO—NH—, wherein R' is an alkyl group having 7 to 25 carbon atoms.

4. The lipopeptide of claim 3 wherein R' is selected from the group consisting of: palmitoyl, myristoyl, stearoyl, lauroyl, octanoyl, decanoyl, and cholesterol.

5. The lipopeptide of claim 2 wherein the lipid is contained within a lipoamino acid moiety selected from the group consisting of: Pam$_1$Cys, Pam$_2$Cys, Pam$_3$Cys, Chol$_2$Lys, Ste$_2$Cys, Lau$_2$Cys, and Oct$_2$Cys.

6. The lipopeptide of claim 1 wherein the lipid moiety has the following General Formula (VIII):

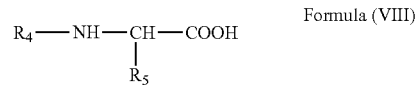

Formula (VIII)

wherein:
   (i) R$_4$ is selected from the group consisting of: (i) an alpha-acyl-fatty acid residue consisting of between about 7 and about 25 carbon atoms; (ii) an alpha-alkyl-beta-hydroxy-fatty acid residue; (iii) a beta-hydroxy ester of an alpha-alkyl-beta-hydroxy-fatty acid residue; and (iv) a lipoamino acid residue; and
   (ii) R$_5$ is hydrogen or the side chain of an amino acid residue.

7. The lipopeptide of claim 1 wherein the lipid moiety is separated from the peptide moiety by a spacer.

8. The lipopeptide of claim 7 wherein the spacer comprises arginine, serine or 6-aminohexanoic acid.

9. The lipopeptide of claim 1 wherein the T-helper epitope is a T-helper epitope of influenza virus haemagglutinin or a T-helper epitope of canine distemper virus F (CDV-F) protein.

10. The lipopeptide of claim 9 wherein the T-helper epitope of influenza virus haemagglutinin comprises the amino acid sequence set forth in SEQ ID NO: 1.

11. The lipopeptide of claim 9 wherein the T-helper epitope of CDV-F protein comprises the amino acid sequence set forth in SEQ ID NO: 20.

12. The lipopeptide of claim 1 wherein the CTL epitope is from an immunogenic protein, lipoprotein, or glycoprotein of a virus.

13. The lipopeptide according to claim 12 wherein the virus is influenza virus.

14. The lipopeptide according to claim 12 wherein the virus is hepatitis C virus.

15. The lipopeptide of claim 1 wherein the CTL epitope is from an immunogenic protein, lipoprotein, or glycoprotein of a prokaryotic organism.

16. The lipopeptide of claim 1 wherein the CTL epitope is from an immunogenic protein, lipoprotein, or glycoprotein of a eukaryotic organism.

17. The lipopeptide according to claim 16 wherein the CTL epitope is from an ovalbumin protein of a mammal or a tumor cell.

18. A composition comprising the lipopeptide of claim 1 and a pharmaceutically acceptable excipient or diluent.

* * * * *

SEQUENCE LISTING

<160> NUMBER OF SEQ ID NOS: 177

<210> SEQ ID NO 1
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Ala Leu Asn Asn Arg Phe Gln Ile Lys Gly Val Glu Leu Lys Ser
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Tyr Gln Arg Thr Arg Ala Leu Val
1               5

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Asn Asn Arg Phe Gln Ile Lys Gly Val Glu Leu Lys Ser Thr
1               5                   10                  15

Tyr Gln Arg Thr Arg Ala Leu Val
            20

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Asn Asn Arg Phe Gln Ile Lys Gly Val Glu Leu Lys Ser Lys
1               5                   10                  15

Thr Tyr Gln Arg Thr Arg Ala Leu Val
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Ile Pro Asn Ala Ser Leu Ile Glu Asn Cys Thr Lys Ala Glu
1               5                   10                  15

Leu Lys Thr Tyr Gln Arg Thr Arg Ala Leu Val
            20                  25

<210> SEQ ID NO 6
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Lys Leu Ile Pro Asn Ala Ser Leu Ile Glu Asn Cys Thr Lys Ala Glu
1               5                   10                  15

Leu Lys Asn Leu Val Pro Met Val Ala Thr Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Glu Leu Gly Glu Tyr Glu Lys Leu Leu Asn Ser Val Leu Glu Pro
1               5                   10                  15

Ile Lys Asn Leu Val Pro Met Val Ala Thr Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ala Ala Gln Ile Thr Ala Gly Ile Ala Leu His Gln Ser Asn Leu
1               5                   10                  15

Asn Lys Asn Leu Val Pro Met Val Ala Thr Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Arg Tyr Ile Ala Thr Asn Gly Tyr Leu Ile Ser Asn Phe Asp Glu
1               5                   10                  15

Ser Lys Asn Leu Val Pro Met Val Ala Thr Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Ile Pro Asn Ala Ser Leu Ile Glu Asn Cys Thr Lys Ala Glu
1               5                   10                  15

Leu Lys Tyr Leu Leu Glu Met Leu Trp Arg Leu
            20                  25
```

```
<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Glu Leu Gly Glu Tyr Glu Lys Leu Leu Asn Ser Val Leu Glu Pro
1               5                   10                  15

Ile Lys Tyr Leu Leu Glu Met Leu Trp Arg Leu
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Ala Ala Gln Ile Thr Ala Gly Ile Ala Leu His Gln Ser Asn Leu
1               5                   10                  15

Asn Lys Tyr Leu Leu Glu Met Leu Trp Arg Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Arg Tyr Ile Ala Thr Asn Gly Tyr Leu Ile Ser Asn Phe Asp Glu
1               5                   10                  15

Ser Lys Tyr Leu Leu Glu Met Leu Trp Arg Leu
            20                  25

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ala Leu Asn Asn Arg Phe Gln Ile Lys Gly Val Glu Leu Lys Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Ser Glu Ile Lys Gly Val Ile Val His Arg Leu Glu Gly Val
1               5                   10                  15
```

```
<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ala Ala Gln Ile Thr Ala Gly Ile Ala Leu His Gln Ser Asn Leu
1               5                   10                  15

Asn

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Gly Thr Asp Asn Val His Tyr Lys Ile Met Thr Arg Pro Ser His
1               5                   10                  15

Gln

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Lys Ile Met Thr Arg Pro Ser His Gln Tyr Leu Val Ile Lys Leu
1               5                   10                  15

Ile

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser His Gln Tyr Leu Val Ile Lys Leu Ile Pro Asn Ala Ser Leu Ile
1               5                   10                  15

Glu

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Leu Ile Pro Asn Ala Ser Leu Ile Glu Asn Cys Thr Lys Ala Glu
1               5                   10                  15
```

Leu

```
<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Ile Glu Asn Cys Thr Lys Ala Glu Leu Gly Glu Tyr Glu Lys Leu
1               5                   10                  15

Leu

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Glu Leu Gly Glu Tyr Glu Lys Leu Leu Asn Ser Val Leu Glu Pro
1               5                   10                  15

Ile

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Leu Leu Asn Ser Val Leu Glu Pro Ile Asn Gln Ala Leu Thr Leu
1               5                   10                  15

Met

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Pro Ile Asn Gln Ala Leu Thr Leu Met Thr Lys Asn Val Lys Pro
1               5                   10                  15

Leu

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Leu Met Thr Lys Asn Val Lys Pro Leu Gln Ser Leu Gly Ser Gly
1               5                   10                  15
```

Arg

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Pro Leu Gln Ser Leu Gly Ser Gly Arg Arg Gln Arg Arg Phe Ala
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Arg Arg Gln Arg Arg Phe Ala Gly Val Val Leu Ala Gly Val
1               5                   10                  15

Ala

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Ala Gly Val Val Leu Ala Gly Val Ala Leu Gly Val Ala Thr Ala
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Val Ala Leu Gly Val Ala Thr Ala Ala Gln Ile Thr Ala Gly Ile
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ile Ala Leu His Gln Ser Asn Leu Asn Ala Gln Ala Ile Gln Ser

```
1               5                   10                  15
Leu

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Leu Asn Ala Gln Ala Ile Gln Ser Leu Arg Thr Ser Leu Glu Gln
1               5                   10                  15
Ser

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Leu Arg Thr Ser Leu Glu Gln Ser Asn Lys Ala Ile Glu Glu
1               5                   10                  15
Ile

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Gln Ser Asn Lys Ala Ile Glu Glu Ile Arg Glu Ala Thr Gln Glu
1               5                   10                  15
Thr

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ser Lys Thr Gln Thr His Thr Gln Gln Asp Arg Pro Pro Gln Pro
1               5                   10                  15
Ser

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Gln Pro Ser Thr Glu Leu Glu Glu Thr Arg Thr Ser Arg Ala Arg His
1               5                   10                  15

Ser
```

```
<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg His Ser Thr Thr Ser Ala Gln Arg Ser Thr His Tyr Asp Pro Arg
1               5                   10                  15

Thr
```

```
<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Arg Thr Ser Asp Arg Pro Val Ser Tyr Thr Met Asn Arg Thr Arg
1               5                   10                  15

Ser
```

```
<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Arg Ser Arg Lys Gln Thr Ser His Arg Leu Lys Asn Ile Pro Val
1               5                   10                  15

His
```

```
<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Glu Leu Leu Ser Ile Phe Gly Pro Ser Leu Arg Asp Pro Ile Ser
1               5                   10                  15

Ala
```

```
<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

Pro Arg Tyr Ile Ala Thr Asn Gly Tyr Leu Ile Ser Asn Phe Asp Glu
1               5                   10                  15

Ser

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Ile Arg Gly Asp Thr Ser Ser Cys Ala Arg Thr Leu Val Ser Gly
1               5                   10                  15

Thr

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Glu Ser Ser Cys Val Phe Val Ser Glu Ser Ala Ile Cys Ser Gln
1               5                   10                  15

Asn

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ser Thr Ile Ile Asn Gln Ser Pro Asp Lys Leu Leu Thr Phe Ile
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Pro Asp Lys Leu Leu Thr Phe Ile Ala Ser Asp Thr Cys Pro Leu
1               5                   10                  15

Val

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Ser Thr Ala Pro Pro Ala His Gly Val Thr Ser Ala Pro Asp Thr Arg
1               5                   10                  15

Ala Pro Gly Ser Thr Ala Pro Pro
            20

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Val Thr Ser Ala Pro Asp Thr Arg Pro Ala Pro Gly Ser Thr Ala
1               5                   10                  15

Ser Ser Leu

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Val Thr Ser Ala Pro Asp Thr Arg Pro Ala Pro Gly Ser Thr Ala
1               5                   10                  15

Ser Leu

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ala Pro Pro Ala His Gly Val Thr Ser Ala Pro Asp Thr Arg Pro
1               5                   10                  15

Ala Pro Gly Ser Thr Ala Pro Pro Lys Lys Gly
            20                  25

<210> SEQ ID NO 49
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Thr Ala Pro Pro Ala His Gly Val Thr Ser Ala Pro Asp Thr Arg
1               5                   10                  15

Pro Ala Pro Gly Ser Thr Ala Pro Pro Lys
            20                  25

<210> SEQ ID NO 50
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 50

Gly Val Ala Glu
1

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Ser Gly Val Ala Glu Thr Thr Asn
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ala Lys Ser Lys Lys Phe Pro Ser Tyr Thr Ala Thr Tyr Gln Phe
1               5                   10                  15

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Pro Lys Asp Glu Leu Asp Tyr Glu Asn Asp Ile Glu Lys Lys Ile
1               5                   10                  15

Cys Lys Met Glu Lys Cys Ser
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ile Glu Lys Lys Ile Cys Lys Met Glu Lys Cys Ser Ser Val Phe
1               5                   10                  15

Asn Val Val Asn Ser
            20

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 55

Lys Pro Ile Val Gln Tyr Asp Asn Phe
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ile Ser Tyr Tyr Glu Lys Val Leu Ala Lys Tyr Lys Asp Asp Leu
1               5                   10                  15

Glu

<210> SEQ ID NO 57
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Phe Thr Tyr Met Ile Asn Phe Gly Arg Gly Gln Asn Tyr Trp Glu
1               5                   10                  15

His Pro Tyr Gln Lys Ser
            20

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Gln Pro Lys Gln Tyr Glu Gln His Leu Thr Asp Tyr Glu Lys Ile
1               5                   10                  15

Lys Glu Gly

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Met Trp Gln Glu Val Gly Lys Ala Met
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Ala Pro Thr Lys Ala Lys Arg Arg Val Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Thr Arg Pro Asn Asn Asn Thr Arg Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Val Tyr Tyr Gly Val Pro Val Trp Lys
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Pro Val Val Ser Thr Gln Leu Leu
1               5

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Leu Tyr Asn Thr Val Ala Thr Leu Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Leu Arg Ser Leu Tyr Asn Thr Val Ala
1               5                   10

<210> SEQ ID NO 66
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Lys Ile Arg Leu Arg Pro Gly Gly Lys Lys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Arg Leu Arg Pro Gly Gly Lys Lys Lys
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Leu Arg Pro Gly Gly Lys Lys Lys
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Pro Gly His Lys Ala Arg Val Leu Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Pro Ile Glu Thr Val Pro Val Lys Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Leu Lys Glu Pro Val His Gly Val Tyr
1               5                   10
```

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ile Phe Gln Ser Ser Met Thr Lys
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Pro Ala Ile Phe Gln Ser Ser Met Thr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Val Arg Asp Gln Ala Glu His Leu Lys
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Pro Lys Val Lys Gln Trp Pro Leu Thr
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Tyr Gln Arg Thr Arg Ala Leu Val
1               5

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Thr Tyr Gln Arg Thr Arg Ala Leu Val Arg Thr Gly Met Asp Pro
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Ala Ser Asn Glu Asn Met Asp Ala Met Glu Ser Ser Thr Leu
1               5                   10                  15

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Ala Val Tyr Asn Phe Ala Thr Met
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Val Lys Trp Arg Met Thr Thr Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Phe Ser Asp Gly Arg Val Ala Cys
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Pro Ala Pro Ala Gly Pro Ile Val
1               5

<210> SEQ ID NO 83
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Thr Tyr Ser Ala Gly Ile Val Gln Ile
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Leu Asp Phe Val Arg Phe Met Gly Val
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Asn Gly Ala Leu Ala Ile Asn Thr Phe
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Ser Ser Asp Gly Arg Val Ala Cys
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ser Ser Glu Gly Arg Val Ala Cys
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Ser Ser Asp Gly Arg Val Pro Cys
1               5
```

```
<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Ser Ser Asp Gly Leu Val Ala Cys
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Ser Ser Asp Gly Gln Val Ala Cys
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Ser Ser Asp Gly Arg Val Val Cys
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Pro Ala Pro Pro Val Gly Pro Ile Val
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Glu Ile Thr Pro Tyr Glu Pro Thr Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 94

Val Glu Ile Thr Pro Tyr Glu Pro Thr Trp
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Glu Leu Thr Pro Tyr Lys Pro Thr Trp
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Arg Ile Tyr Asp Leu Ile Lys Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Lys Ile Tyr Asp Leu Ile Glu Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Pro Tyr Leu Phe Trp Leu Ala Gly Ile
1               5

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Ser Leu Tyr Asn Leu Arg Arg Gly Thr Ala Leu Ala
1               5                   10

<210> SEQ ID NO 100
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Thr Pro Leu Ile Pro Leu Thr Ile Phe
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Val Phe Tyr Asn Ile Pro Pro Met Pro Leu
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Glu Ile Thr Pro Tyr Lys Pro Thr Trp
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Val Ser Phe Ile Glu Phe Val Gly Trp
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Phe Arg Lys Ala Gln Ile Gln Gly Leu
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Leu Arg Gly Arg Ala Tyr Gly Leu
```

```
<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Ala Lys Trp Arg Leu Gln Thr Leu
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Val Arg Asp Arg Leu Ala Arg Leu
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Pro Leu His Glu Gln His Gly Met
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Leu Ala Ala Gln Gly Met Ala Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Pro Pro Ile Phe Ile Arg Arg Leu
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 111

Arg Leu Arg Ala Glu Ala Gly Val Lys
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Val Thr Asp Phe Ser Val Ile Lys
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Val Phe Asp Arg Lys Ser Asp Ala Lys
1               5                   10

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Pro Thr Gln Ala Pro Val Ile Gln Leu Val His Ala Val Tyr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Leu Pro Gly Pro Gln Val Thr Ala Val Leu Leu His Glu Glu Ser
1               5                   10                  15

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Glu Pro Ala Ser Thr Glu Pro Val His Asp Gln Leu Leu
1               5                   10

<210> SEQ ID NO 117

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Tyr Ser Ile Phe Phe Asp Tyr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Val Leu Leu His Glu Glu Ser Met
1               5

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Arg Ala Arg Ser Leu Ser Ala Glu Arg Tyr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Glu Asn Leu Leu Asp Phe Val Arg Phe
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Glu His Val Ile Gln Asn Ala Phe
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
Arg Arg Ile Tyr Asp Leu Ile Glu Leu
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Pro Arg Ala Pro Ile Arg Pro Ile
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Gly Gly Val Gly Trp Arg His Trp
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Leu Gly Gly Leu Leu Thr Met Val
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Arg Arg Trp Arg Arg Leu Thr Val
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Lys Phe Lys Gln Leu Leu
1               5

<210> SEQ ID NO 128
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 128

Arg Lys Cys Cys Arg Ala Lys Phe Lys Gln Leu Leu Gln His Tyr Arg
1               5                   10                  15

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Leu Leu Glu Met Leu Trp Arg Leu
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Phe Leu Glu Ile Leu Trp Gly Leu
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Leu Leu Glu Ile Leu Trp Arg Leu
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Leu Gln Gln Asn Trp Trp Thr Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Leu Leu Leu Ala Leu Leu Phe Trp Leu
1               5
```

```
<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Leu Val Asp Leu Leu Trp Leu Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Leu Leu Ile Ala Leu Trp Asn Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Leu Leu Leu Phe Leu Ala Ile Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Leu Leu Val Asp Leu Leu Trp Leu
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Leu Trp Leu Leu Leu Phe Leu Ala
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139
```

```
Ile Leu Leu Ile Ile Ala Leu Tyr Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Val Leu Phe Ile Phe Gly Cys Leu Leu
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Leu Gly Ala Thr Ile Trp Gln Leu
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ile Leu Tyr Phe Ile Ala Phe Ala Leu
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Leu Val Ile Val Thr Thr Phe Val
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Met Ile Ile Pro Leu Ile Asn Val
1               5

<210> SEQ ID NO 145
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 145

Thr Leu Phe Ile Gly Ser His Val Val
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Ile Pro Glu Thr Val Pro Tyr Ile
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Leu Gln Trp Ala Ser Leu Ala Val
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Leu Thr Pro His Thr Lys Ala Val
1               5

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Val Leu Gly Pro Ile Ser Gly His Val Leu Lys
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Thr Ser Gln Tyr Arg Ile Gln Gly Lys Leu
1               5                   10
```

-continued

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Phe Val Phe Pro Thr Lys Asp Val Ala Leu Arg
1               5                   10

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Phe Pro Thr Lys Asp Val Ala Leu
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Leu Val Pro Met Val Ala Thr Val
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Met Leu Asn Ile Pro Ser Ile Asn Val
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ile Phe Ala Glu Leu Glu Gly Val
1               5

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 156

Thr Pro Arg Val Thr Gly Gly Gly Ala Met
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Pro His Glu Arg Asn Gly Phe Thr Val Leu
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Leu Leu Gln Thr Gly Ile His Val
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Ile Gly Asp Gln Tyr Val Lys Val
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Leu Phe Phe Phe Asp Ile Asp Leu
1               5

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Tyr Ser Glu His Pro Thr Phe Thr Ser Gln Tyr
1               5                   10

<210> SEQ ID NO 162
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 162

Val Leu Cys Pro Lys Asn Met Ile Ile
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Ile Tyr Arg Ile Phe Ala Glu Leu
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Leu Ala Arg Asn Leu Val Pro Met Val
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Phe Phe Trp Asp Ala Asn Asp Ile Tyr
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Pro Ser Ile Asn Val His His Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 167

Tyr Ile Leu Glu Glu Thr Ser Val Met
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Val Glu Thr Met Cys Asn Glu Tyr
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Arg Arg Ile Glu Glu Ile Cys Met Lys
1               5

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Thr Val Tyr Pro Pro Ser Ser Thr Ala Lys
1               5                   10

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Arg Arg Tyr Pro Asp Ala Val Tyr Leu
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Tyr Lys Asp Gly Asn Glu Tyr Ile
1               5
```

```
<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Ile Ile Asn Phe Glu Lys Leu
1               5

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Leu Ile Pro Asn Ala Ser Leu Ile Glu Asn Cys Thr Lys Ala Glu
1               5                   10                  15

Leu Lys Ser Ile Ile Asn Phe Glu Lys Leu
            20                  25

<210> SEQ ID NO 175
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Leu Ile Pro Asn Ala Ser Leu Ile Glu Asn Cys Thr Lys Ala Glu
1               5                   10                  15

Leu Lys Gly Tyr Lys Asp Gly Asn Glu Tyr Ile
            20                  25

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Leu Met Gly Tyr Ile Pro Leu Val
1               5

<210> SEQ ID NO 177
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Lys Leu Ile Pro Asn Ala Ser Leu Ile Glu Asn Cys Thr Lys Ala Glu
1               5                   10                  15

Leu Lys Asp Leu Met Gly Tyr Ile Pro Leu Val
            20                  25
```